United States Patent
Zhang et al.

(10) Patent No.: US 11,450,818 B2
(45) Date of Patent: Sep. 20, 2022

(54) ORGANIC COMPOUND, USE THEREOF AND ORGANIC ELECTROLUMINESCENT DEVICE USING SAME

(71) Applicant: Shaanxi Lighte Optoelectronics Material Co., Ltd., Xi'an (CN)

(72) Inventors: Wen Zhang, Xi'an (CN); Zhen Xue, Xi'an (CN); Jinping Wang, Xi'an (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 17/622,739

(22) PCT Filed: Dec. 23, 2020

(86) PCT No.: PCT/CN2020/138602
§ 371 (c)(1),
(2) Date: Dec. 24, 2021

(87) PCT Pub. No.: WO2021/136034
PCT Pub. Date: Jul. 8, 2021

(65) Prior Publication Data
US 2022/0165963 A1    May 26, 2022

(30) Foreign Application Priority Data
Dec. 30, 2019    (CN) .......................... 201911398133.8

(51) Int. Cl.
C07D 519/00    (2006.01)
C09K 11/06    (2006.01)
(Continued)

(52) U.S. Cl.
CPC ........ H01L 51/0072 (2013.01); C07D 519/00 (2013.01); C09K 11/06 (2013.01);
(Continued)

(58) Field of Classification Search
CPC .................. C07D 519/00; C09K 11/06; C09K 2211/1018; H01L 51/0052; H01L 51/0058;
(Continued)

(56) References Cited

FOREIGN PATENT DOCUMENTS

| CN | 101052636 A | 10/2007 |
|---|---|---|
| CN | 105612238 A | 5/2016 |

(Continued)

OTHER PUBLICATIONS

International Search Report from corresponding International Application No. PCT/CN2020/138602, dated Mar. 22, 2021, 6 pages.

*Primary Examiner* — Vu A Nguyen
(74) *Attorney, Agent, or Firm* — Tucker Ellis LLP

(57) ABSTRACT

The present disclosure relates to an organic compound, wherein the organic compound has a structure represented by Formula (1):

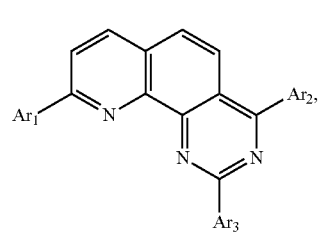

Formula (1)

wherein $Ar_1$, $Ar_2$ and $Ar_3$ are the same or different, and are each independently selected from a substituted or unsubstituted aryl having 6 to 30 carbon atoms or a substituted or unsubstituted heteroaryl having 3 to 30 carbon atoms, or a (Continued)

structure represented by Formula (2); and at least one of $Ar_1$, $Ar_2$ and $Ar_3$ has a structure represented by Formula (2);

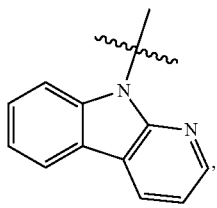

Formula (2)

⚛ represents a chemical bond. The organic compound of the present disclosure has high thermal stability and glass transition temperature, and can improve the luminous efficiency of an organic electroluminescent device and prolong the service life of the device when used as an electron transport layer material of the organic electroluminescent device.

10 Claims, 1 Drawing Sheet

(51) Int. Cl.
*H01L 51/00* (2006.01)
*H01L 51/50* (2006.01)

(52) U.S. Cl.
CPC ...... *H01L 51/0052* (2013.01); *H01L 51/0058* (2013.01); *H01L 51/0067* (2013.01); *H01L 51/0073* (2013.01); *H01L 51/0074* (2013.01); *C09K 2211/1018* (2013.01); *H01L 51/5072* (2013.01)

(58) Field of Classification Search
CPC ............. H01L 51/0067; H01L 51/0072; H01L 51/0073; H01L 51/0074; H01L 51/5072
See application file for complete search history.

(56) References Cited

FOREIGN PATENT DOCUMENTS

| | | | | |
|---|---|---|---|---|
| CN | 106749341 | A | 5/2017 | |
| CN | 110452239 | A | 11/2019 | |
| CN | 111100146 | A | 5/2020 | |
| GB | 2503789 | A | 1/2014 | |
| KR | 20150111106 | A | 10/2015 | |
| KR | 20150145131 | A | 12/2015 | |
| KR | 20170120233 | A | 10/2017 | |
| KR | 20170127593 | A | 11/2017 | |
| KR | 20180068499 | A | 6/2018 | |
| WO | 2014178532 | A1 | 11/2014 | |
| WO | WO-2015053572 | A1 * | 4/2015 | ........... C07D 401/14 |
| WO | 2018105//5 | A1 | 6/2018 | |

\* cited by examiner

ORGANIC COMPOUND, USE THEREOF AND ORGANIC ELECTROLUMINESCENT DEVICE USING SAME

CROSS REFERENCE TO RELATED APPLICATIONS

The present application claims priority to Chinese patent application No. CN201911398133.8 filed on Dec. 30, 2019, which is incorporated herein by reference in its entirety as a part of the present application.

TECHNICAL FIELD

The present disclosure relates to the field of organic light-emitting material, and specifically provides an organic compound, a use thereof, and an organic electroluminescent device using same.

BACKGROUND

An organic light-emitting diode, referred to as OLED, its the principle is that when an electric field is applied to a cathode and an anode, holes at the anode side and electrons at the cathode side will move to a light-emitting layer where the holes and electrons are combined to form excitons which release energy outward in an excited state, and light is emitted to the outside in the process of changing from energy release in an excited state to energy release in a ground state. Since molecular-scale organic electroluminescence was reported by US Kodak in 1987 and polymer electroluminescence was reported by University of Cambridge in 1990C, Countries around the world have carried out research and development on it. This material has the advantages of simple structure, high yield, low cost, active luminescence, fast response, high fraction and the like, and has the properties of low driving voltage, all-solid state, non-vacuum, anti-oscillation, low temperature resistance (−40° C.) and the like, and it is considered to be a new technique most likely to replace liquid crystal display in the future, and has attracted great attention.

In order to improve the brightness, efficiency and lifetime of the organic electroluminescent device, multilayer structures are usually used in organic electroluminescent devices, and these multilayer structures include one or more of the film layers as follows: Hole injection layer (HIL), Hole transport layer (HTL), Electron blocking layer (EBL), Emitting layer (EML), Hole blocking layer (HBL), Electron transport layer (ETL) and Electron injection layer (EIL). These film layers can improve the injection efficiency of carriers (holes and electrons) at the interfaces among layers and balance the transport capability of carriers between layers, thus improving the brightness and efficiency of the organic electroluminescent device.

SUMMARY

The present disclosure is intended to improve the luminous efficiency and service life of an organic electroluminescent device.

In order to achieve the above purpose, a first aspect of the present disclosure provides an organic compound having a structure represented by Formula (1):

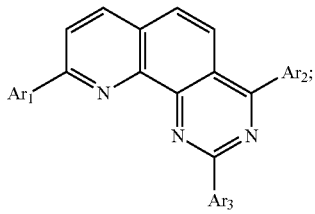

Formula (1)

wherein $Ar_1$, $Ar_2$ and $Ar_3$ are the same or different, and are each independently selected from a substituted or unsubstituted aryl having 6 to 30 carbon atoms, a substituted or unsubstituted heteroaryl having 3 to 30 carbon atoms, or a structure represented by Formula (2); and at least one of $Ar_1$, $Ar_2$ and $Ar_3$ has the structure represented by Formula (2):

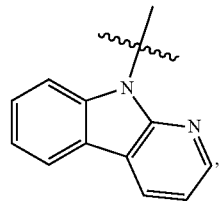

Formula (2)

⥇ represents a chemical bond;

the substituents of the $Ar_1$, $Ar_2$ and $Ar_3$ are the same or different, and are each independently selected from deuterium, a halogen, a cyano, a substituted or unsubstituted alkyl having 1 to 30 carbon atoms, a substituted or unsubstituted cycloalkyl having 3 to 30 carbon atoms, a substituted or unsubstituted heterocycloalkyl having 2 to 30 carbon atoms, a substituted or unsubstituted aryl having 6 to 30 carbon atoms, a substituted or unsubstituted heteroaryl having 1 to 30 carbon atoms, a substituted or unsubstituted alkylsilyl having 1 to 30 carbon atoms, or a substituted or unsubstituted arylsilyl having 6 to 30 carbon atoms.

A second aspect of the present disclosure provides a use of the organic compound provided in the first aspect of the present disclosure in an organic electroluminescent device.

A third aspect of the present disclosure provides an organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, and the electron transport layer contains the organic compound provided in the first aspect of the present disclosure.

Through the above technical solution, the organic compound of the present disclosure has high thermal stability and glass transition temperature, and can improve the luminous efficiency of an organic electroluminescent device and prolong the service life of the device when used as an electron transport layer material of the organic electroluminescent device.

A detailed description of other characteristics and advantages of the present disclosure will be given in the DETAILED DESCRIPTION OF THE EMBODIMENTS below.

BRIEF DESCRIPTION OF THE DRAWINGS

The figures are intended to provide a further understanding of the present disclosure and form a part of the specification. They are used for interpreting the present disclosure together with the DETAILED DESCRIPTION OF THE EMBODIMENTS below, but do not constitute a limitation to the present disclosure. In the figures.

Figure 1:
FIG. 1 illustrates a structural view of an organic electroluminescent device of an embodiment of the present disclosure.
Figure 2:
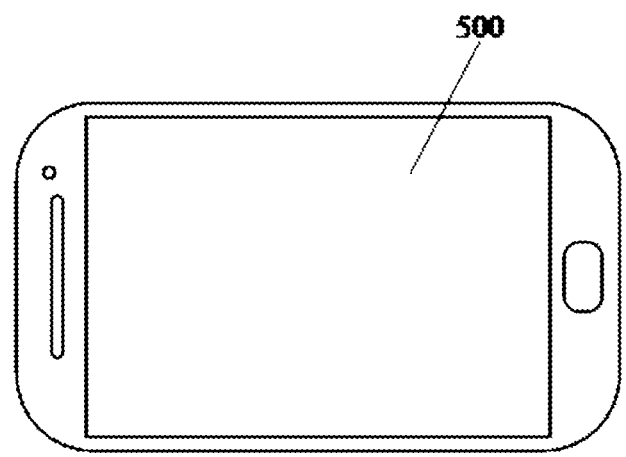
FIG. 2 illustrates a schematic view of an electronic apparatus using the organic electroluminescent device of the present disclosure.

The reference numerals of main elements in the figures are described as follows:

| 100 | Anode |
| 200 | Cathode |
| 300 | Functional layer |
| 310 | Hole injection layer |
| 320 | Hole transport layer |
| 321 | First hole transport layer |
| 322 | Second hole transport layer |
| 330 | Organic electroluminescent layer |
| 340 | Hole blocking layer |
| 350 | Electron transport layer |
| 360 | Electron injection layer |
| 370 | Electron blocking layer |
| 500 | Electronic apparatus |

DETAILED DESCRIPTION OF THE EMBODIMENTS

The example embodiments are now described more thoroughly in combination with the figures. However, the example embodiments can be implemented in multiple forms and shall not be construed as limitations to the embodiments set forth herein; on the contrary, these embodiments are provided to make the present disclosure more comprehensive and complete, and fully convey the concept of the example embodiments to those skilled in the art. The described characteristics, structures or features may be integrated into one or more embodiments in any suitable manner. In the following description, many specific details are provided to give a full understanding of the embodiments of the present disclosure.

For clarity, the thicknesses of areas and layers may be exaggerated in the figure. The same reference numerals in the FIG. represent the same or similar structures, thus detailed description of the reference numerals will be omitted.

The described characteristics, structures or features may be integrated into one or more embodiments in any suitable manner. In the following description, many specific details are provided to give a full understanding of the embodiments of the present disclosure. However, those skilled in the art will realize that the technical solution of the present disclosure may be practiced without one or more of the specific details, or other methods, constituent elements, materials and the like may be used. In other cases, well-known structures, materials or operations are not shown or described in detail to avoid obscuring the main technical ideas of the present disclosure.

The term "the" is used to indicate the existence of one or more elements/components/and the like; the terms "comprise" and "have" are used to express the meaning of open inclusion and mean that there may be other elements/components/and the like in addition to the listed elements/components/and the like.

A first aspect of the present disclosure provides an organic compound having a structure represented by Formula (1):

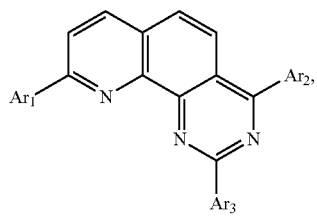

Formula (1)

wherein $Ar_1$, $Ar_2$ and $Ar_3$ are the same or different, and are each independently selected from a substituted or unsubstituted aryl having 6 to 30 carbon atoms, a substituted or unsubstituted heteroaryl having 3 to 30 carbon atoms, or a structure represented by Formula (2); and at least one of $Ar_1$, $Ar_2$ and $Ar_3$ has the structure represented by Formula (2):

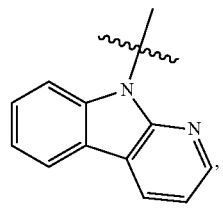

Formula (2)

⨎ represents a chemical bond;

the substituents of $Ar_1$, $Ar_2$ and $Ar_3$ are the same or different, and are each independently selected from deuterium, a halogen, a cyano, a substituted or unsubstituted alkyl having 1 to 30 carbon atoms, a substituted or unsubstituted cycloalkyl having 3 to 30 carbon atoms, a substituted or unsubstituted heterocycloalkyl having 2 to 30 carbon atoms, a substituted or unsubstituted aryl having 6 to 30 carbon atoms, a substituted or unsubstituted heteroaryl having 1 to 30 carbon atoms, a substituted or unsubstituted alkylsilyl having 1 to 30 carbon atoms, or a substituted or unsubstituted arylsilyl having 6 to 30 carbon atoms.

In the present disclosure, "at least one of $Ar_1$, $Ar_2$ and $Ar_3$ has the structure represented by Formula (2):

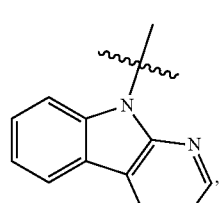

Formula (2)

means that one of Ar₁, Ar₂ and Ar₃ has the structure represented by Formula (2);

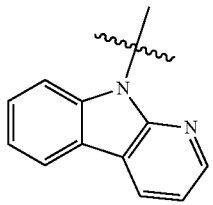

Formula (2)

or two of Ar₁, Ar₂ and Ar₃ have the structure represented by Formula (2);

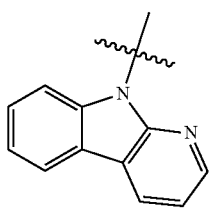

Formula (2)

or three of Ar₁, Ar₂ and Ar₃ have the structure represented by Formula (2):

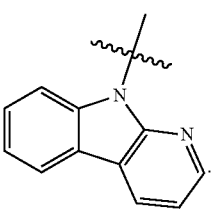

Formula (2)

The organic compound of the present disclosure is a nitrogen-containing heterocyclic rigid plane structure having a plurality of nitrogen atoms, wherein the nitrogen atoms have a strong electron donating performance, so that the structure forms a large conjugated system, and increases the electron cloud density, which is beneficial to the migration and transport of the electron. In addition, the organic compound of the present disclosure has high glass transition temperature, high thermal stability and good film forming performance, and will not interact with a light-emitting layer material to form an exciplex; the electron affinity is high, so that electrons are easily injected from the cathode; when it is used as an electron transport layer material of an organic electroluminescent device, the organic compound can improve the luminous efficiency of the organic electroluminescent device and prolong the service life of the device.

In the present disclosure, as a way of description in use, "each . . . is independently" is interchangeable with " . . . are respectively independently" and " . . . is independently selected from", all of which shall be understood in a broad sense; it can mean that the specific options expressed between the same symbols in different groups do not affect each other, and can also indicate that the specific options expressed between the same symbols in the same group do not affect each other. For example, "Formula Q-1 Formula Q-2,

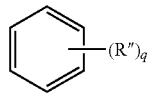

Formula Q-1

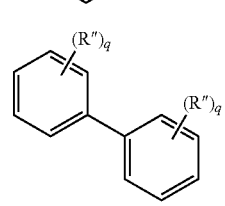

Formula Q-2 wherein each q is independently 0, 1, 2 or 3, and each R" is independently selected from a hydrogen, a deuterium, a fluorine or a chlorine, which means that: Formula Q-1 indicates that there are q substituents R" on a benzene ring, each R" may be the same or different, and the options of each R" do not affect each other; Formula Q-2 indicates that there are q substituents R" on each benzene ring of biphenyl, the number q of R" substituents on the two benzene rings may be the same or different, each R" may be the same or different, and the options of each R" do not affect each other.

In the present disclosure, the term "substituted or unsubstituted" refers to no substituent or being substituted by one or more substituents. The substituents include, but are not limited to, deuterium, halogen (F, Cl, Br), cyano, alkyl, alkenyl, alkynyl, haloalkyl, aryl, heteroaryl, aryloxy, arylthio, silyl, alkylamine, cycloalkyl or heterocyclyl.

In the present disclosure, "alkyl" may include linear alkyl or branched alkyl. The alkyl can have 1 to 10 carbon atoms, in the present disclosure, a numerical range such as "1 to 10" refers to each integer in a given range; for example, "1 to 10 carbon atoms" refers to the alkyl that can contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms. The alkyl may also be lower alkyl with 1 to 6 carbon atoms. In addition, the alkyl may be substituted or unsubstituted.

Preferably, the alkyl is selected from an alky having 1 to 5 carbon atoms, and specific examples of the alkyl include but not limited to methyl, ethyl, n-propyl, isopropyl, n-butyl, iso-butyl, sec-butyl, tert-butyl and pentyl.

In the present disclosure, the number of carbon atoms of Ar₁, Ar₂ and Ar₃ refers to the number of all carbon atoms. For example, if Ar₁, Ar₂ and Ar₃ are selected from a substituted aryl having 30 carbon atoms, the number of all carbon atoms of the aryl and the substituent thereof is 30.

In the present disclosure, "hetero" means that one functional group comprises at least one heteroatom such as B, O, N, P, Si, Se or S and the rest atoms are carbon and hydrogen when no specific definition is additionally provided.

In the present disclosure, the aryl refers to an optional functional group or substituent derived from an aromatic hydrocarbon ring. The aryl may be a monocyclic aryl or a polycyclic aryl, in other words, the aryl may be a monocyclic aryl, a fused ring aryl, two or more monocyclic aryls conjugated by carbon-carbon bonds, a monocyclic aryl and a fused ring aryl conjugated by carbon-carbon bonds, and two or more fused ring aryls conjugated by carbon-carbon bonds. That is, two or more aromatic groups conjugated by carbon-carbon bonds can also be regarded as the aryl of the present disclosure. Wherein the aryl does not contain heteroatoms such as B, O, N, P, Si, Se or S. For example, in the present disclosure, biphenyl, triphenyl, naphthyl, anthracyl and the like belong to aryl herein. Examples of the aryl may include, but are not limited to, phenyl, naphthyl, fluorenyl, anthracyl, phenanthryl, biphenyl, triphenyl, tetrabiphenyl, pentabiphenyl, hexabiphenyl, benzo[9,10]phenanthryl, pyrenyl, benzofluoranthenly and the like.

In the present disclosure, the substituted aryl means that one or more hydrogen atoms in the aryl are substituted by other groups. For example, at least one hydrogen atom is substituted by a deuterium atom, F, Cl, Br, I, CN, a hydroxyl, an amino, a branched alkyl, a linear alkyl, a cycloalkyl, an alkoxy, an alkylamine or other groups. It is understood that the substituted aryl having 18 carbon atoms means that the total number of carbon atoms of the aryl and the substituents of the aryl is 18. For example, the number of carbon atoms of 9,9-dimethylfluorenyl is 15.

In the present disclosure, examples of the aryl as a substituent herein include, but are not limited to, phenyl, biphenyl, naphthyl, 9,9-dimethylfluorenyl, 9,9-diphenylfluorenyl, spirodifluorenyl, anthracyl, phenanthryl or chrysenyl.

The unsubstituted aryl herein refers to an aryl having 6 to 30 carbon atoms, such as: phenyl, biphenyl, triphenyl, tetrabiphenyl, naphthyl, pyrenyl, dimethylfluorenyl, 9,9-diphenylfluorenyl, spirodifluorenyl, anthracyl, phenanthryl, chrysenyl, azulenyl, acenaphthenyl, benzoanthracenyl, perylenyl, indenyl, naphthacene and the like. A substituted aryl having 6 to 30 carbon atoms means that at least one hydrogen atom is substituted by a deuterium atom, F, Cl, I, CN, a hydroxyl, a nitro, an amino and the like.

In the present disclosure, the heteroaryl may be a heteroaryl including at least one of B, O, N, P, Si, Se and S as a heteroatom. The heteroaryl may be a monocyclic or polycyclic heteroaryl, in other words, the heteroaryl is either a single aromatic ring system or a plurality of aromatic ring systems conjugated by carbon-carbon bonds, and any aromatic ring system is an aromatic monocycle or an aromatic fused ring. Exemplarily, the heteroaryl may include, but is not limited to, thiophenyl, furanyl, pyrrolyl, imidazolyl, thiazolyl, oxazolyl, oxadiazole, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, N-phenylcarbazolyl, N-heteroarylcarbazolyl, N-alkylcarbazolyl, benzoxazolyl, benzimidazolyl, benzothiazolyl, benzocarbazolyl, benzothiophenyl, dibenzothiophenyl, thiophenothiophenyl, benzofuranyl, phenanthrolinyl, isoxazolyl, thiadiazolyl, benzothiazolyl, phenothiazinyl, dibenzosilyl, dibenzofuranyl, phenyl substituted dibenzofuranyl, dibenzofuranyl substituted phenyl and the like. Wherein thiophenyl, furanyl, phenanthrolinyl and the like are heteroaryls of a single aromatic ring system, and N-arylcarbazolyl, N-heteroarylcarbazolyl, phenyl substituted dibenzofuranyl, dibenzofuranyl substituted phenyl and the like are heteroaryls of a plurality of aromatic ring systems conjugated by carbon-carbon bonds.

In the present disclosure, heteroaryls as substituents are for example, but are not limited to pyridyl, pyrimidyl, carbazolyl, dibenzofuranyl and dibenzothiophenyl.

The "rings" herein include saturated rings and unsaturated rings; saturated rings are cycloalkyl and heterocycloalkyl, and unsaturated rings are cycloalkenyl, heterocycloalkenyl, aryl and heteroaryl.

In the present disclosure, "─┼─" and "*─┼─" have the same meaning, and both of them refer to the position bound with other substituents or binding sites.

A non-orientating connection bond herein refers to a single bond "*─┼─" or "─┼─" protruding from a ring system, which means that one end of the connection bond can be connected to any position in the ring system penetrated by the bond, and the other end is connected to the rest of a compound molecule. For example, as shown in the following Formula (f), the naphthyl represented by Formula (f) is connected with other positions of the molecule through two non-orientating connection bonds penetrating double rings, and what it means includes any possible connection mode represented by Formula (f-1) to Formula (f-10).

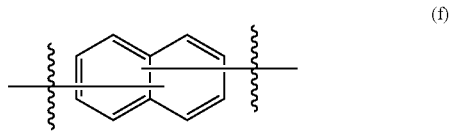

(f)

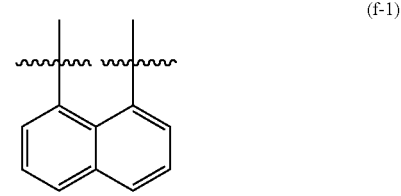

(f-1)

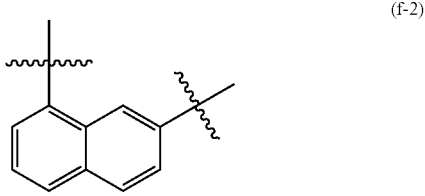

(f-2)

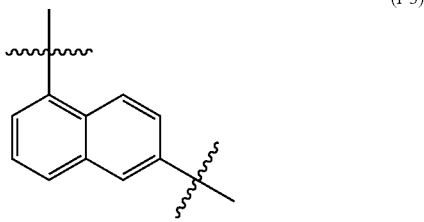

(f-3)

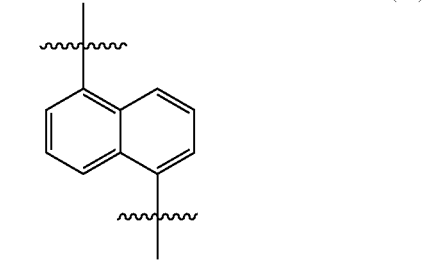

(f-4)

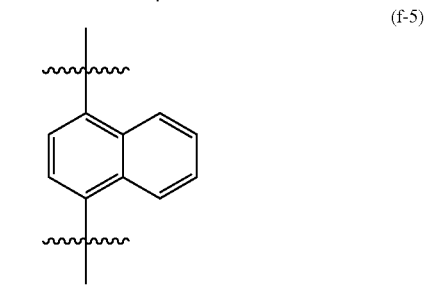

(f-5)

(f-6)
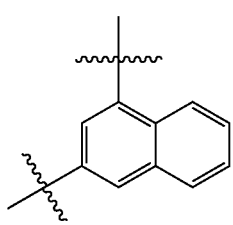

(f-7)
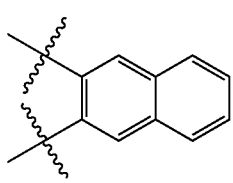

(f-8)
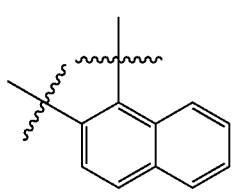

(f-9)
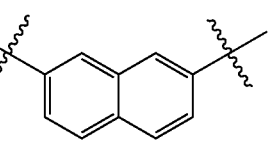

(f-10)
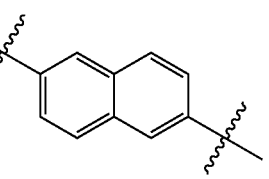

For example, as shown in the following Formula (X'), the phenanthryl represented by Formula (X') is connected with other positions of the molecule through a non-orientating connection bond protruding from a benzene ring at one side, and what it means includes any possible connection mode represented by Formula (X'-1) to Formula (X'-4).

(X')
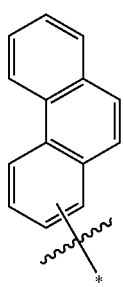

(X'-1)
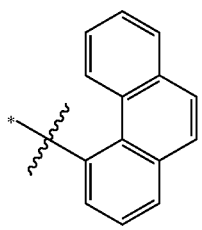

(X'-2)
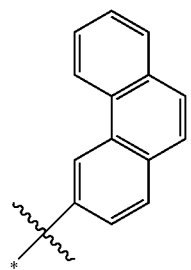

(X'-3)
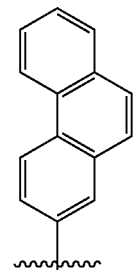

(X'-4)
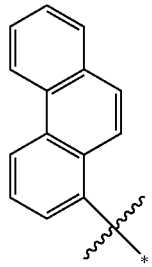

A non-orientating substituent herein refers to a substituent connected by a single bond protruding from the center of a ring system, which means that the substituent can be connected in any possible site in the ring system. For example, as shown in the following Formula (Y), the substituent R group represented by Formula (Y) is connected with a quinoline ring through a non-orientating connection bond, and what it means includes any possible connection mode represented by Formula (Y-1) to Formula (Y-7).

(Y)
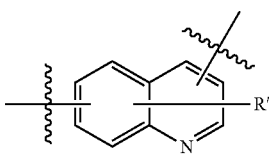

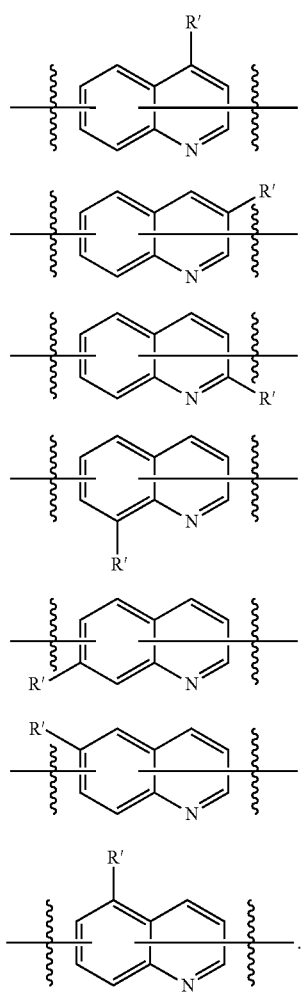

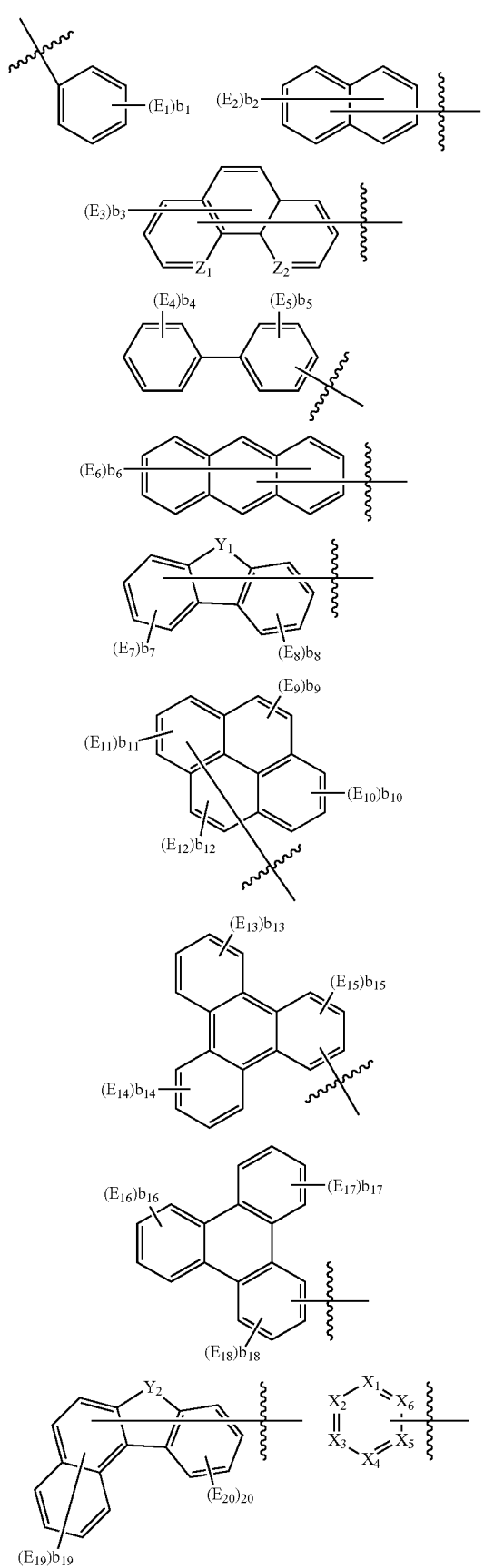

In the present disclosure, halogen groups may be for example fluorine, chlorine, bromine or iodine.

In a specific embodiment of the present disclosure, $Ar_1$, $Ar_2$ and $Ar_3$ are the same or different, and are each independently selected from a substituted or unsubstituted aryl having 6 to 25 carbon atoms, or a substituted or unsubstituted heteroaryl having 3 to 20 carbon atoms.

In a specific embodiment of the present disclosure, $Ar_1$, $Ar_2$ and $Ar_3$ are the same or different, and are each independently selected from a substituted or unsubstituted aryl having 6 to 25 carbon atoms, or a substituted or unsubstituted heteroaryl having 5 to 12 carbon atoms.

In a specific embodiment of the present disclosure, the substituents of $Ar_1$, $Ar_2$ and $Ar_3$ are each independently selected from deuterium, a fluorine, a cyano, an alkyl having 1 to 5 carbon atoms, a substituted or unsubstituted aryl having 6 to 18 carbon atoms, or a substituted or unsubstituted heteroaryl having with 3 to 12 carbon atoms.

In a preferred specific embodiment of the present disclosure, at least two of $Ar_1$, $Ar_2$ and $Ar_3$ have the structure represented by Formula (2).

In a specific embodiment of the present disclosure, $Ar_1$, $Ar_2$ and $Ar_3$ are the same or different, and are each independently selected from a group consisting of the following general formulas:

-continued

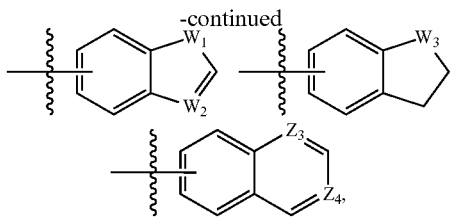

wherein $b_1$ and $b_4$ are the same or different, and are each independently selected from 0, 1, 2, 3, 4 or 5;

$b_5$, $b_7$, $b_8$, $b_{13}$, $b_{14}$, $b_{16}$, $b_{17}$ and $b_{20}$ are the same or different, and are each independently selected from 0, 1, 2, 3 or 4;

$b_2$ and $b_3$ are the same or different, and are each independently selected from 0, 1, 2, 3, 4, 5, 6 or 7;

$b_{10}$, $b_{11}$, $b_{15}$ and $b_{18}$ are the same or different, and are each independently selected from 0, 1, 2 or 3;

$b_6$ is selected from 0, 1, 2, 3, 4, 5, 6, 7, 8 or 9;

$b_9$ and $b_{12}$ are the same or different, and are each independently selected from 0, 1 or 2;

$b_{19}$ is selected from 0, 1, 2, 3, 4, 5 or 6;

$Z_1$, $Z_2$, $Z_3$ and $Z_4$ are the same or different, and are each independently selected from $C(E_{21})$ or $N(E_{22})$; each $E_{21}$ are the same or different, each $E_{22}$ are the same or different, and at least one of $Z_3$ and $Z_4$ is $N(E_{22})$;

$Y_1$ and $Y_2$ are the same or different, and are each independently selected from O, S, $Si(E_{23}E_{24})$, $C(E_{25}E_{26})$, $N(E_{27})$ or Se;

$W_3$ is selected from O or S;

$X_1$ to $X_6$ are the same or different, and are each independently selected from C(E') or N, at least one of $X_1$ to $X_6$ is N, where E' in $X_1$ to $X_6$ are the same or different, and are each independently selected from hydrogen, an alkyl having 1 to 10 carbon atoms, an aryl having 6 to 18 carbon atoms, a heteroaryl having 3 to 18 carbon atoms or a cycloalkyl having 3 to 10 carbon atoms, or adjacent E' are connected to form a ring;

$W_1$ is selected from $C(E_{28}E_{29})$, O or $N(E_{30})$, $W_2$ is selected from C(Q') or N, Q' is selected from hydrogen, an alkyl having 1 to 10 carbon atoms, an aryl having 6 to 18 carbon atoms, a heteroaryl having 3 to 18 carbon atoms or a cycloalkyl having 3 to 10 carbon atoms;

$E_1$ to $E_{30}$ are each independently selected from hydrogen, deuterium, a halogen atom, a cyano, an alkyl having 1 to 10 carbon atoms, an aryl having 6 to 18 carbon atoms, a heteroaryl having 3 to 18 carbon atoms or a cycloalkyl having 3 to 10 carbon atoms, or $E_{23}$ and $E_{24}$ are connected to form a ring, or $E_{25}$ and $E_{26}$ are connected to form a ring, or $E_{28}$ and $E_{29}$ are connected to form a ring.

In the present disclosure, $b_1$ is the number of substituents $E_1$, and when $b_1$ is greater than or equal to 2, any two $E_1$ are the same or different; $b_2$ is the number of substituents $E_2$, and when $b_2$ is greater than or equal to 2, any two $E_2$ are the same or different; $b_3$ is the number of substituents $E_3$, and when $b_3$ is greater than or equal to 2, any two $E_3$ are the same or different; $b_4$ is the number of substituents $E_4$, and when $b_4$ is greater than or equal to 2, any two $E_4$ are the same or different; $b_5$ is the number of substituents $E_5$, and when $b_5$ is greater than or equal to 2, any two $E_5$ are the same or different; $b_6$ is the number of substituents $E_6$, and when $b_6$ is greater than or equal to 2, any two $E_6$ are the same or different; $b_7$ is the number of substituents $E_7$, and when $b_7$ is greater than or equal to 2, any two $E_7$ are the same or different; $b_8$ is the number of substituents $E_8$, and when $b_8$ is greater than or equal to 2, any two $E_8$ are the same or different; $b_9$ is the number of substituents $E_9$, and when $b_9$ is greater than or equal to 2, any two $E_9$ are the same or different; $b_{10}$ is the number of substituents $E_{10}$, and when $b_{10}$ is greater than or equal to 2, any two $E_{10}$ are the same or different; $b_{11}$ is the number of substituents $E_{11}$, and when $b_{11}$ is greater than or equal to 2, any two $E_{11}$ are the same or different; $b_{12}$ is the number of substituents $E_{12}$, and when $b_{12}$ is greater than or equal to 2, any two $E_{12}$ are the same or different; $b_{13}$ is the number of substituents $E_{13}$, and when $b_{13}$ is greater than or equal to 2, any two $E_{13}$ are the same or different; $b_{14}$ is the number of substituents $E_{14}$, and when $b_{14}$ is greater than or equal to 2, any two $E_{14}$ are the same or different; $b_{15}$ is the number of substituents $E_{15}$, and when $b_{15}$ is greater than or equal to 2, any two $E_{15}$ are the same or different; $b_{16}$ is the number of substituents $E_{16}$, and when $b_{16}$ is greater than or equal to 2, any two $E_{16}$ are the same or different; $b_{17}$ is the number of substituents $E_{17}$, and when $b_{17}$ is greater than or equal to 2, any two $E_{17}$ are the same or different; $b_{18}$ is the number of substituents $E_{18}$, and when $b_{18}$ is greater than or equal to 2, any two $E_{18}$ are the same or different; $b_{19}$ is the number of substituents $E_{19}$, and when $b_{19}$ is greater than or equal to 2, any two $E_{19}$ are the same or different; $b_{20}$ is the number of substituents $E_{20}$, and when $b_{20}$ is greater than or equal to 2, any two $E_{20}$ are the same or different.

In the present disclosure, a benzene ring is not substituted when $b_1$ to $b_{20}$ are selected from 0.

In the present disclosure, the meaning of A and B "can be connected to form a ring" includes that A and B are independent of each other and not connected; and it also includes that A and B are connected with each other to form a ring. For example, $E_{23}$ and $E_{24}$ can be connected to form a ring, including the way in which $E_{23}$ and $E_{24}$ are mutually independent and not connected, and the way in which $E_{23}$ and $E_{24}$ are mutually connected to form a ring; $E_{25}$ and $E_{26}$ can be connected to form a ring, including the way in which $E_{25}$ and $E_{26}$ are mutually independent and not connected, and the way in which $E_{25}$ and $E_{26}$ are mutually connected to form a ring; $E_{28}$ and $E_{29}$ can be connected to form a ring, including the way in which $E_{28}$ and $E_{29}$ are mutually independent and not connected, and the way in which $E_{28}$ and $E_{29}$ are mutually connected to form a ring.

Adjacent E' can be connected to form a ring, which means that $X_1$ and $X_2$ form a ring, or $X_2$ and $X_3$ form a ring, or $X_3$ and $X_4$ form a ring, or $X_4$ and $X_5$ form a ring, or $X_5$ and $X_6$ form a ring, of course, it also includes cases such as $X_3$ and $X_4$ form a ring and $X_5$ and $X_6$ form a ring and the like.

For example, $X_3$ and $X_4$ can be connected to form a ring, including the way in which E of $X_3$ and E' of $X_4$ are mutually independent and not connected, and the way in which E' of $X_3$, E' of $X_4$ and atoms connected by E' are connected to form a ring.

In the present disclosure, the ring refers to a saturated or unsaturated 5 to 13-membered ring; when $E_{11}$ and $E_{12}$ form a ring, the number of carbon atoms of the ring may be a 5-membered ring, for example

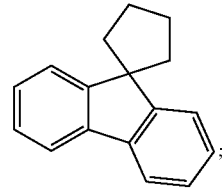 [SMILES: c1ccc2c(c1)-c1ccccc1C21CCCC1]

it may also be a 6-membered ring, for example
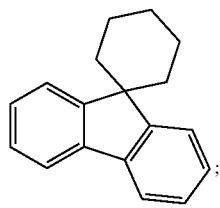 [SMILES: c1ccc2c(c1)-c1ccccc1C21CCCCC1]
it may also be a 13-membered ring, for example
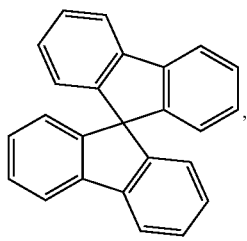 [SMILES: c1ccc2c(c1)-c1ccccc1C21c2ccccc2-c2ccccc21]
etc, but is not limited to.
In a specific embodiment of the present disclosure, $Ar_1$, $Ar_2$ and $Ar_3$ are the same or different, and are each independently selected from a group consisting of the following groups:
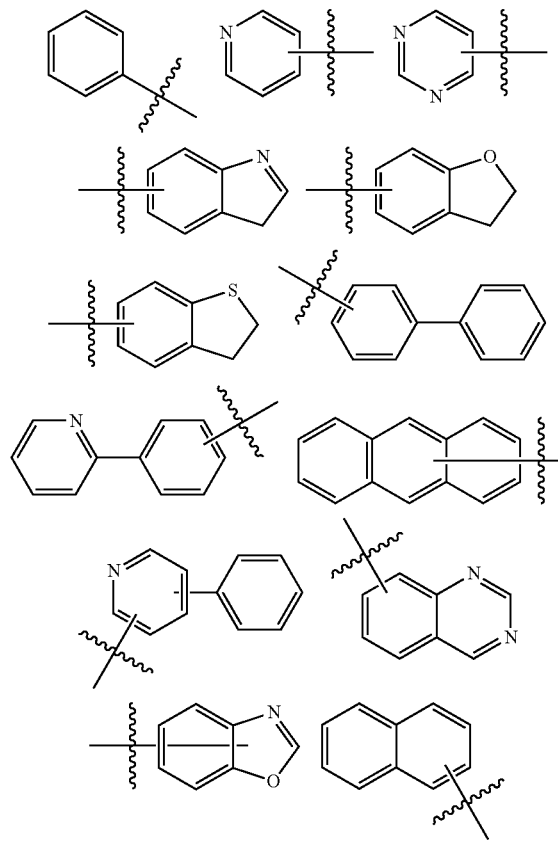
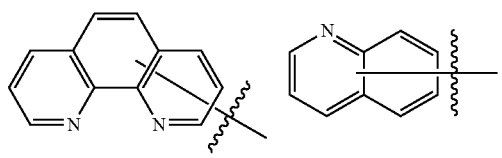
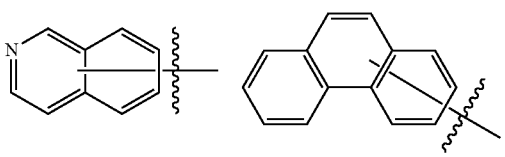
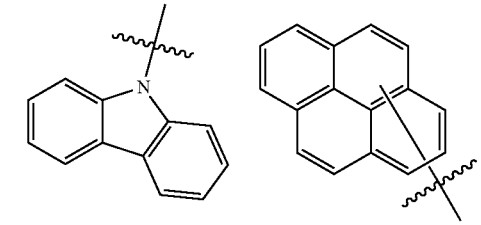
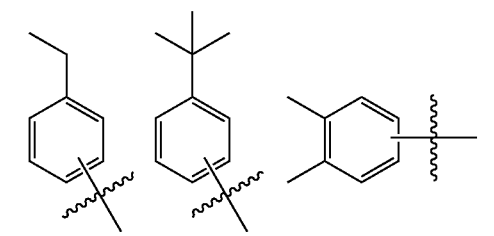
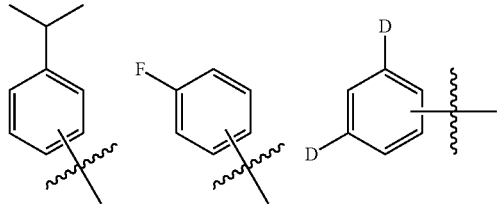
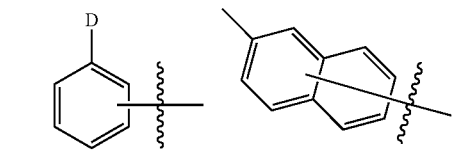
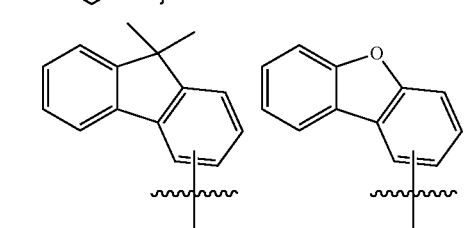
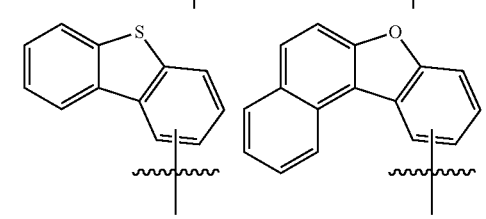

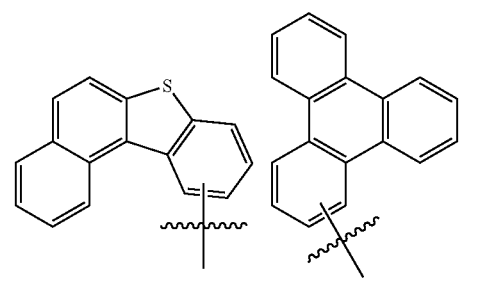

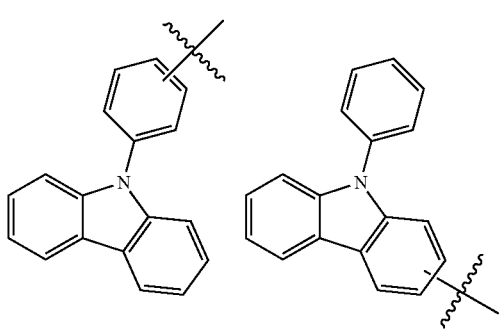

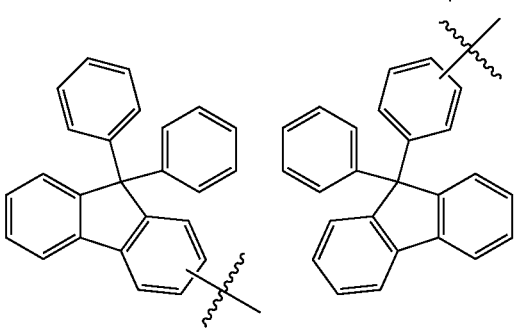

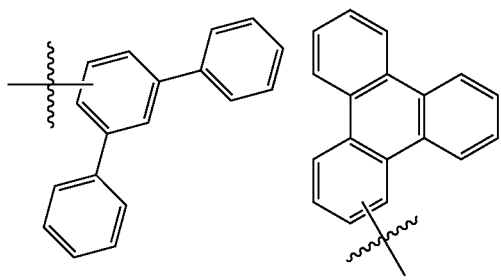

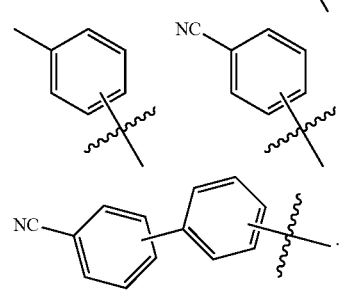

In a specific embodiment of the present disclosure, $Ar_1$, $Ar_2$ and $Ar_3$ are the same or different, and are each independently selected from a group consisting of the following groups or the structure represented by Formula (2):

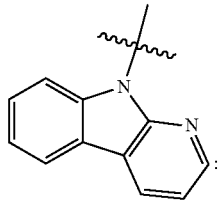

Formula (2)

a substituted or unsubstituted phenyl, a substituted or unsubstituted pyridyl, a substituted or unsubstituted pyrimidyl, a substituted or unsubstituted 3H-indolyl, a substituted or unsubstituted 2,3-dihydrobenzofuranyl, a substituted or unsubstituted 2,3-dihydrobenzothiophenyl, a substituted or unsubstituted biphenyl, a substituted or unsubstituted anthracyl, a substituted or unsubstituted quinazolinyl, a substituted or unsubstituted benzoxazolyl, a substituted or unsubstituted naphthyl, a substituted or unsubstituted phenanthrolinyl, a substituted or unsubstituted quinolinyl, a substituted or unsubstituted isoquinolyl, a substituted or unsubstituted phenanthryl, a substituted or unsubstituted carbazolyl, a substituted or unsubstituted pyrenyl, a substituted or unsubstituted fluorenyl, a substituted or unsubstituted dibenzofuranyl, a substituted or unsubstituted dibenzothiophenyl, a substituted or unsubstituted benzo[b]naphtho[1,2-d]furanyl, a substituted or unsubstituted benzo[b]naphtho[1,2-d]thiophenyl, a substituted or unsubstituted 9,10-benzophenanthryl, or a substituted or unsubstituted N-phenylcarbazolyl, wherein at least one of $Ar_1$, $Ar_2$ and $Ar_3$ has the structure represented by Formula (2):

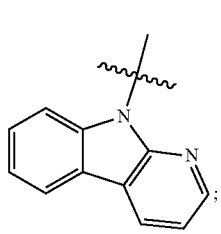

Formula (2)

preferably, the substituents of $Ar_1$, $Ar_2$ and $Ar_3$ are each independently selected from deuterium, a fluorine, a cyano, a methyl, an ethyl, an isopropyl, a tert-butyl, a phenyl, a naphthyl, a biphenyl, a pyridyl, a carbazolyl, a dibenzofuranyl, a dibenzothiophenyl or a phenyl substituted fluorenyl.

In a specific embodiment of the present disclosure, $Ar_1$, $Ar_2$ and $Ar_3$ are the same or different, and are each independently selected from a group consisting of the following groups:

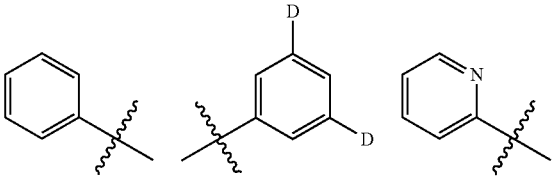

-continued

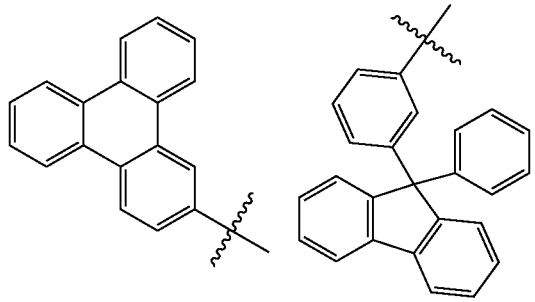

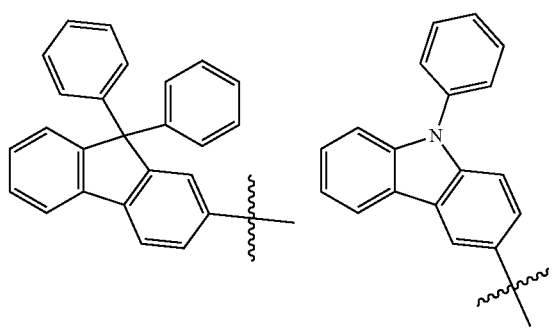

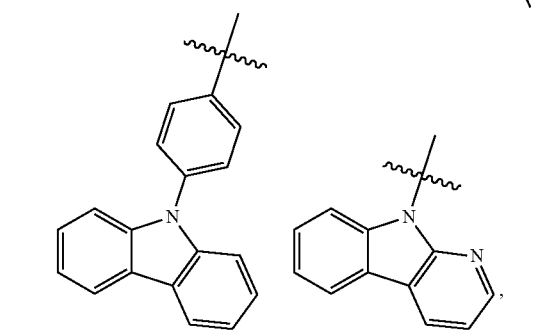

wherein, at least one of Ar$_1$, Ar$_2$ and Ar$_3$ has the structure represented by Formula (2):

Formula (2)

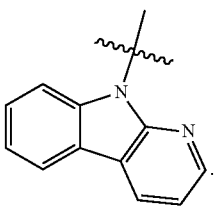

In one embodiment of the present disclosure, the substituents of Ar$_1$, Ar$_2$ and Ar$_3$ are each independently selected from deuterium, a fluorine, a cyano, a methyl, an ethyl, an isopropyl, a tert-butyl, a phenyl, a naphthyl, a biphenyl, a pyridyl, a carbazolyl, a dibenzofuranyl, a dibenzothiophenyl or a phenyl substituted fluorenyl.

In one embodiment of the present disclosure, the compound may be selected from one or more of the following compounds P1 to P108:

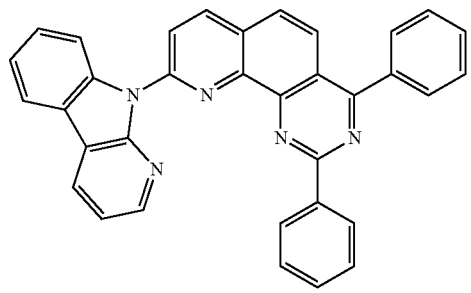
P1

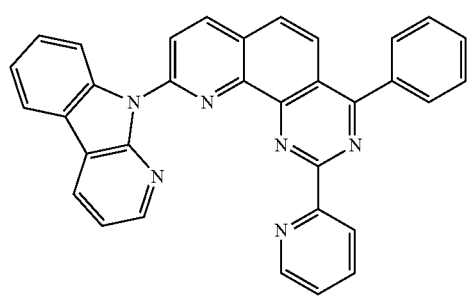
P2

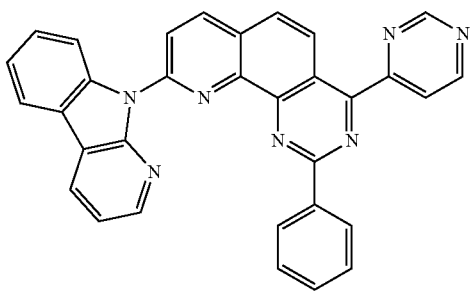
P3

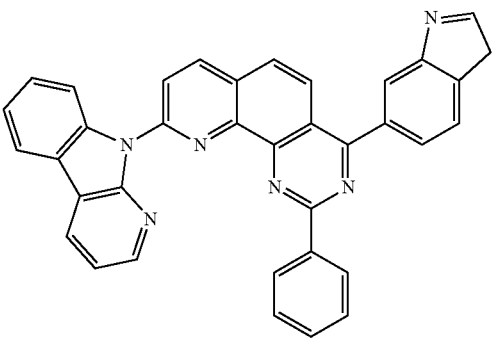
P4

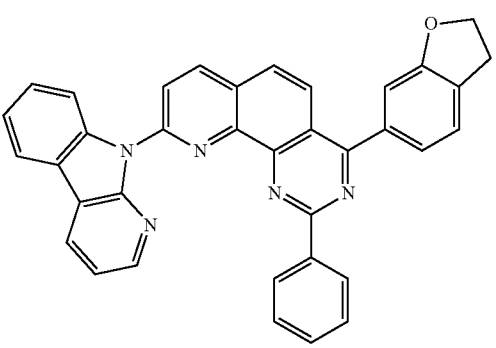
P5

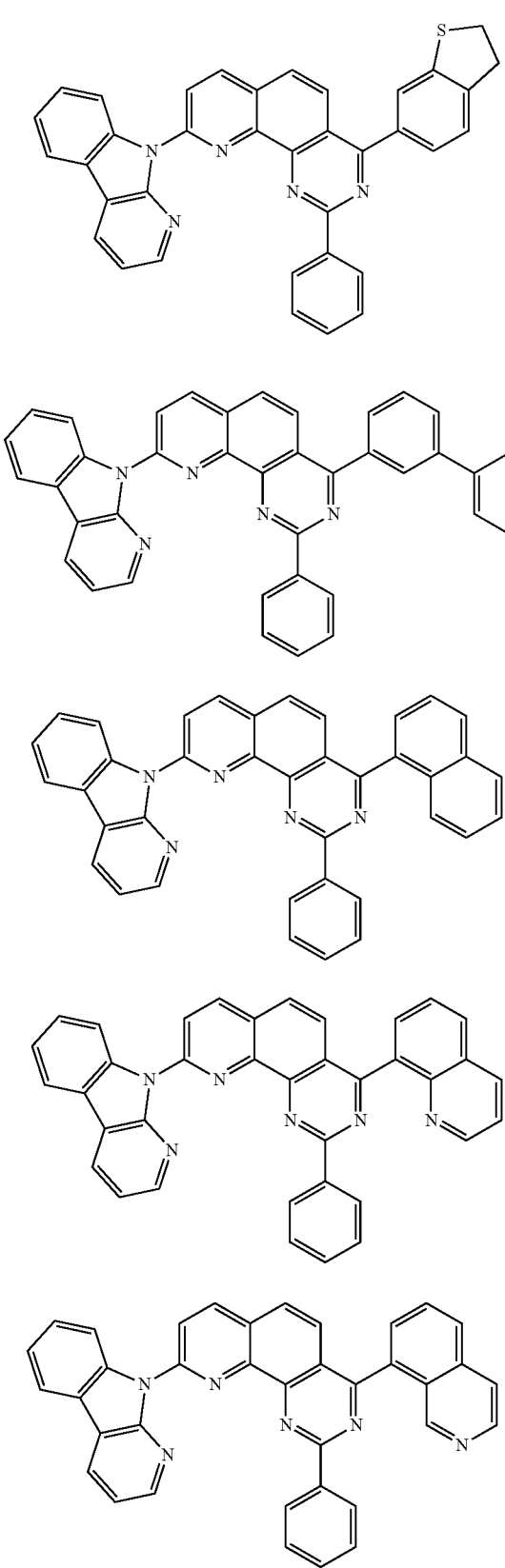
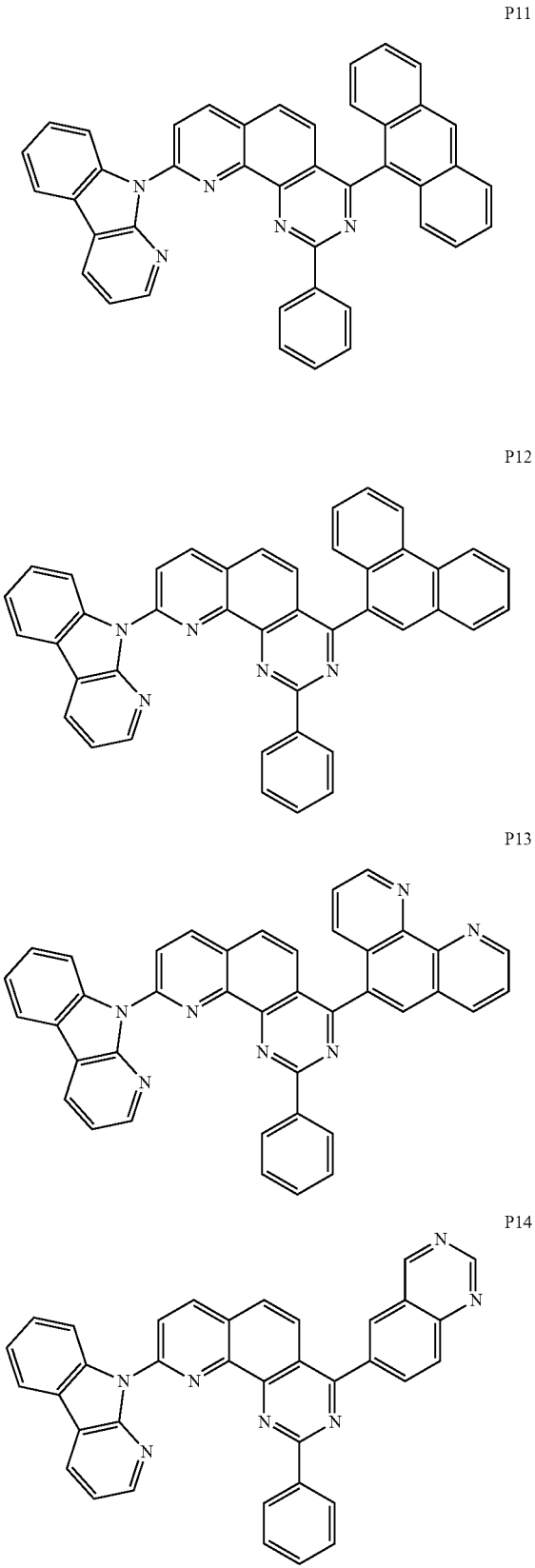

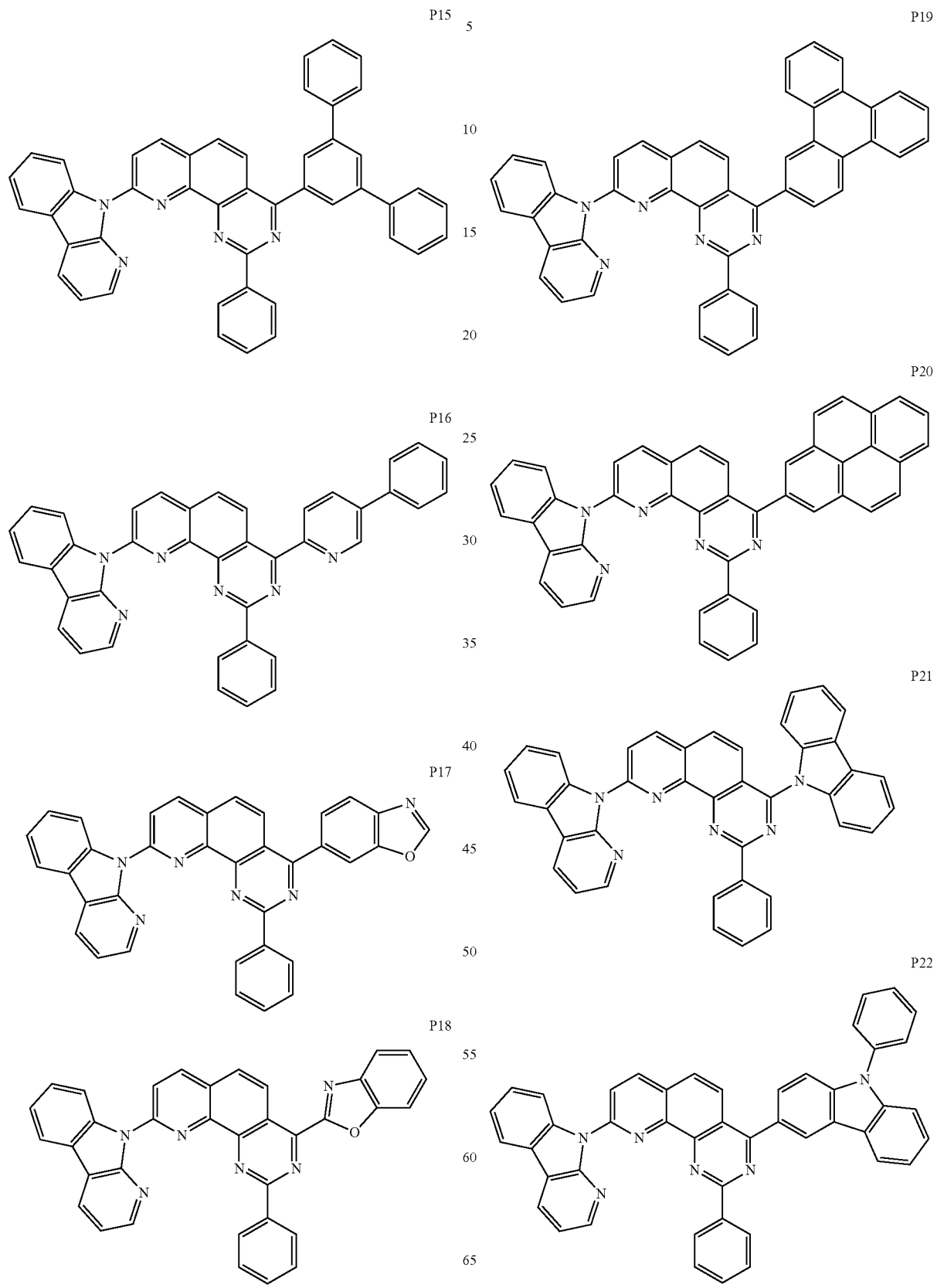

P23
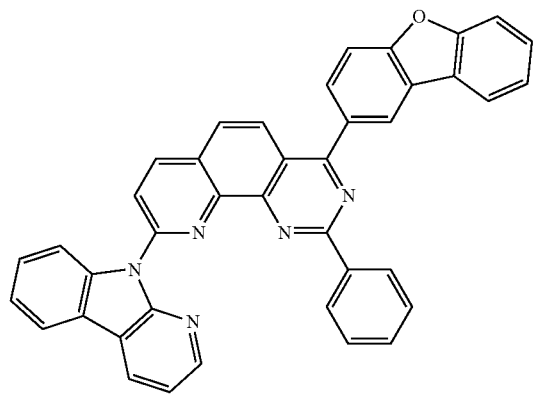
P24
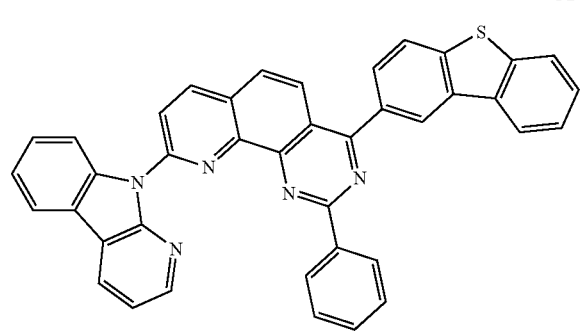
P25
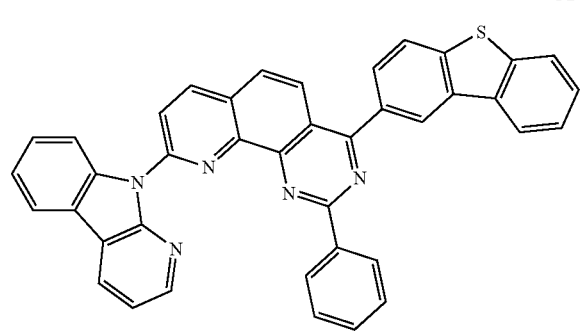
P26
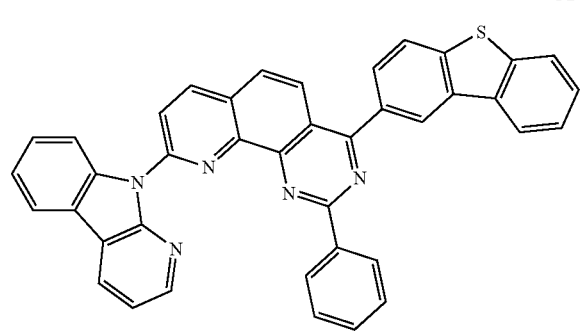
P27
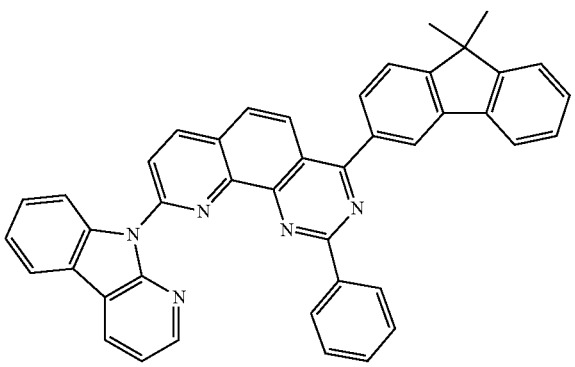
P28
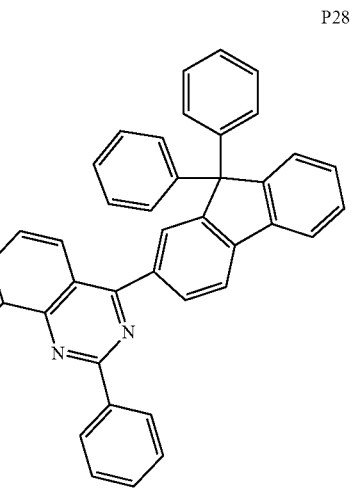
P29
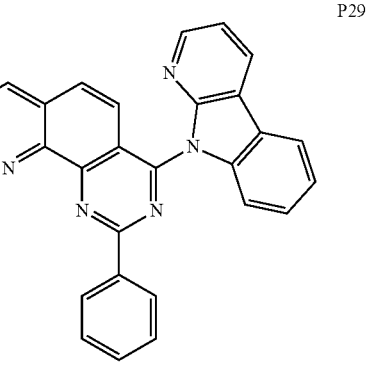
P30
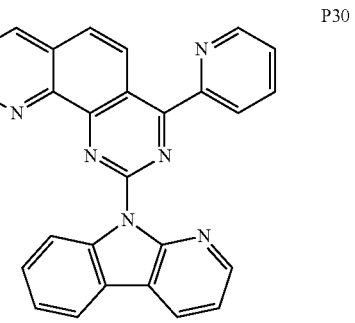

P31
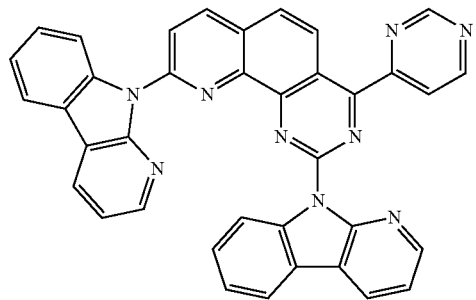
P32
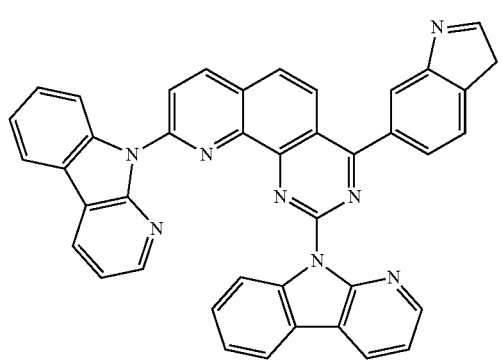
P33
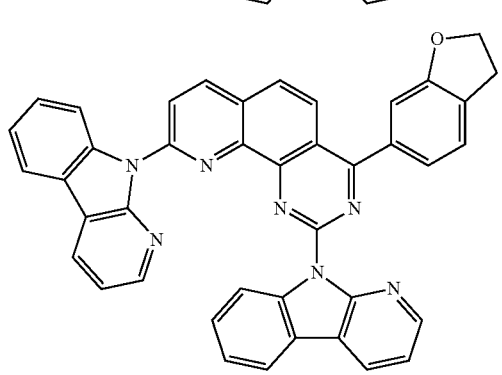
P34
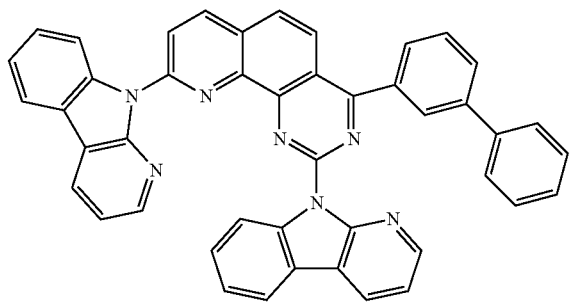
P35
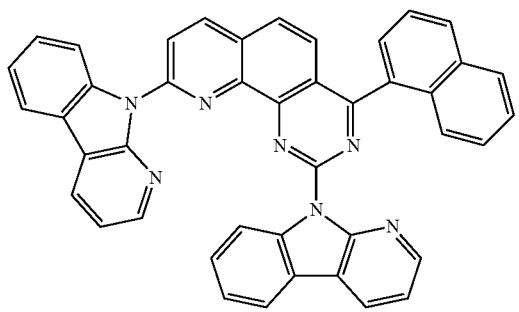
P36
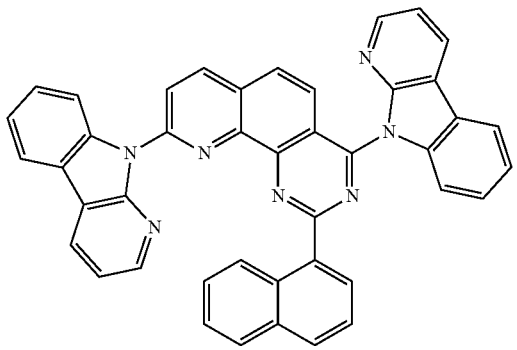
P37
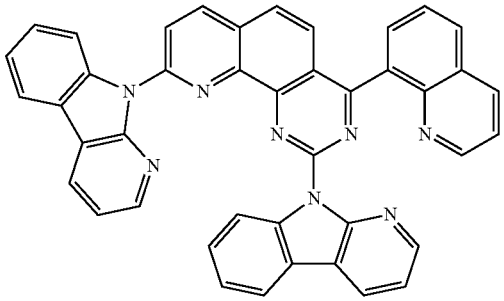
P38
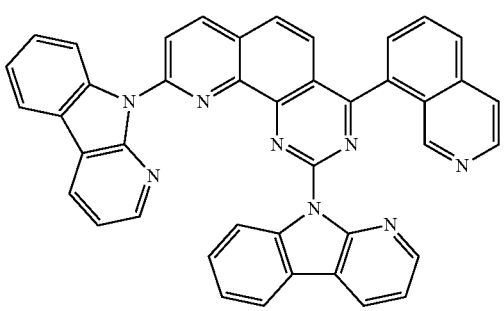
P39
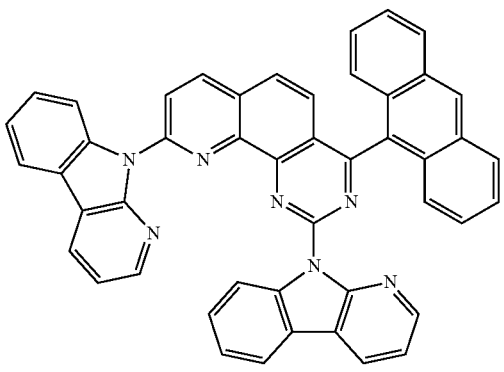

-continued
P40
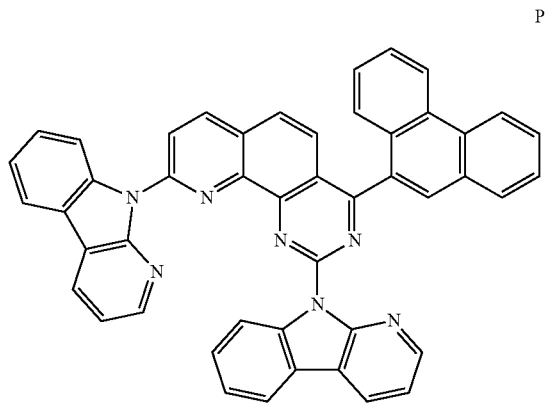
P41
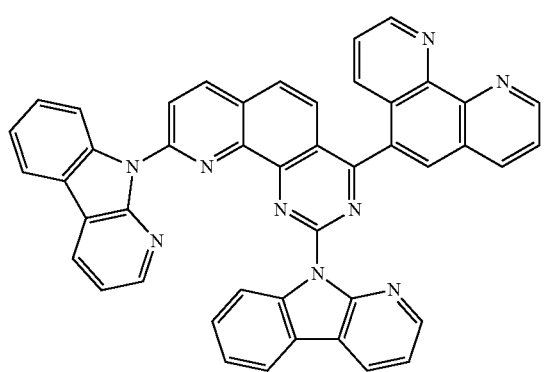
P42
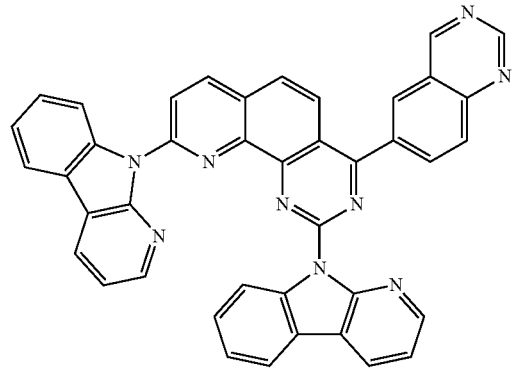
P43
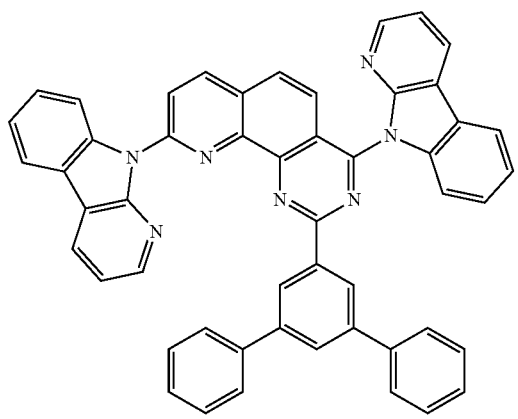
P44
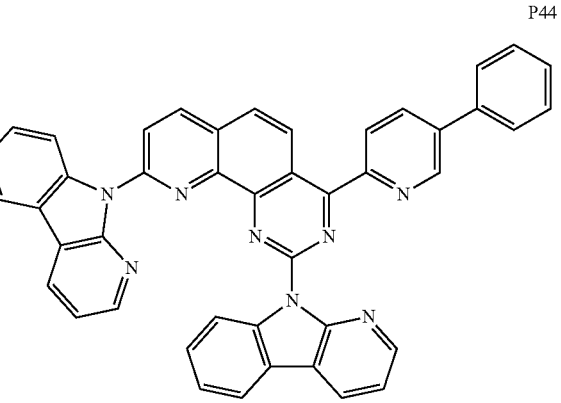
P45
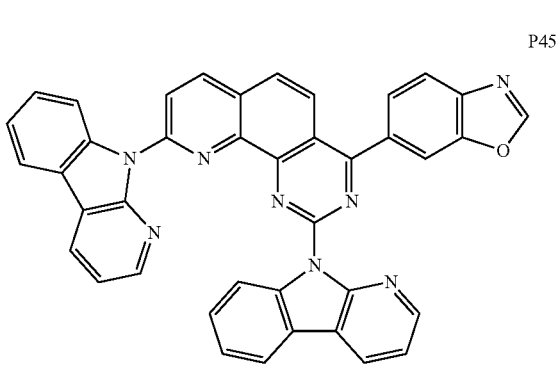
P46
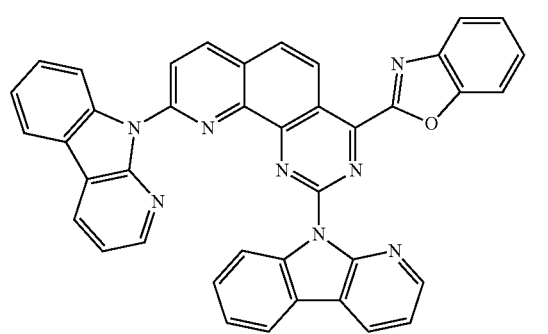
P47
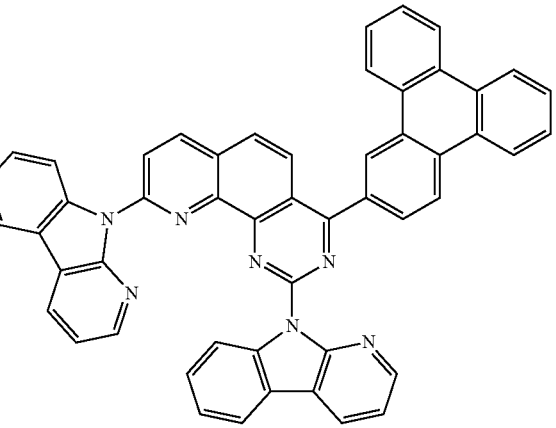

P48
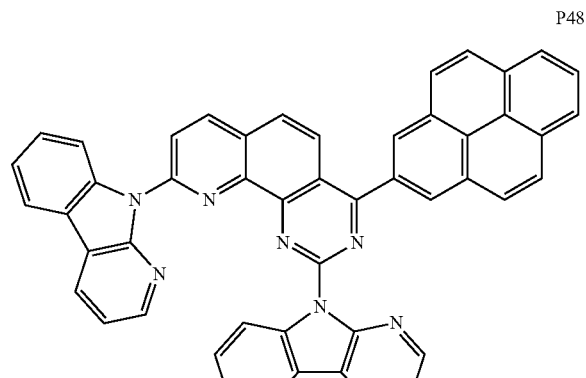
P49
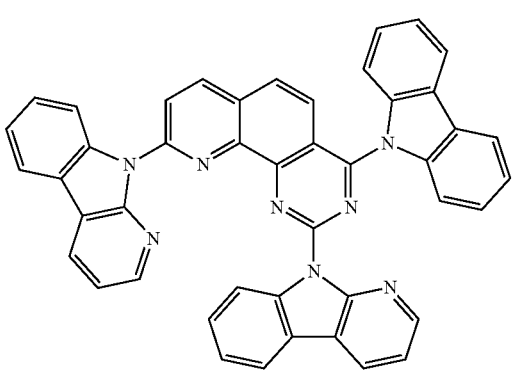
P50
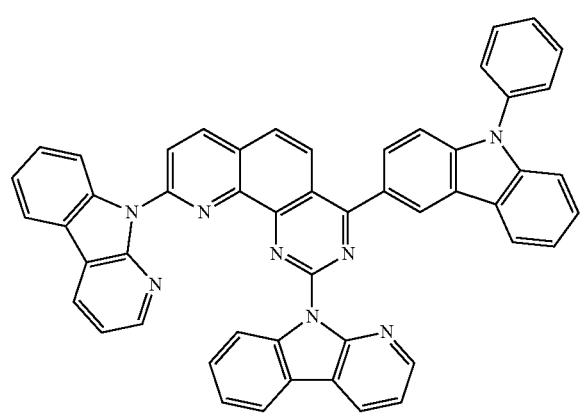
P51
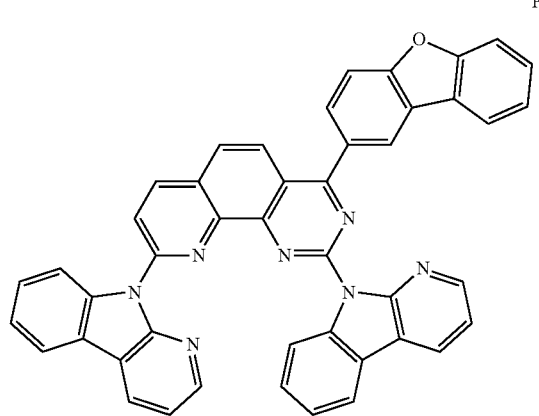
P52
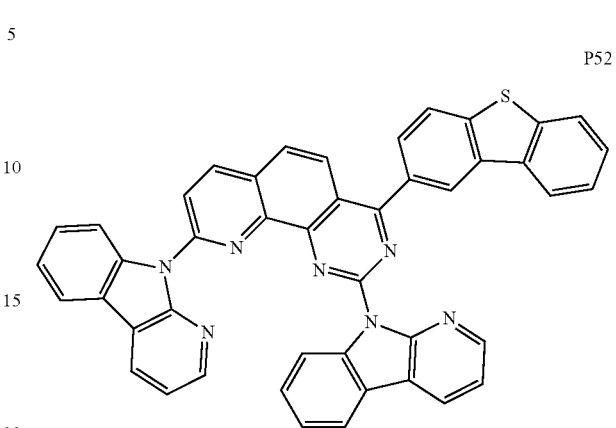
P53
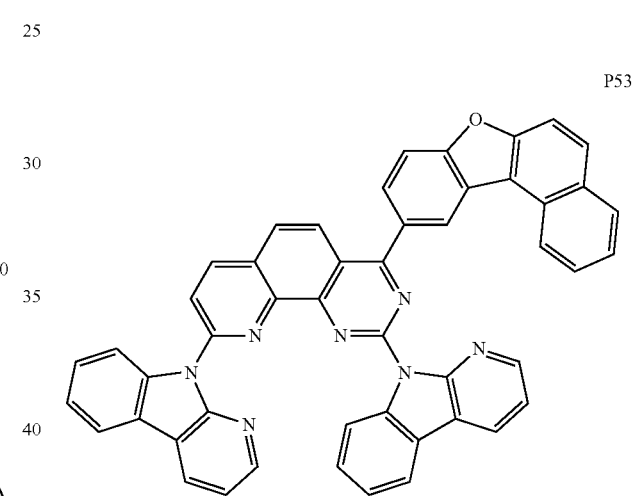
P54
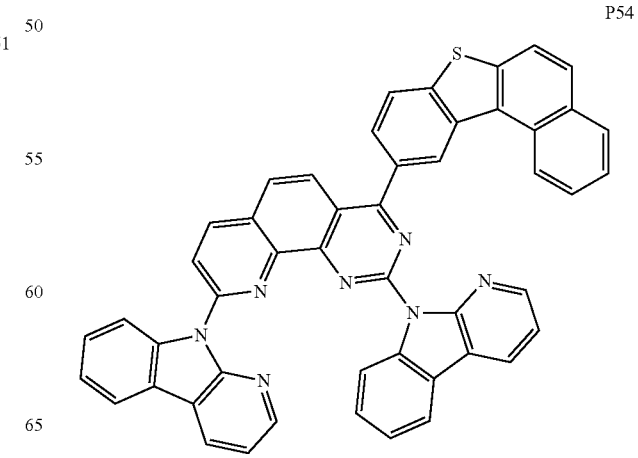

P55
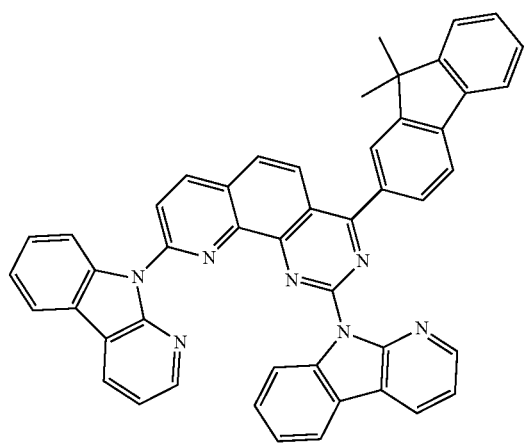
P56
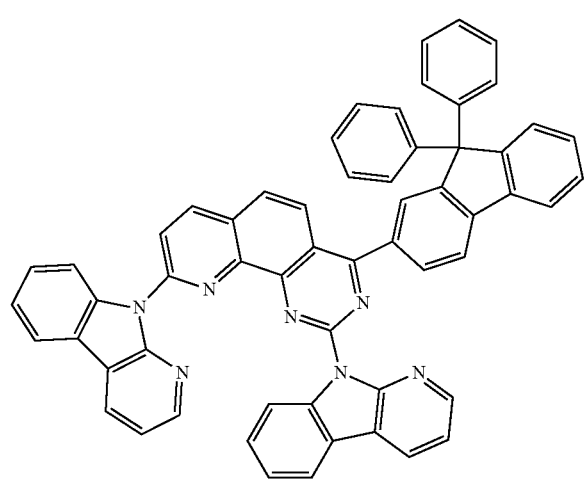
P57
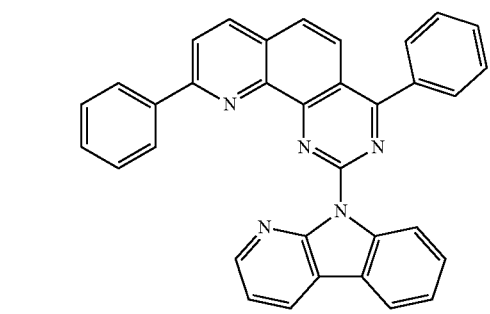
P58
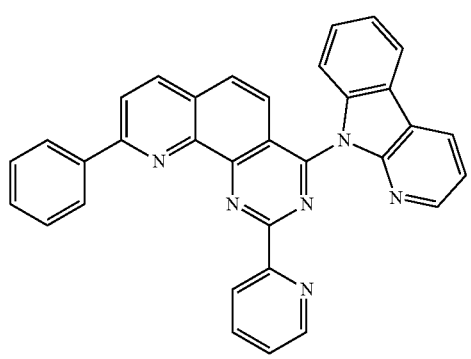
P59
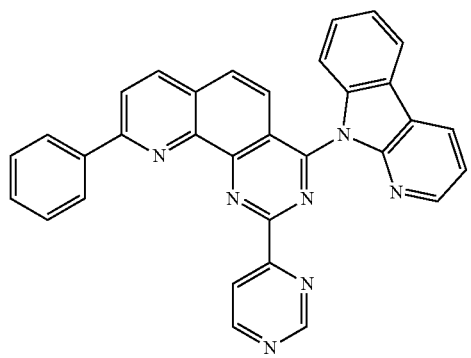
P60
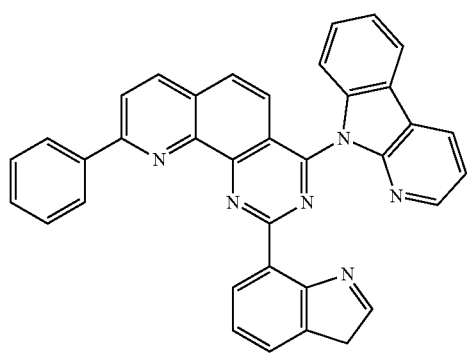
P61
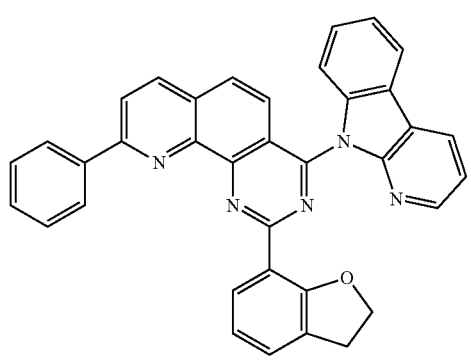
P61
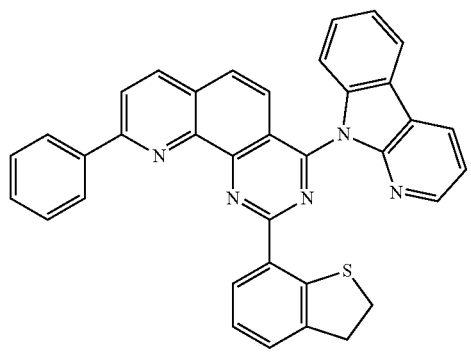

-continued
P63
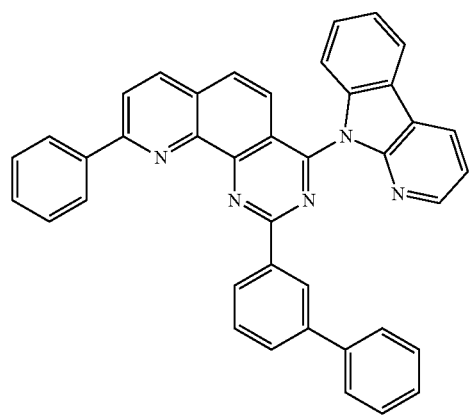
P64
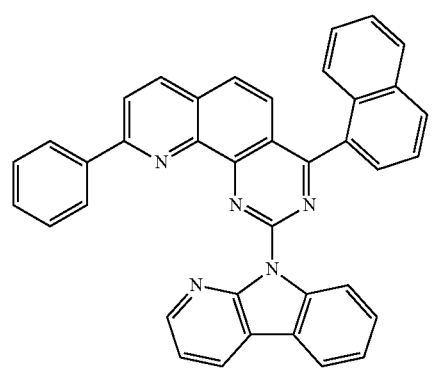
P65
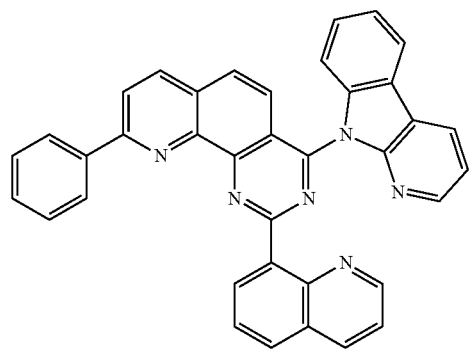
P66
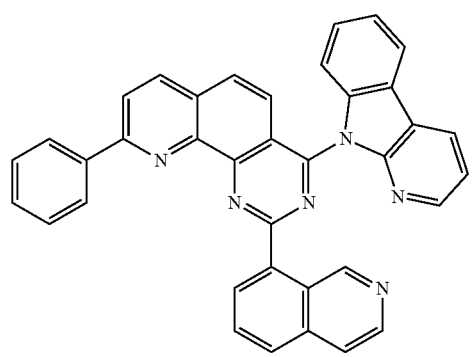
-continued
P67
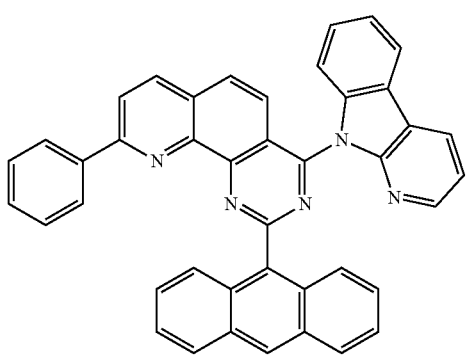
P68
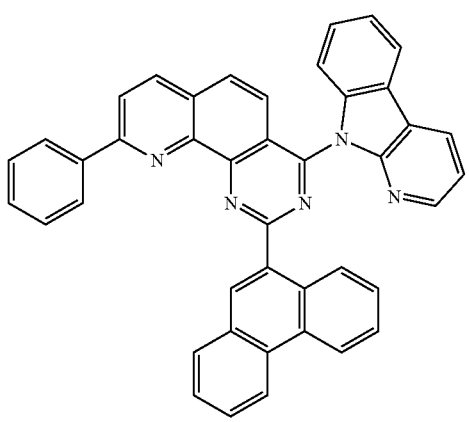
P69
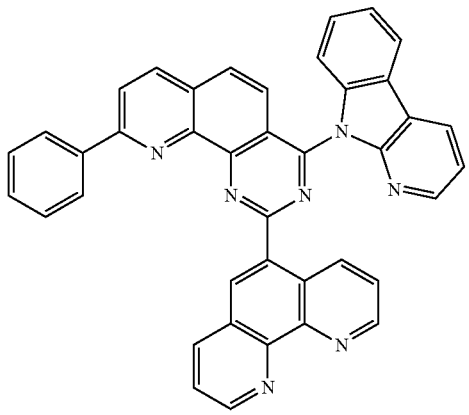
P70
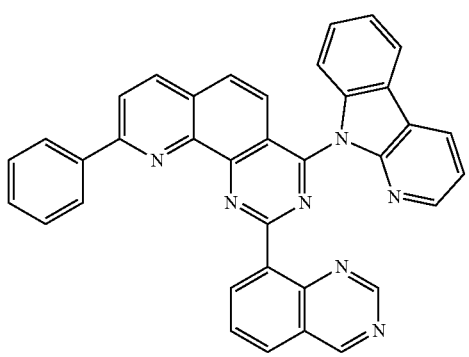

P71
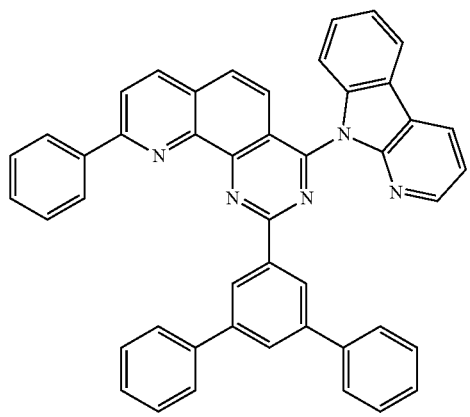
P72
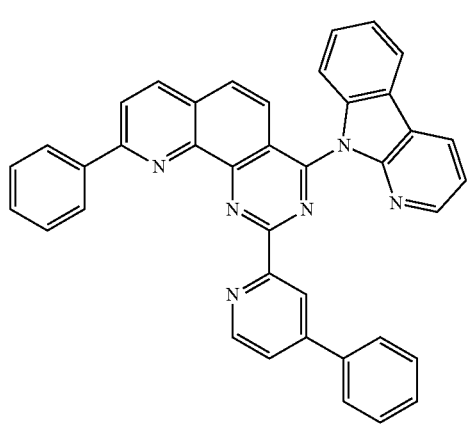
P73
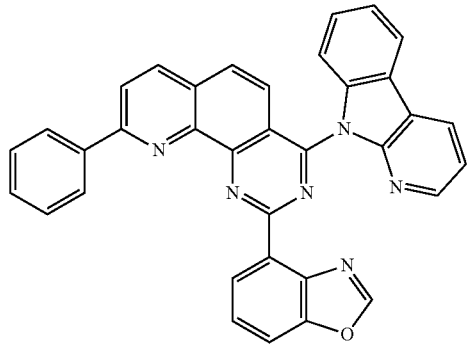
P74
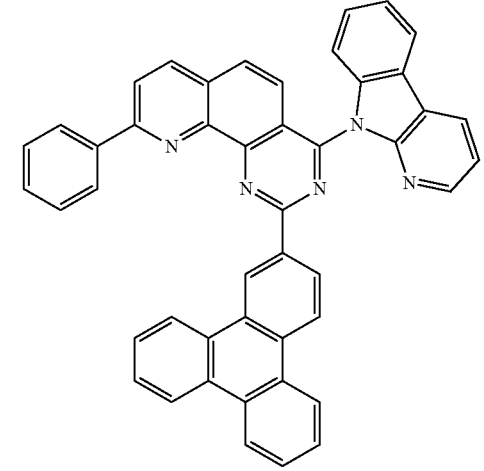
P75
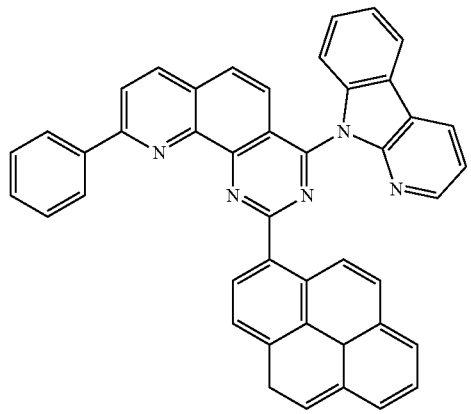
P76
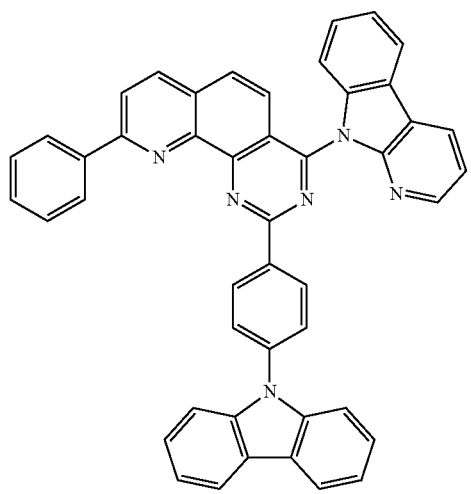
P77
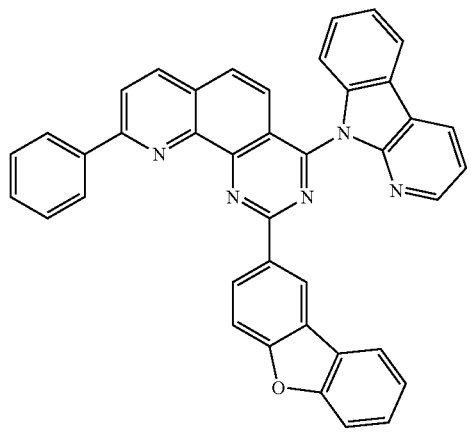

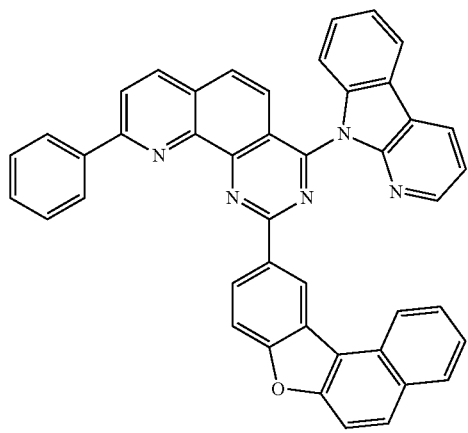
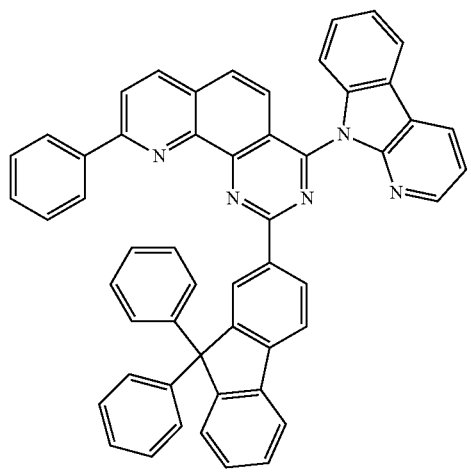

P85 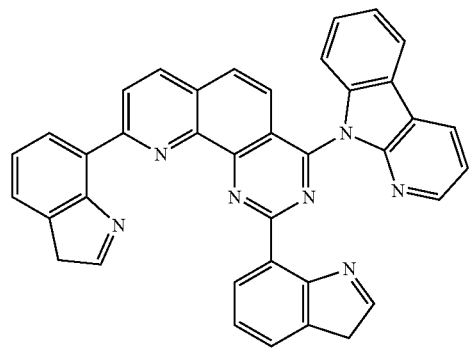
P86 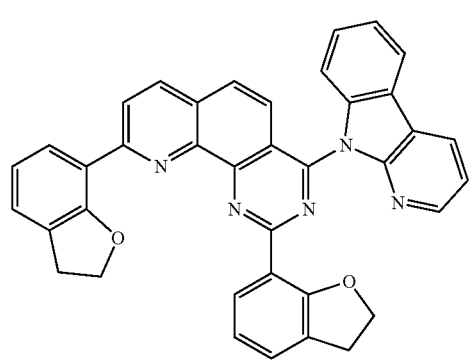
P87 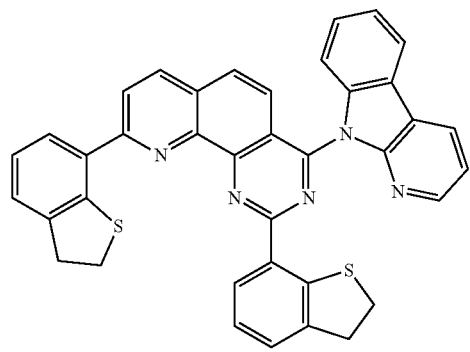
P88 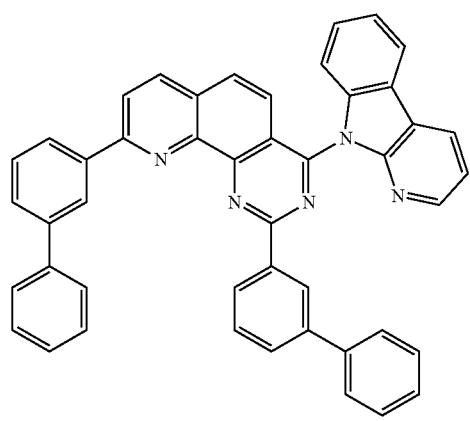
P89 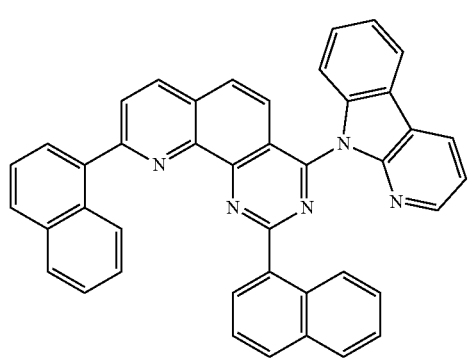
P90 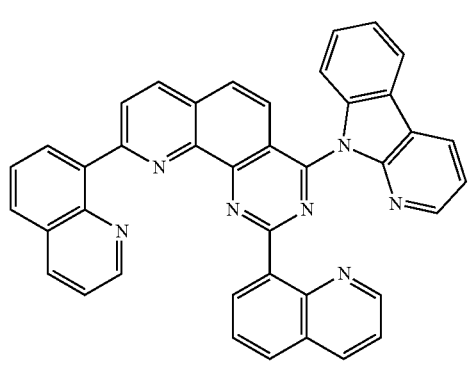
P91 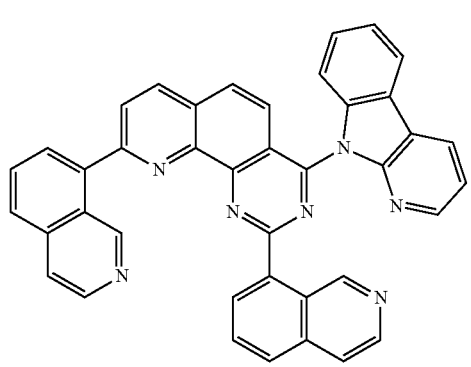
P92 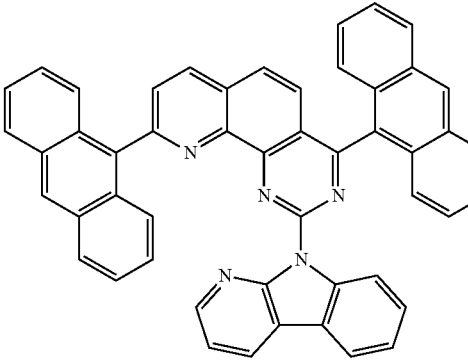

P93 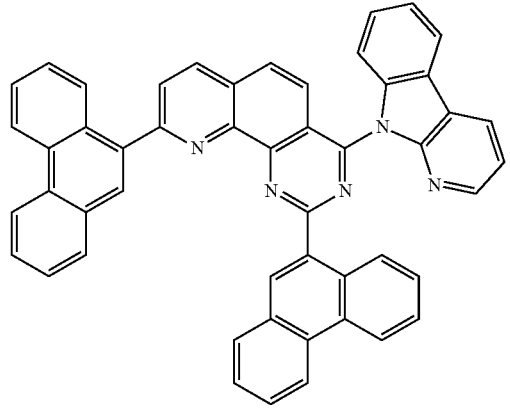
P94 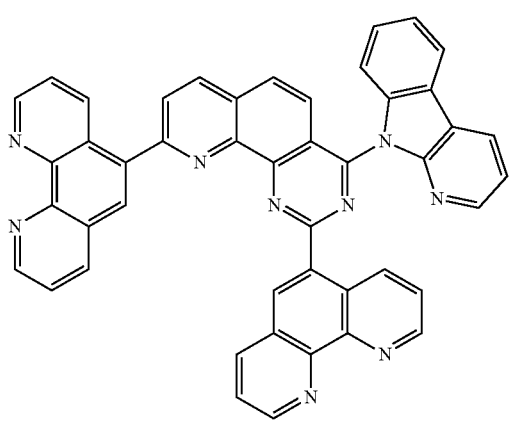
P95 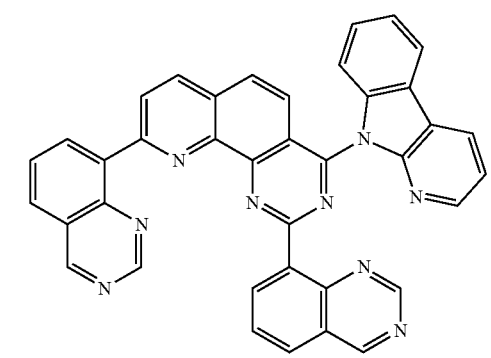
P96 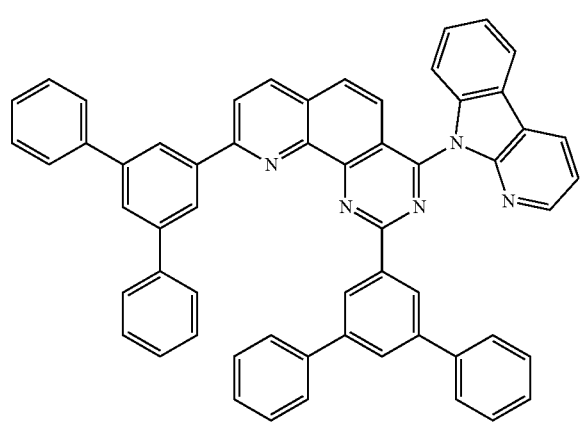
P97 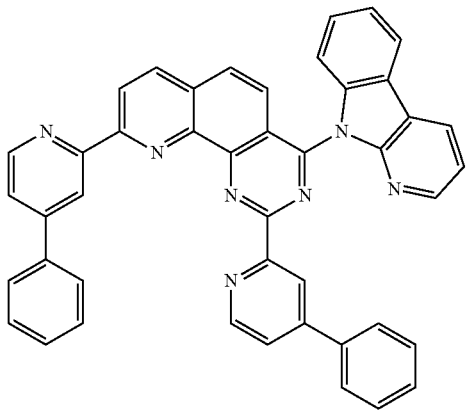
P98 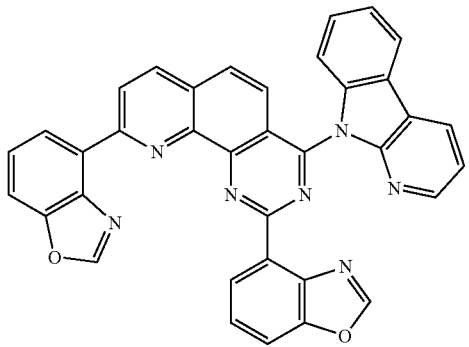
P99 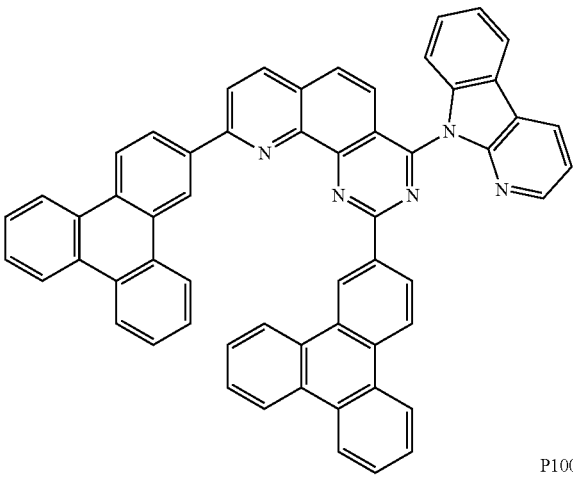
P100 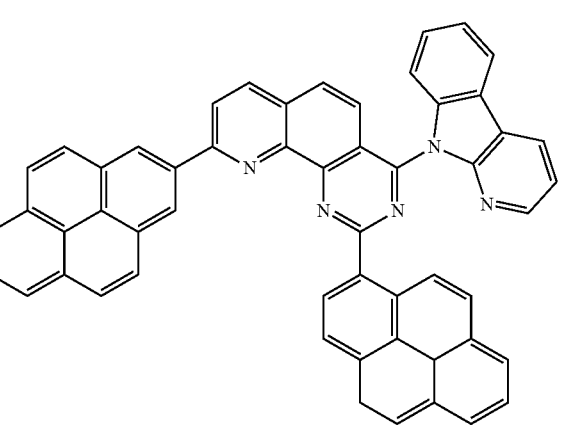

P101
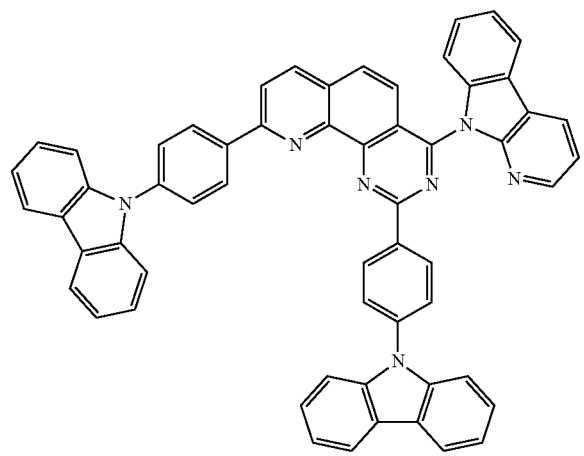
P102
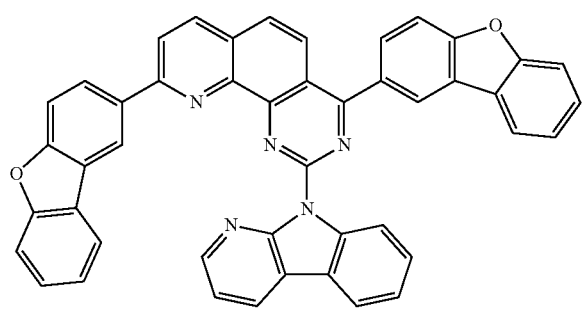
P103
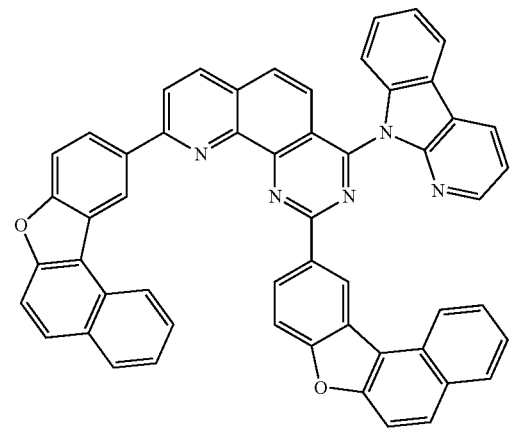
P104
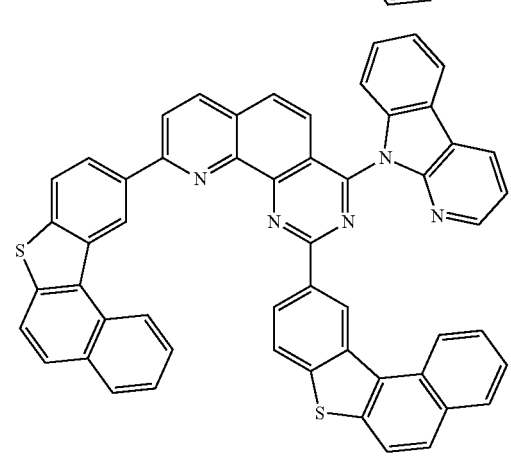
P105
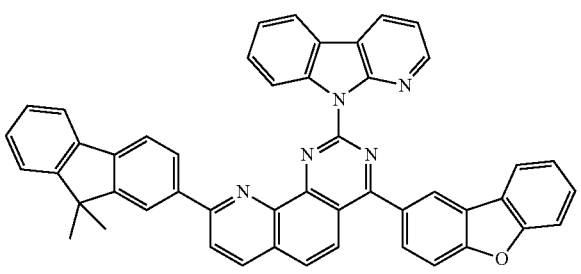
P106
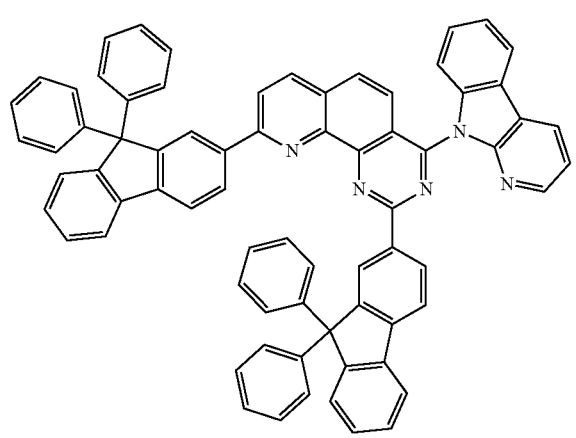
P107
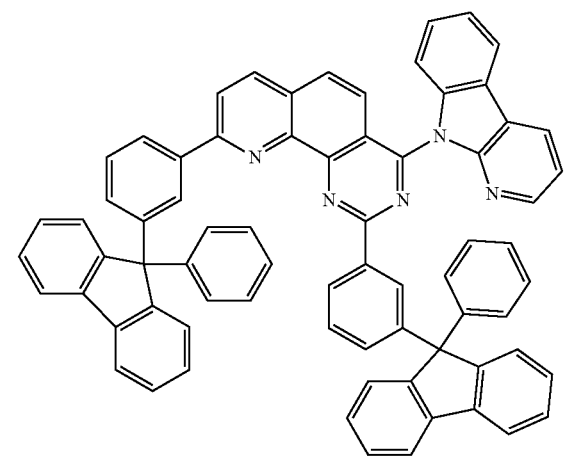

P108

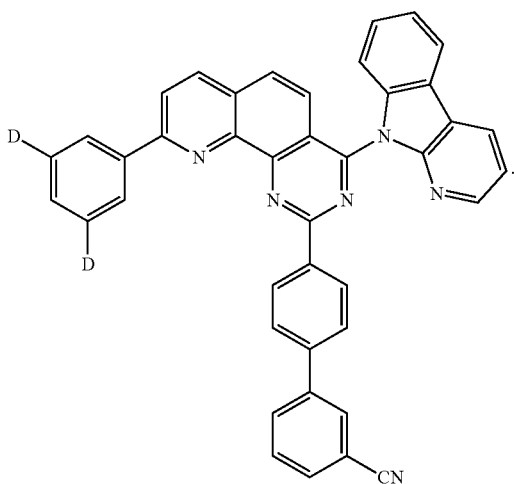

A second aspect of the present disclosure provides a use of the organic compound provided in the first aspect of the present disclosure in an organic electroluminescent device.

According to the present disclosure, the organic compound has superior thermal stability and high glass transition temperature, and can effectively improve the luminous efficiency and service life of an organic electroluminescent device.

In a specific embodiment, the organic compound can be used as an electron transport layer material of an organic electroluminescent device.

A third aspect of the present disclosure provides an organic electroluminescent device comprising an anode, a cathode, and at least one functional layer between the anode and the cathode, wherein the functional layer comprises a hole injection layer, a hole transport layer, an organic electroluminescent layer, an electron transport layer and an electron injection layer, and the electron transport layer contains the organic compound provided in the first aspect of the present disclosure, preferably at least one of Compounds P1 to P108.

For example, as shown in FIG. 1, the organic electroluminescent device comprises an anode 100 and a cathode 200 oppositely arranged, and a functional layer 300 arranged between the anode 100 and the cathode 200; the functional layer 300 contains the compound provided by the present disclosure.

Optionally, the compound provided by the present disclosure can be used to form at least one organic membrane layer in the functional layer 300 to improve the lifespan characteristic and efficiency characteristic and reduce the driving voltage of the organic electroluminescent device.

Optionally, the functional layer 300 comprises an electron transport layer 350 which contains the compound provided by the present disclosure. Wherein the electron transport layer 350 consists of either the compound provided by the present disclosure, or the compound provided by the present disclosure and other materials together.

Optionally, the organic compound provided by the present disclosure can be used for a CGL (charge generation layer) material in a laminate of an organic light-emitting device.

In one embodiment of the present disclosure, as shown in FIG. 1, the organic electroluminescent device may comprise an anode 100, a hole injection layer 310, a hole transport layer 320, an Electron blocking layer 370, an organic electroluminescent layer 330, a Hole blocking layer 340, an electron transport layer 350, an electron injection layer 360 and a cathode 200, which are stacked in turn. The compound provided by the present disclosure can be applied to the electron transport layer 350 of the organic electroluminescent device, and can effectively improve the electron transport characteristic of the organic electroluminescent device.

Optionally, the anode 100 comprises the following anode materials, which are preferably materials with great escape work (work function) that facilitates hole injection into the functional layer. Specific examples of anode materials include, but are not limited to: metals, such as nickel, platinum, vanadium, chromium, copper, zinc and gold or alloys thereof; metal oxides, such as zinc oxide, indium oxide, indium tin oxide (ITO) and indium zinc oxide (IZO); combined metals and oxides, such as ZnO:Al or $SnO_2$:Sb; or conducting polymers, such as poly(3-methylthiophene), poly[3,4-(ethylidene-1,2-dioxyl)thiophene] (PEDT), polypyrrole and polyaniline. Preferably, a transparent electrode with indium tin oxide (ITO) may be adopted as the anode.

Optionally, the organic electroluminescent layer 330 either consists of a single light emitting material, or comprises a host material and a guest material. Optionally, the organic electroluminescent layer 330 consists of a host material and a guest material, the holes injected into the organic electroluminescent layer 330 and the electrons injected into the organic electroluminescent layer 330 can be recombined at the organic electroluminescent layer 330 to form excitons which transfer energy to the host material, and the host material transfers energy to the guest material, so that the guest material can emit light.

The host material of the organic electroluminescent layer 330 may be a metal chelate compound, a diphenyl-vinyl derivative, an aromatic amine derivative, a dibenzofuran derivative or other types of materials, which is not specially restricted in the present disclosure. In one embodiment of the present disclosure, the host material of the organic electroluminescent layer 330 may be CBP. In another embodiment of the present disclosure, the host material of the organic electroluminescent layer 330 may be α,β-ADN.

The guest material of the organic electroluminescent layer 330 may be a compound with a condensed aryl ring or a derivative thereof, a compound with a heteroaryl ring or a derivative thereof, an aromatic amine derivative or other materials, which is not specially restricted in the present disclosure. In one embodiment of the present disclosure, the guest material of the organic electroluminescent layer 330 may be $Ir(piq)_2(acac)$. In another embodiment of the present disclosure, the guest material of the organic electroluminescent layer 330 may be BD-1.

The electron transport layer 350 is either a single-layer structure or a multi-layer structure, the electron transport layer 350 may comprise one or more electron transport materials, the electron transport material may be selected from benzimidazole derivatives, oxadiazole derivatives, quinoxaline derivatives or other electron transport materials, which is not specially restricted in the present disclosure. For example, in one embodiment of the present disclosure, the electron transport layer 350 may consist of DBimiBphen, LiQ and the organic compound of the present disclosure.

Optionally, the cathode 200 comprises the following cathode materials, which are materials with small escape work that facilitates electron injection into the functional layer. Specific examples of cathode materials include, but are not limited to: metals, such as magnesium, calcium, sodium, potassium, titanium, indium, yttrium, lithium, gadolinium, aluminum, silver, tin and lead or alloys thereof; or multi-layer materials, such as LiF/Al, Liq/Al, LiO$_2$/Al, LiF/Ca, LiF/Al and BaF$_2$/Ca. Preferably, a Al-containing metal electrode may be adopted as a cathode.

Optionally, as shown in FIG. 1, a hole injection layer 310 may also be arranged between the anode 100 and the hole transport layer 320 to enhance the capability of injecting holes into the hole transport layer 320. Benzidine derivatives, starburst arylamine compounds, phthalocyanine derivatives or other materials are options for the hole injection layer 310, which is not specially restricted in the present disclosure. In one embodiment of the present disclosure, the hole injection layer 310 may consist of m-MTDATA.

Optionally, as shown in FIG. 1, an electron blocking layer 370 may also be arranged between the hole transport layer 320 and the organic electroluminescent layer 330. The electron blocking layer 370 may comprise either inorganic materials such as alkali sulfides and alkali halides, or a complex of alkali metal and organic substances. In one embodiment of the present disclosure, the electron blocking layer 370 may comprise LiQ.

Based on the excellent characteristics of the organic compound of the present disclosure, the organic electroluminescent device of the present disclosure has high luminous efficiency and long service life.

The present disclosure will be further described below through examples without any restriction thereby.

All the compounds of the synthesis methods not mentioned herein are commercially available raw material products.

An ICP-7700 mass spectrometer and an M5000 elemental analyzer were used for analysis and detection of Intermediates and Compounds in the present disclosure.

Synthesis Examples

The organic compound of the present disclosure can be prepared through the following steps:

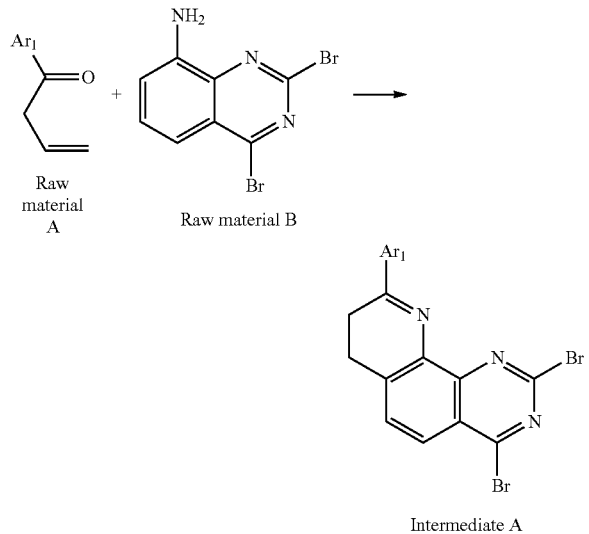

(1) 0.15 mol of Raw material A, 0.1 mol of Raw material B, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that a crude Intermediate A was obtained.

(2) The crude Intermediate A obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain a purified Intermediate A.

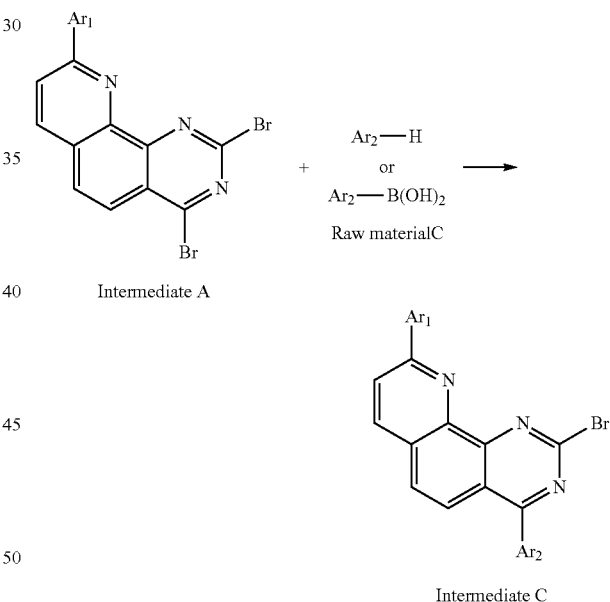

(3) 0.08 mol of purified Intermediate A obtained above was added into the reaction flask, 0.08 mol of Raw material C, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75-80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C was obtained; the crude Intermediate C was recrystallized with toluene to obtain a pure Intermediate C.

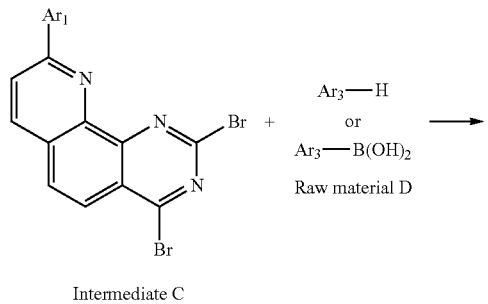

Intermediate C

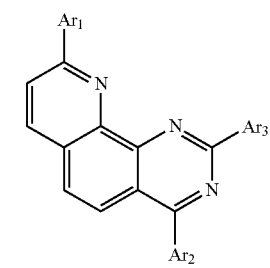

Compound X (4) 0.06 mol of Intermediate C obtained above was added into the reaction flask, 0.06 mol of Raw material D, 0.006 mol of cuprous bromide, 0.0006 mol of 1,10-phenanthroline, 0.12 mol of potassium carbonate and 500 mL of dimethylbenzene were added under the protection of nitrogen, heated to 13~135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude compound was obtained; the crude compound was passed through a silica gel column through ethyl acetate and petroleum ether to obtain a pure Compound X.

The synthesis method of the organic compound of the present disclosure is specified below in combination with synthesis examples 1 to 10.

The synthesis process of Raw material A1 is as follows:

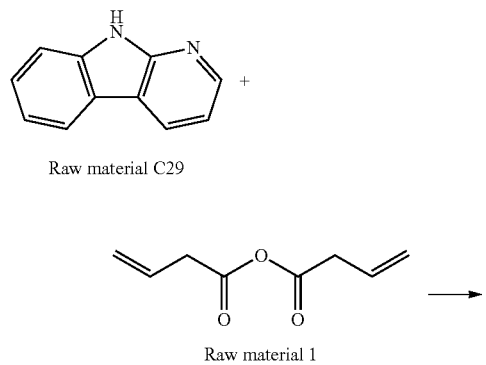

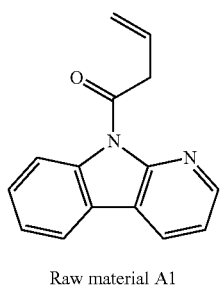

Raw material A1

0.15 mol of Raw material C29 (CAS No.: 244-76-8), 0.15 mol of Raw material 1 (CAS:78957-07-0) and 300 mL of dichloromethane were added to a reaction flask, 0.015 mol of concentrated sulfuric acid was added at 40° C. while stirring for a reaction which stopped after 6 h, 500 mL of water was added into the reaction solution and kept still for 5 min, then the solution was dispensed, the aqueous phase was extracted with 200 mL/time of dichloromethane for 3 times, organic phases were combined, washed with 200 mL/time of water for 3 times, dried with anhydrous magnesium sulfate, concentrated to dry, and recrystallized with petroleum ether, so that 30.48 g of pure Raw material A1 with a yield of 86% was obtained. m/z=237.08[M+H]$^+$.

The synthesis process of Raw material B1 is as follows:

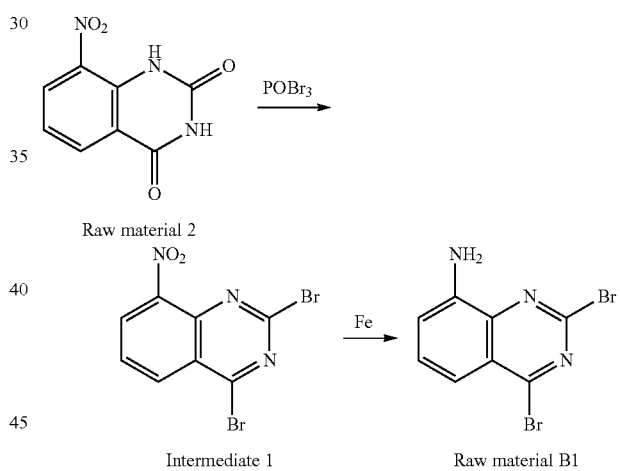

0.2 mol of Raw material 2 (CAS: 174565-61-8) and 400 mL of toluene were added to a reaction flask, stirred and dissolved for clarification, then 0.23 mol of phosphoryl bromide was added, heated to 110° C. for a return flow reaction for 72 h, the reaction solution was cooled to room temperature, slowly added to ice water, filtered and dried, the obtained crude solid was recrystallized with dichloroethane to obtain 56.6 g of pure Intermediate 1 with a yield of 85%.

36.79 g of Intermediate 1 obtained was added to the reaction flask, 600 mL of toluene and 0.17 mol of iron powder were added, then the solution was heated to 80° C., 0.17 mol of concentrated hydrochloric acid was added dropwise, then stirred for a reaction for 30 h and filtered, 300 mL of water was added to filtrate, kept still for 5 min and dispensed, the aqueous phase was extracted with 200 mL/time of toluene for 3 times, organic phases were combined, washed with 300 mL/time of water for 3 times, dried with anhydrous magnesium sulfate, the organic phase was concentrated to dry, so that 31.66 g of relatively pure Raw material B1 with a yield of 95% was obtained. m/z=301.96 [M+H]⁺.

Synthesis Example 1, Synthesis of Compound P1

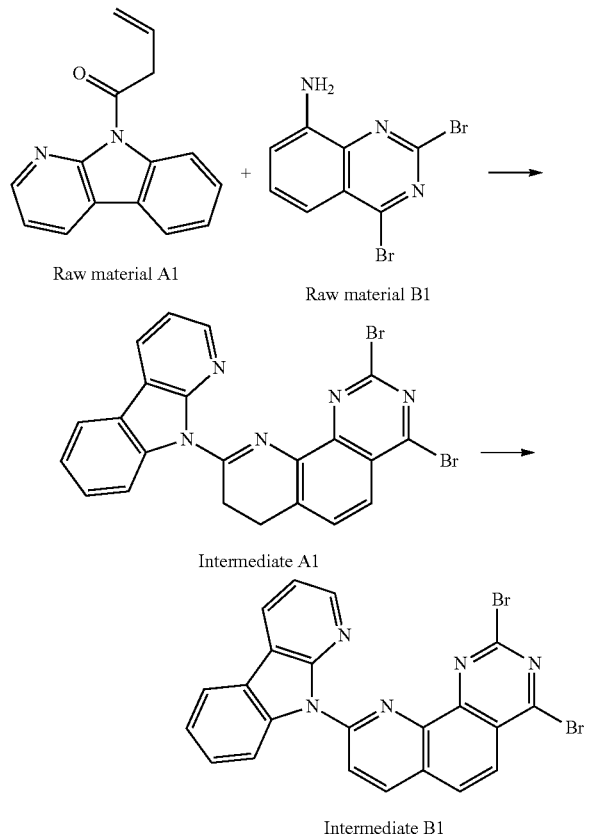

Raw material A1

Raw material B1

Intermediate A1

Intermediate B1

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of Intermediate B1 with a yield of 84.21%.

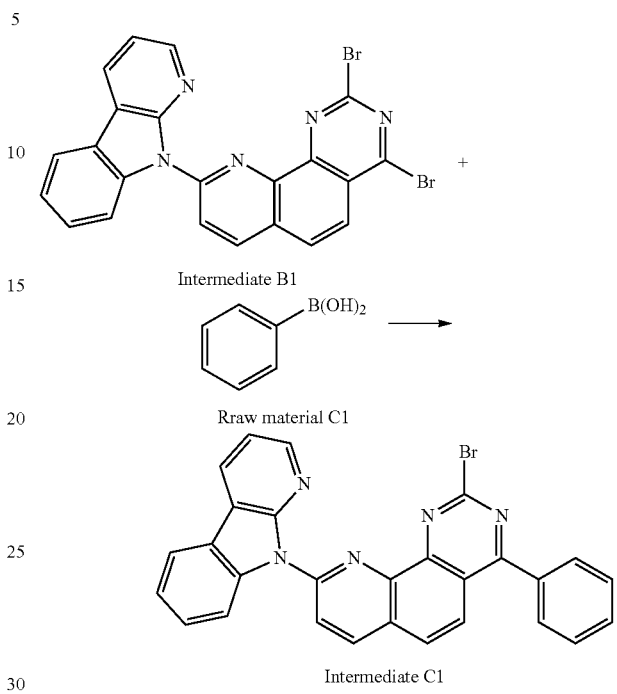

Intermediate B1

Rraw material C1

Intermediate C1

(3) 0.08 mol of Intermediate B1 obtained above was added into the reaction flask, 0.08 mol of Raw material C1, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C1 was obtained; the crude Intermediate Cl was recrystallized with toluene to obtain 30.14 g of pure Intermediate C1 with a yield of 75%.

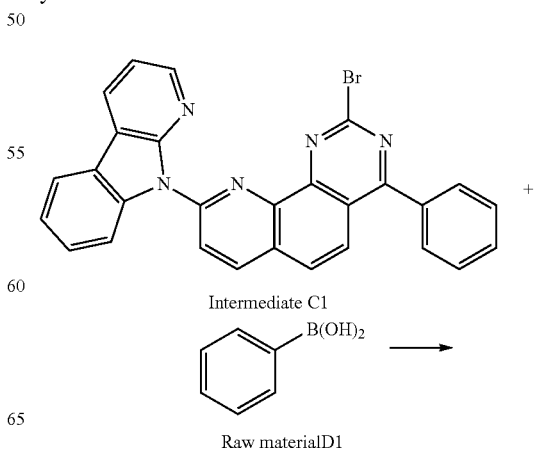

Intermediate C1

Raw materialD1

-continued

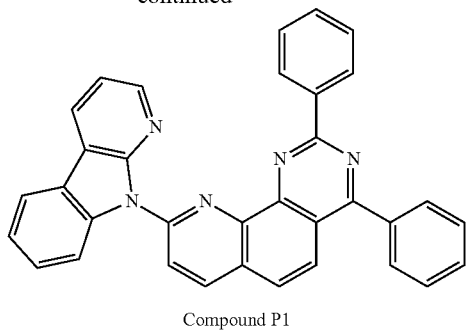

Compound P1

(4) 0.06 mol of Intermediate C1 obtained above was added into the reaction flask, 0.06 mol of Raw material D1, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P1 was obtained; the crude Compound P1 was passed through a silica gel column through ethyl acetate and petroleum ether to obtain 24.88 g of pure Compound P1 with a yield of 83.02%. m/z=500.58 [M+H]+.

Synthesis Example 2, Synthesis of Compound P2

(1) 0.15 mol of Raw material A1, 0.1 mol of Raw material B1, 300 mL of toluene and 1 mol of concentrated sulfuric acid were added to a reaction flask, and stirred for a reaction at 25-30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50-60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

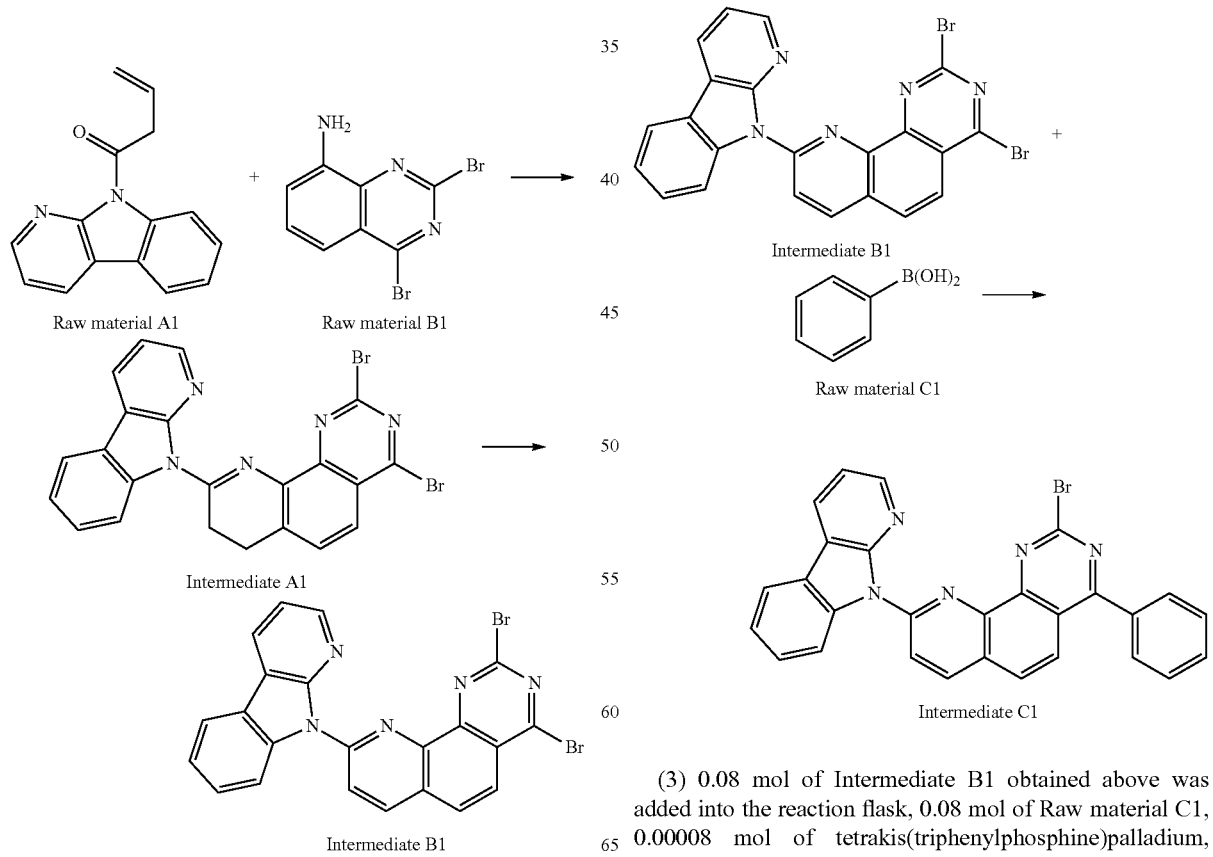

(3) 0.08 mol of Intermediate B1 obtained above was added into the reaction flask, 0.08 mol of Raw material C1, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75-80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C1 was obtained; the crude Intermediate C1 was recrystallized with toluene to obtain 30.14 g of pure Intermediate C1 with a yield of 75%.

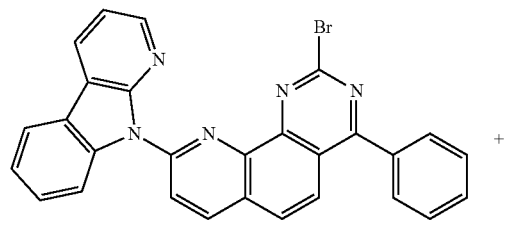

Intermediate C1

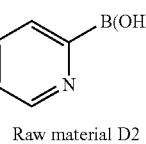

Raw material D2

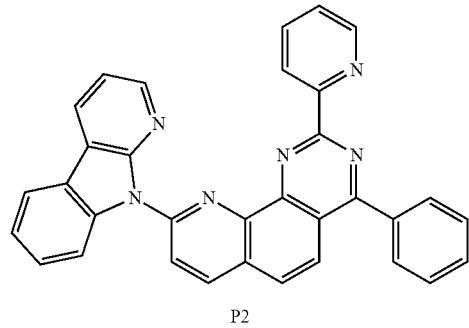

P2

(4) 0.06 mol of Intermediate C1 obtained above was added into the reaction flask, 0.06 mol of Raw material D2, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude compound was obtained; the crude compound was passed through a silica gel column through ethyl acetate and petroleum ether to obtain 24.93 g of pure Compound P2 with a yield of 83%. m/z=502.19[M+H]+.

Synthesis Example 3, Synthesis of Compound P9

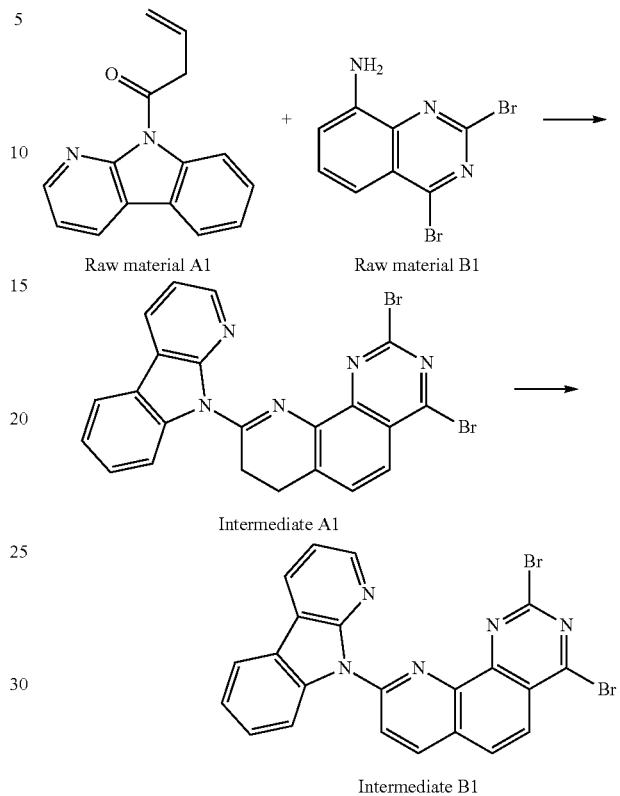

(1) 0.15 mol of Raw material A1, 0.1 mol of Raw material B1, 300 mL of toluene and 1 mol of concentrated sulfuric acid were added to a reaction flask, and stirred for a reaction at 25-30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

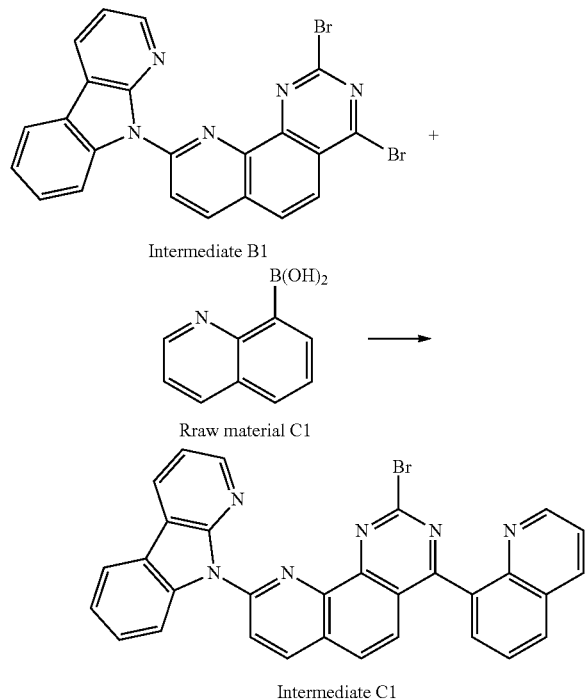

Intermediate B1

Raw material C1

Intermediate C1

(3) 0.08 mol of Intermediate B1 obtained above was added into the reaction flask, 0.08 mol of Raw material C1, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C1 was obtained; the crude Intermediate C1 was recrystallized with toluene to obtain 30.14 g of pure Intermediate C1 with a yield of 75%.

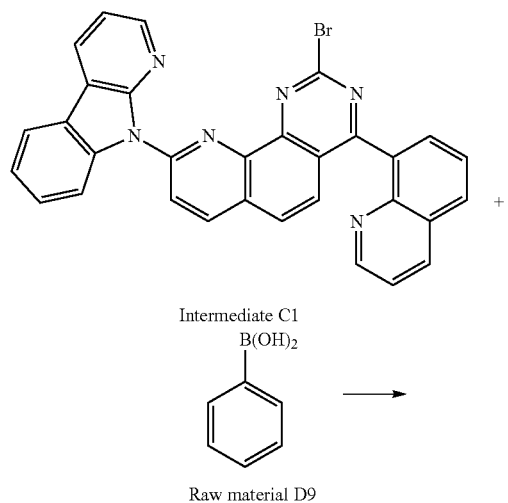

Intermediate C1

Raw material D9

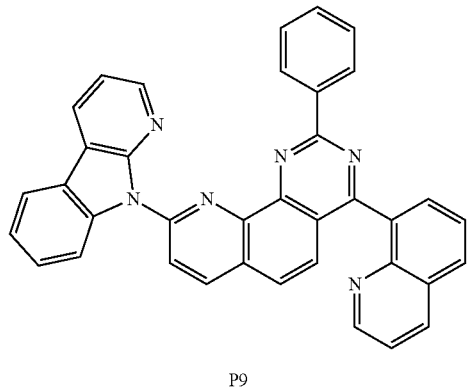

P9

(4) 0.06 mol of Intermediate C1 obtained above was added into the reaction flask, 0.06 mol of Raw material D9, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P9 was obtained; the crude Compound P9 was passed through a silica gel column through ethyl acetate and petroleum ether to obtain 27.46 g of pure Compound P9 with a yield of 83.11%. m/z=551.19 [M+H]⁺.

Synthesis Example 4, Synthesis of Compound P11

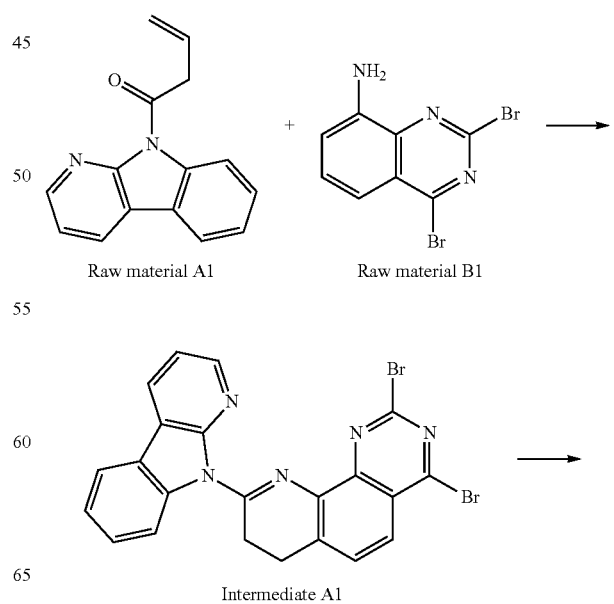

Raw material A1

Raw material B1

Intermediate A1

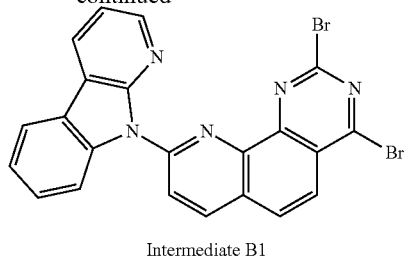

Intermediate B1

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of Intermediate B1 with a yield of 84.21%.

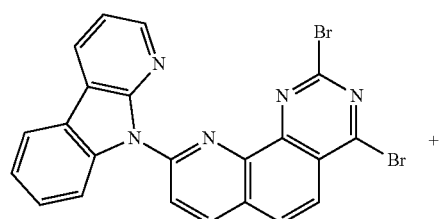

Intermediate B1

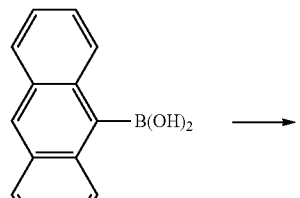

Raw material C11

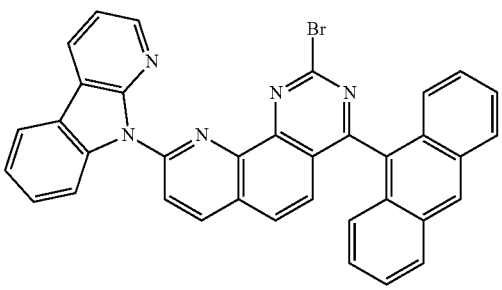

Intermediate C11

(3) 0.08 mol of Intermediate B1 obtained above was added into the reaction flask, 0.08 mol of Raw material C11, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C1 was obtained; the crude Intermediate C11 was recrystallized with toluene to obtain 35.186 g of pure Intermediate C11 with a yield of 73%.

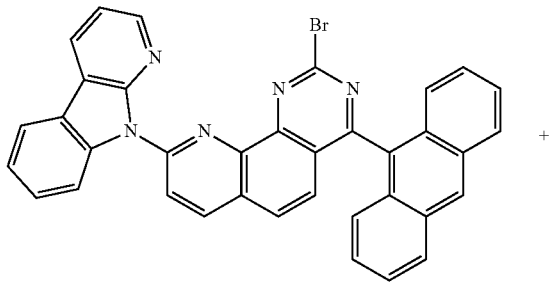

Intermediate C11

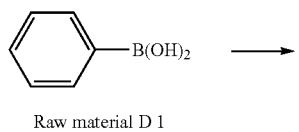

Raw material D 1

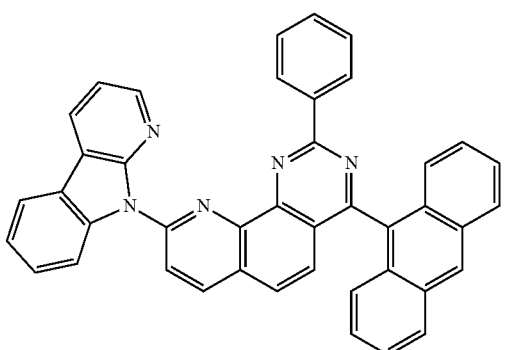

P11

(4) 0.0584 mol of Intermediate C11 obtained above was added into the reaction flask, 0.08 mol of Raw material D1, 0.00008 mol of tetrakis(triphenylphosphine)palladium, 0.006 mol of tetrabutylammonium bromide, 0.117 mol of potassium carbonate, 400 mL of toluene, 150 mL of ethanol and 150 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P11 was obtained; the crude Compound P11 was recrystallized with toluene to obtain 26.6 g of pure Compound P11 with a yield of 76%. m/z=600.18[M+H]$^+$.

Synthesis Example 5, Synthesis of Compound P12

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of Intermediate B1 with a yield of 84.21%.

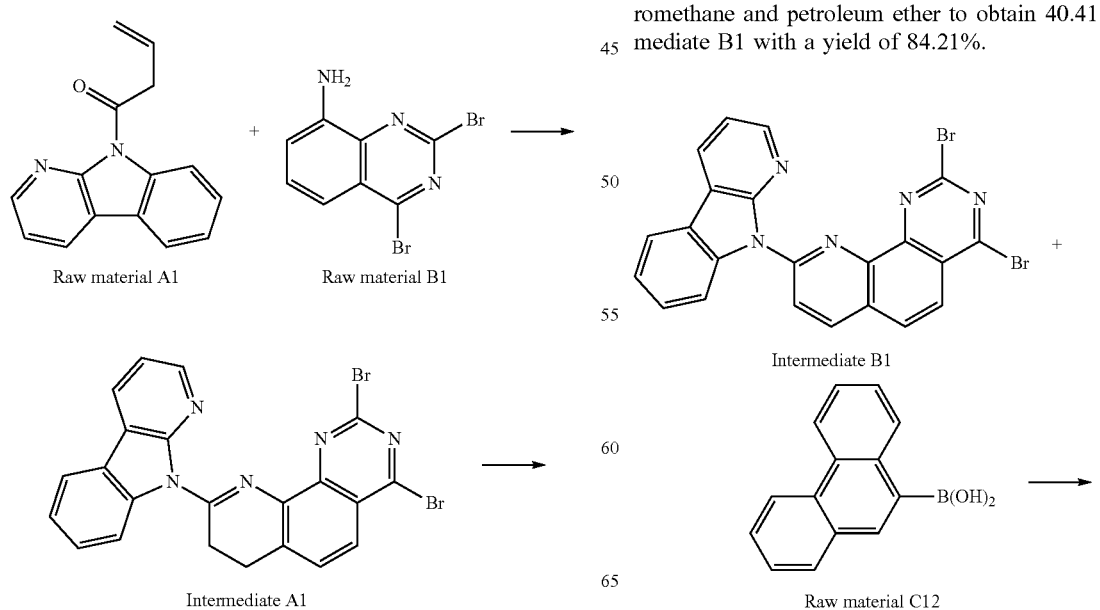

-continued

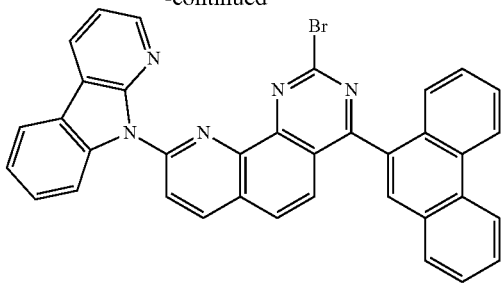

Intermediate C12

(3) 0.08 mol of Intermediate B1 obtained above was added into the reaction flask, 0.08 mol of Raw material C12, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C12 was obtained; the crude Intermediate C12 was recrystallized with toluene to obtain 36.15 g of pure Intermediate C12 with a yield of 75%.

(4) 0.06 mol of Intermediate C12 obtained above was added into the reaction flask, 0.06 mol of Raw material D1, 0.00006 mol of tetrakis(triphenylphosphine)palladium, 0.006 mol of tetrabutylammonium bromide, 0.12 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P12 was obtained; the crude Compound P12 was recrystallized with toluene to obtain 28.79 g of pure Compound P12 with a yield of 80%. m/z=600.18[M+H]$^+$.

Synthesis Example 6, Synthesis of Compound P21

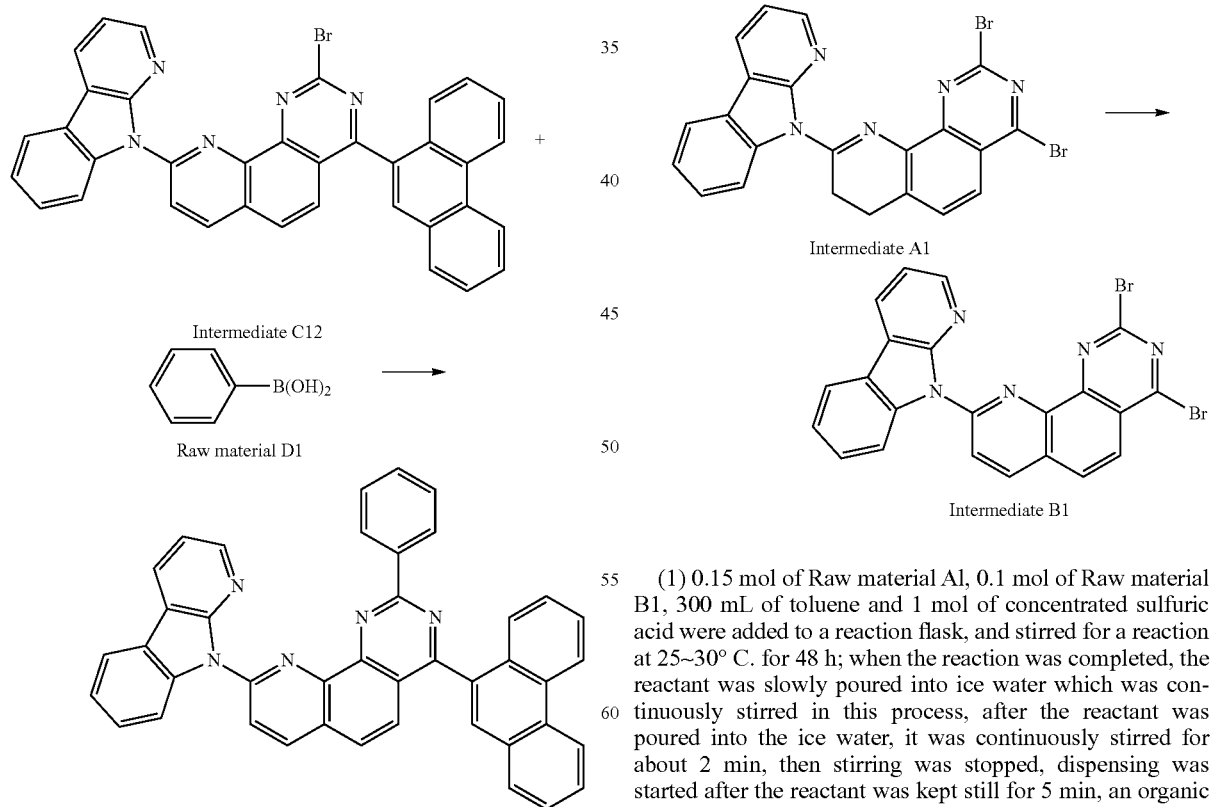

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50-60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

Intermediate B1

Raw material C21

Intermediate C21

(3) 0.08 mol of Intermediate B1 obtained above was added into the reaction flask, 0.08 mol of Raw material C21 (CAS No.: 86-74-8), 0.008 mol of cuprous bromide, 0.0008 mol of 1,10-phenanthroline, 0.16 mol of potassium carbonate and 500 mL of dimethylbenzene were added under the protection of nitrogen, heated to 130~135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Intermediate C21 was obtained; the crude Compound C21 was passed through a silica gel column through ethyl acetate and petroleum ether to obtain 34.07 g of pure Intermediate C21 with a yield of 72%.

Intermediate C21

Raw material D1

P21

(4) 0.058 mol of Intermediate C21 obtained above was added into the reaction flask, 0.06 mol of Raw material D1, 0.00006 mol of tetrakis(triphenylphosphine)palladium, 0.006 mol of tetrabutylammonium bromide, 0.12 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P21 was obtained; the crude Intermediate P21 was recrystallized with toluene to obtain 27.31 g of pure Compound P21 with a yield of 80.0%. m/z=589.22[M+H]$^+$.

Synthesis Example 7, Synthesis of Compound P24

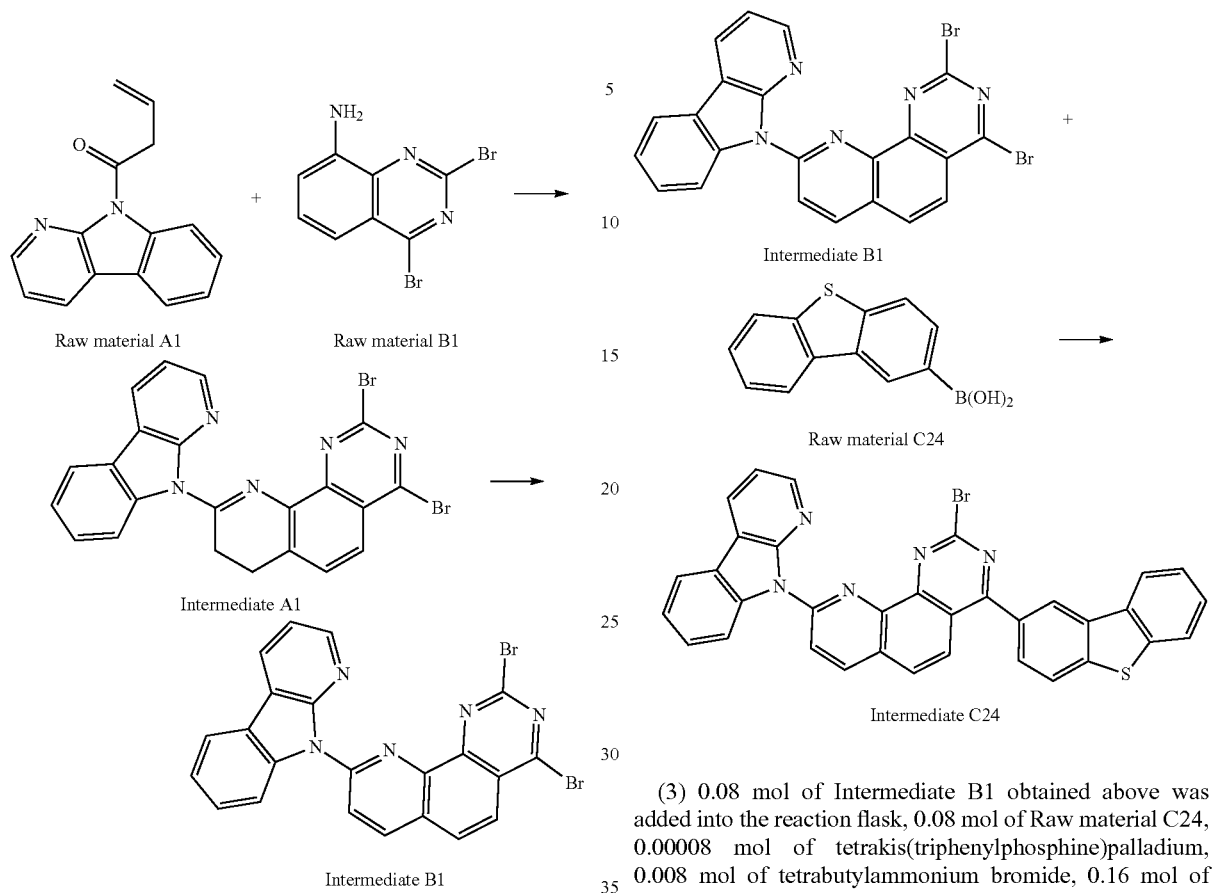

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of Intermediate B1 with a yield of 84.21%.

(3) 0.08 mol of Intermediate B1 obtained above was added into the reaction flask, 0.08 mol of Raw material C24, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C24 was obtained; the crude Intermediate C24 was recrystallized with toluene to obtain 34.32 g of pure Intermediate C24 with a yield of 70.5%.

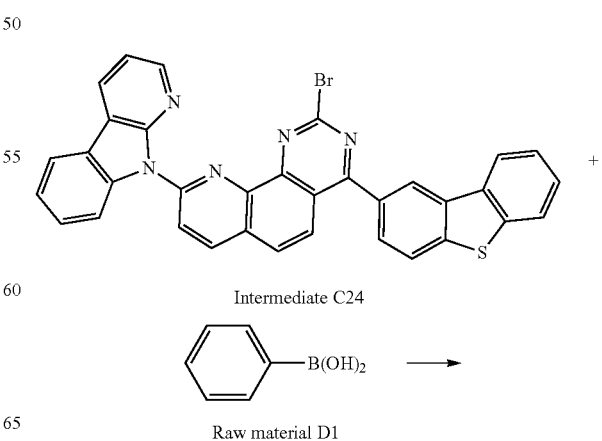

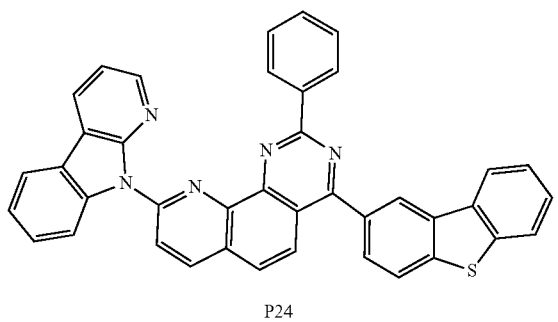

P24

(4) 0.056 mol of Intermediate C24 obtained above was added into the reaction flask, 0.06 mol of Raw material D1, 0.00006 mol of tetrakis(triphenylphosphine)palladium, 0.006 mol of tetrabutylammonium bromide, 0.12 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P24 was obtained; the crude Intermediate P24 was recrystallized with toluene to obtain 27.48 g of pure Compound P24 with a yield of 81.0%. m/z=606.18[M+H]$^+$.

Synthesis Example 8, Synthesis of Compound P29

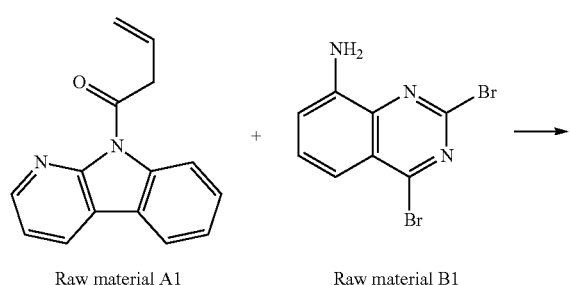

Raw material A1       Raw material B1

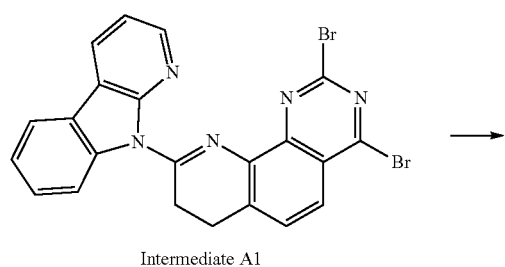

Intermediate A1

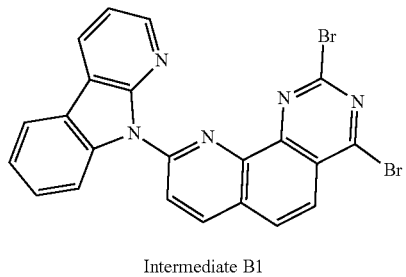

Intermediate B1

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate Al with a yield of 95% was obtained.

(2) 47.99 g of Intermediate Al obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

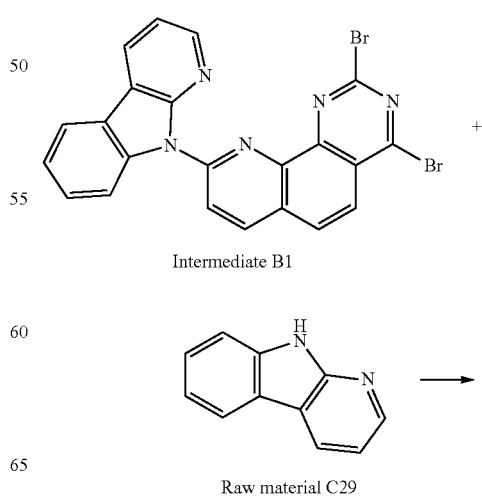

Intermediate B1

Raw material C29

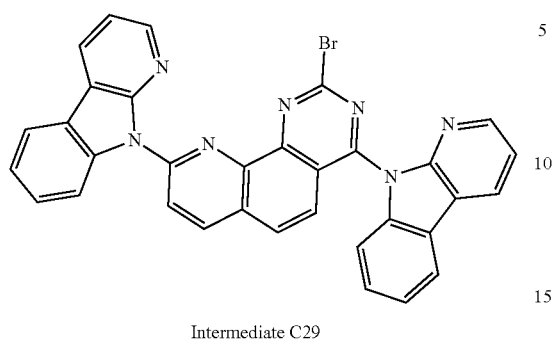

Intermediate C29

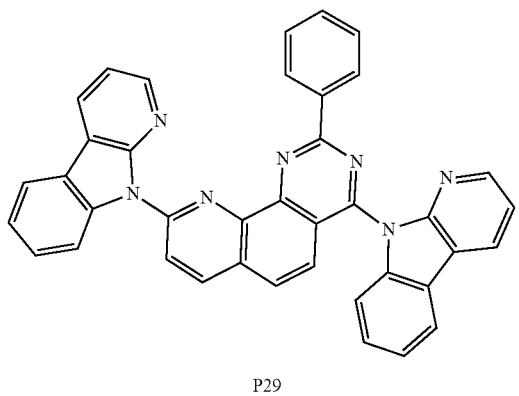

P29

(3) 0.08 mol of Intermediate B1 obtained above was added into the reaction flask, 0.06 mol of Raw material C29 (CAS No.: 244-76-8), 0.008 mol of cuprous bromide, 0.0008 mol of 1,10-phenanthroline, 0.16 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Intermediate C29 was obtained; the crude Compound C29 was passed through a silica gel column through ethyl acetate and petroleum ether to obtain 30.14 g of pure Intermediate C29 with a yield of 75%.

(4) 0.06 mol of Intermediate C29 obtained above was added into the reaction flask, 0.08 mol of Raw material D1, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P29 was obtained; the crude Intermediate P29 was recrystallized with toluene to obtain 29.01 g of pure Compound P29 with a yield of 82.01%. m/z=591.22[M+H]+.

Synthesis Example 9, Synthesis of Compound P34

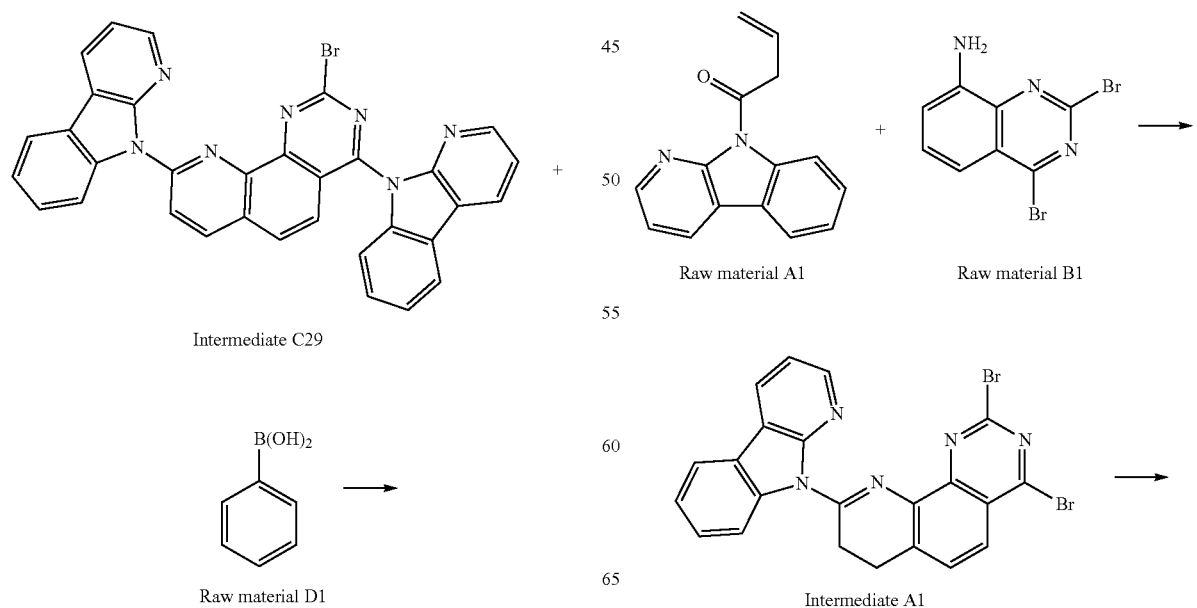

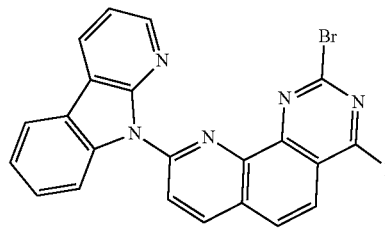

Intermediate B1

(1) 0.15 mol of Raw material A1, 0.1 mol of Raw material B1, 300 mL of toluene and 1 mol of concentrated sulfuric acid were added to a reaction flask, and stirred for a reaction at 25-30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate Al with a yield of 95% was obtained.

(2) 47.99 g of Intermediate Al obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

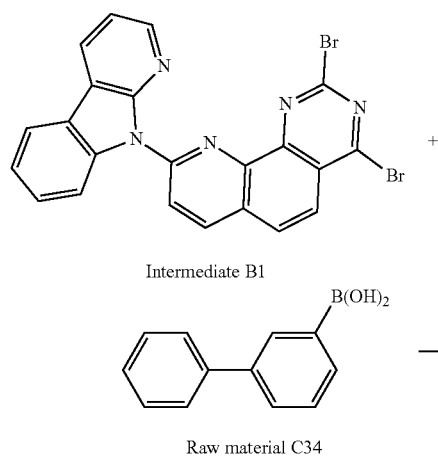

Intermediate B1

Raw material C34

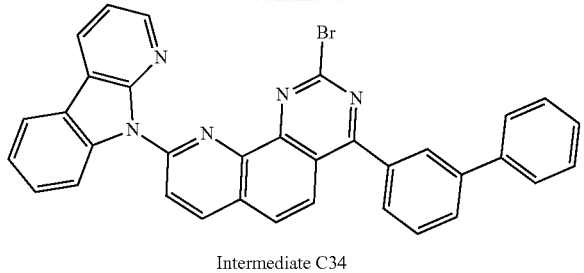

Intermediate C34

(3) 0.08 mol of Intermediate B1 obtained above was added into the reaction flask, 0.08 mol of Raw material C34, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C34 was obtained; the crude Intermediate C34 was recrystallized with toluene to obtain 34.71 g of pure Intermediate C34 with a yield of 75%.

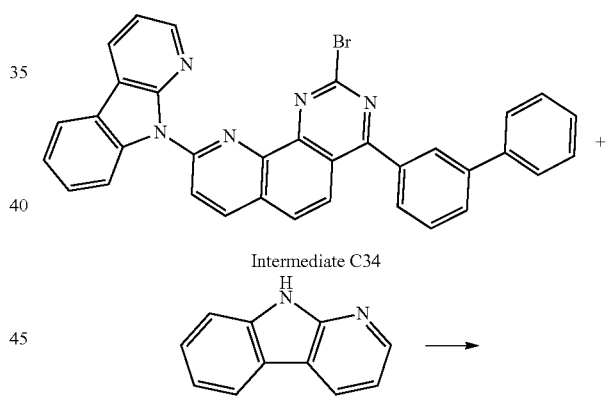

Intermediate C34

Raw material C29

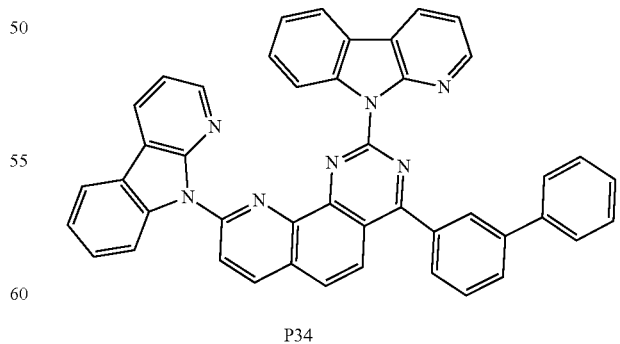

P34

(4) 0.06 mol of Intermediate C34 obtained above was added into the reaction flask, 0.06 mol of Raw material C29 (CAS No.: 244-76-8), 0.006 mol of cuprous bromide, 0.0006 mol of 1,10-phenanthroline, 0.12 mol of potassium carbonate and 500 mL of dimethylbenzene were added under the protection of nitrogen, heated to 130~135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P34 was obtained; the crude Compound P34 was passed through a silica gel column through ethyl acetate and petroleum ether to obtain 25.91 g of pure Compound P34 with a yield of 75%. m/z=576.18[M+H]$^+$.

Synthesis Example 10, Synthesis of Compound P35

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

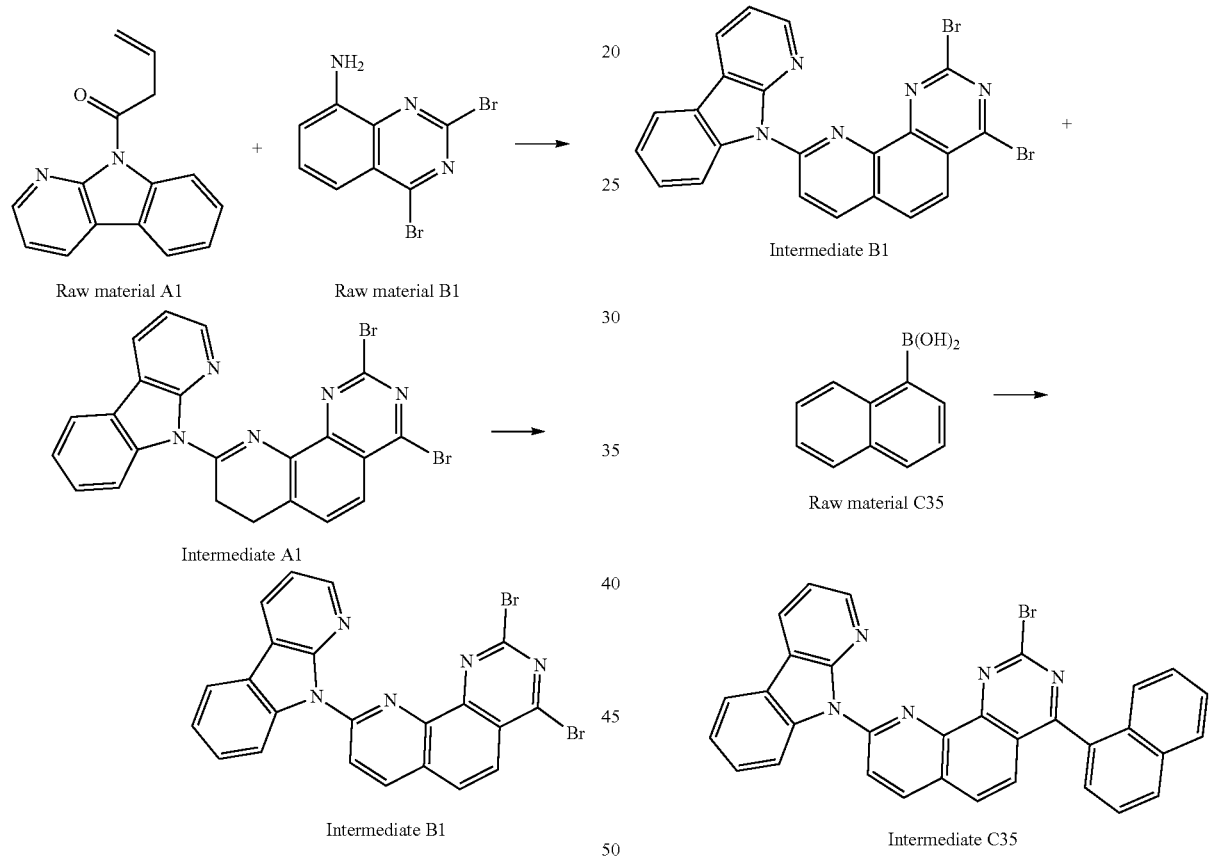

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(3) 0.08 mol of Intermediate B1 obtained above was added into the reaction flask, 0.08 mol of Raw material C35, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C35 was obtained; the crude Intermediate C35 was recrystallized with toluene to obtain 33.14 g of pure Intermediate C35 with a yield of 75%.

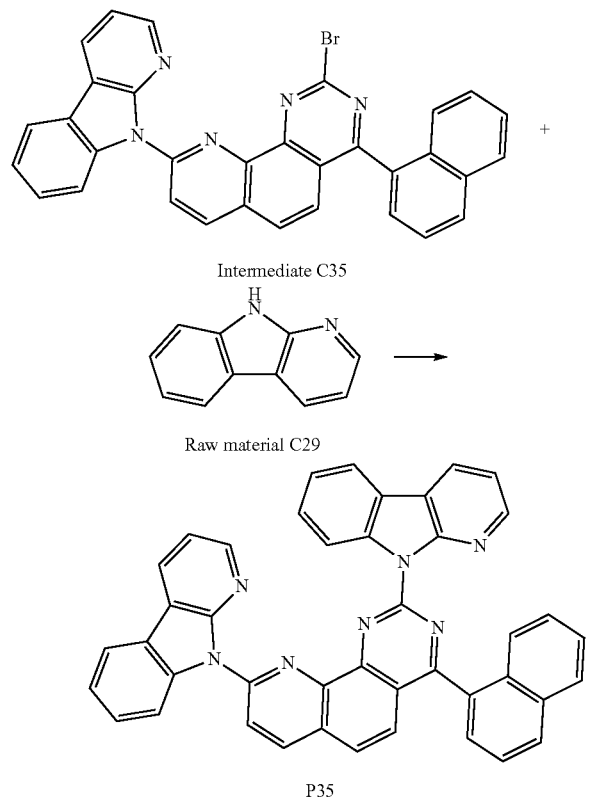

(4) 0.06 mol of Intermediate C35 obtained above was added into the reaction flask, 0.06 mol of Raw material C29 (CAS No.: 244-76-8), 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P35 was obtained; the crude Compound P35 was passed through a silica gel column through ethyl acetate and petroleum ether to obtain 28.79 g of pure Compound P35 with a yield of 75%. m/z=640.20[M+H]$^+$.

Synthesis Example 11, Synthesis of Compound P36

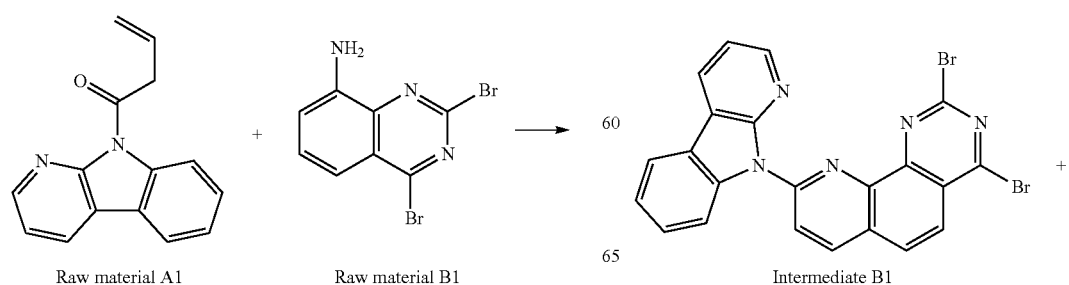

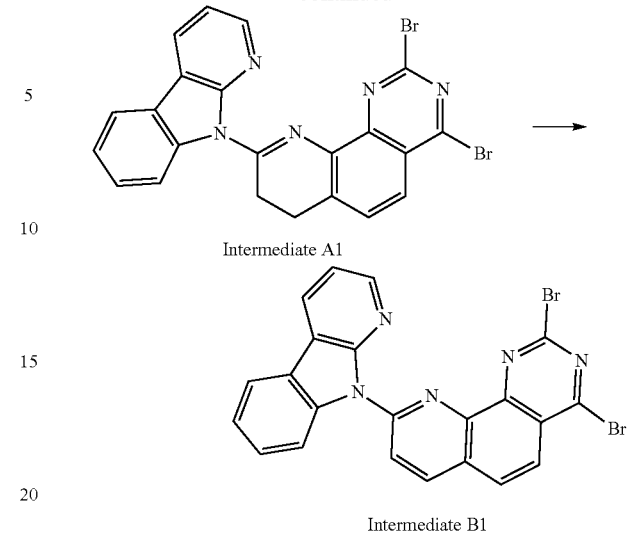

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

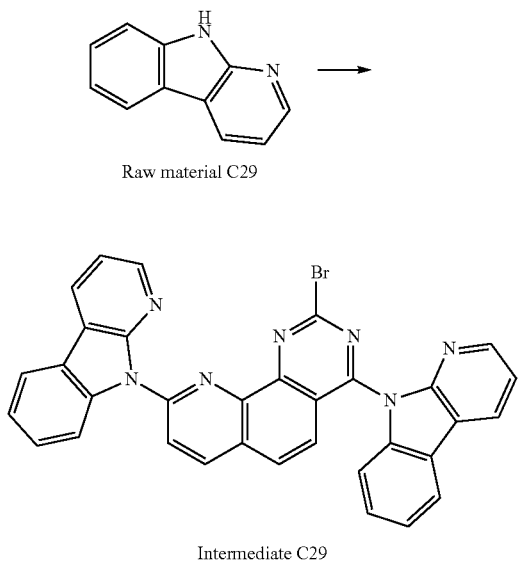

Raw material C29

Intermediate C29

(3) 0.08 mol of Intermediate B1 obtained above was added into the reaction flask, 0.06 mol of Raw material C29, 0.008 mol of cuprous bromide, 0.0008 mol of 1,10-phenanthroline, 0.16 mol of potassium carbonate and 500 mL of dimethylbenzene were added under the protection of nitrogen, heated to 130~135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that 30.14 g of crude Intermediate C29 was obtained; the crude Compound C29 was passed through a silica gel column through ethyl acetate and petroleum ether to obtain 35.55 g of pure Intermediate C29 with a yield of 75%.

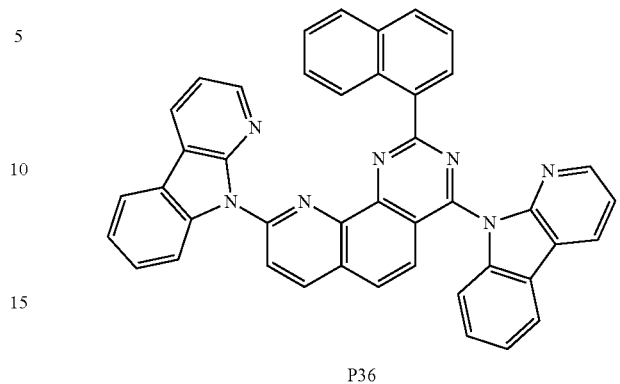

P36

(4) 0.06 mol of Intermediate C29 obtained above was added into the reaction flask, 0.06 mol of Raw material D36, 0.00006 mol of tetrakis(triphenylphosphine)palladium, 0.006 mol of tetrabutylammonium bromide, 0.12 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P36 was obtained; the crude Intermediate P36 was recrystallized with toluene to obtain 31.88 g of pure Compound P36 with a yield of 83.05%. m/z=640.22[M+H]$^+$.

Synthesis Example 12, Synthesis of Compound P43

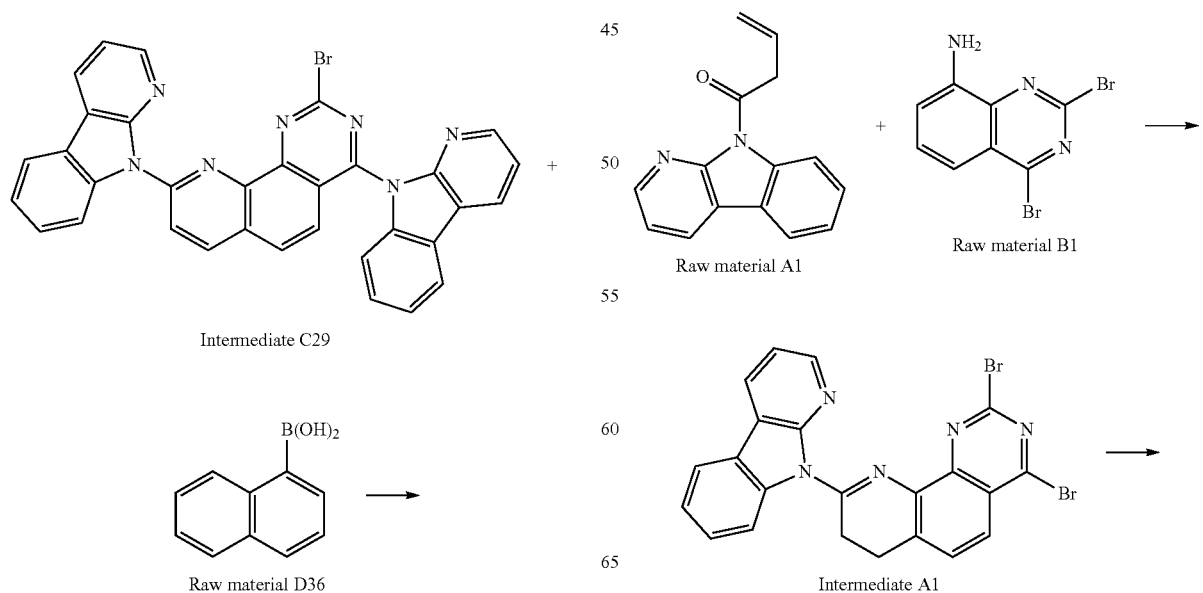

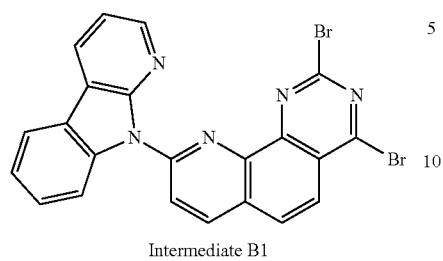

Intermediate B1

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

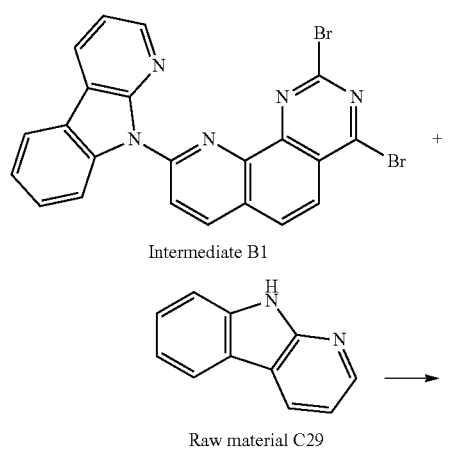

Intermediate B1

Raw material C29

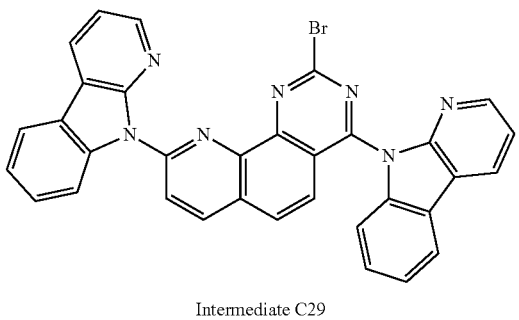

Intermediate C29

(3) 0.08 mol of Intermediate B1 obtained above was added into the reaction flask, 0.06 mol of Raw material C29, 0.008 mol of cuprous bromide, 0.0008 mol of 1,10-phenanthroline, 0.16 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Intermediate C29 was obtained; the crude Intermediate C1 was passed through a silica gel column through ethyl acetate and petroleum ether to obtain 35.55 g of pure Intermediate C29 with a yield of 75%.

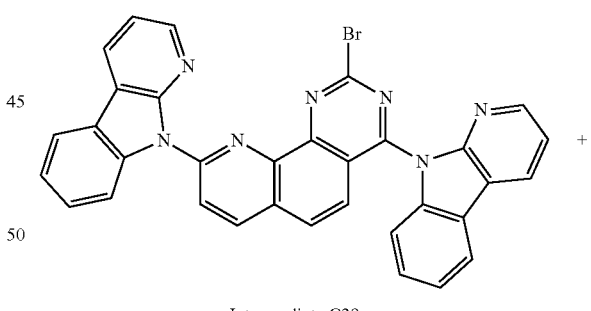

Intermediate C29

Raw material D43

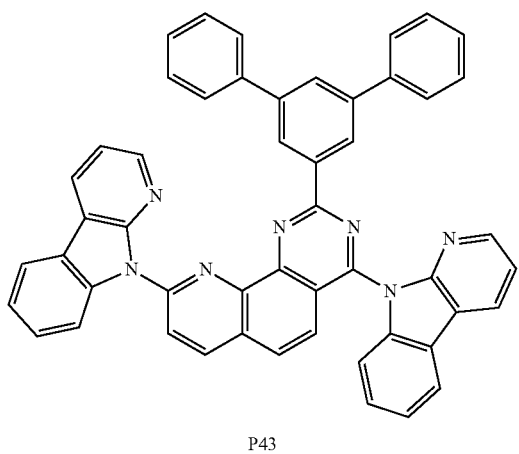

P43

(4) 0.08 mol of Intermediate C29 obtained above was added into the reaction flask, 30.08 mol of Raw material D4, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Compound P43 was obtained; the crude Intermediate P43 was recrystallized with toluene to obtain 36.52 g of pure Compound P43 with a yield of 82.05%. m/z=742.26[M+H]$^+$.

Synthesis Example 13, Synthesis of Compound P49

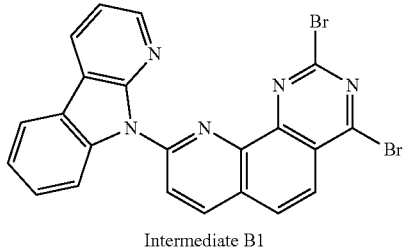

Intermediate B1

(1) 0.15 mol of Raw material Al, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate Al with a yield of 95% was obtained.

(2) 47.99 g of Intermediate Al obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

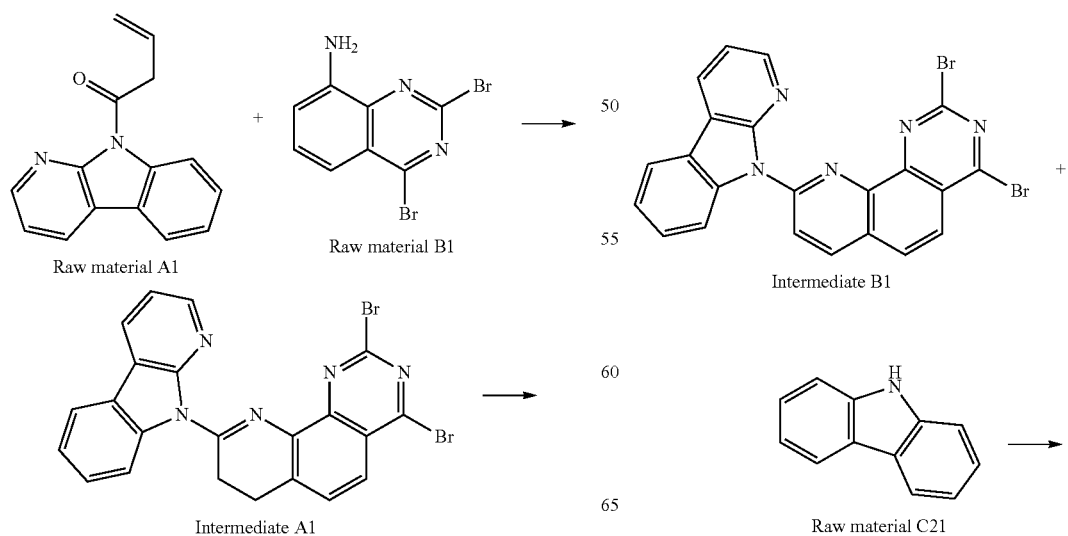

-continued

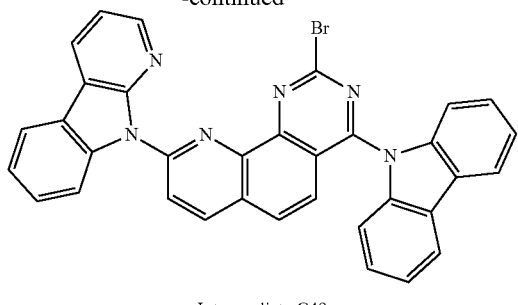

Intermediate C49

(3) 0.08 mol of Intermediate B1 obtained above was added into the reaction flask, 0.08 mol of Raw material C21 (CAS No.: 86-74-8), 0.008 mol of cuprous bromide, 0.0008 mol of 1,10-phenanthroline, 0.16 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Intermediate C49 was obtained; the crude Intermediate C49 was passed through a silica gel column through ethyl acetate and petroleum ether to obtain 35.49 g of pure Intermediate C49 with a yield of 75%.

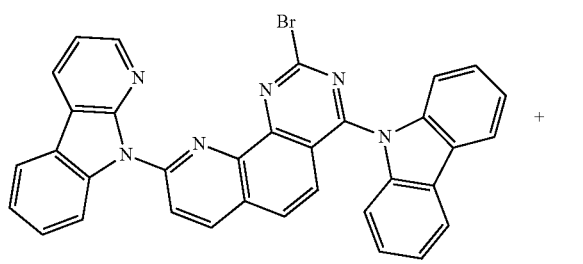

Intermediate C49

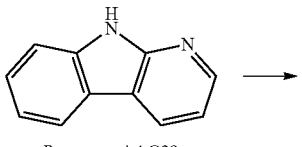

Raw material C29

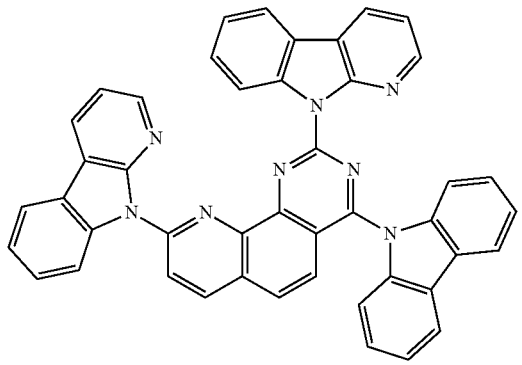

P49

(4) 0.06 mol of Intermediate C49 obtained above was added into the reaction flask, 0.06 mol of Raw material C29 (CAS No.: 244-76-8), 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P49 was obtained; the crude Compound P49 was passed through a silica gel column through ethyl acetate and petroleum ether to obtain 305.44 g of pure Compound P49 with a yield of 75%. m/z=679.20[M+H]$^+$.

Synthesis Example 14, Synthesis of Compound P55

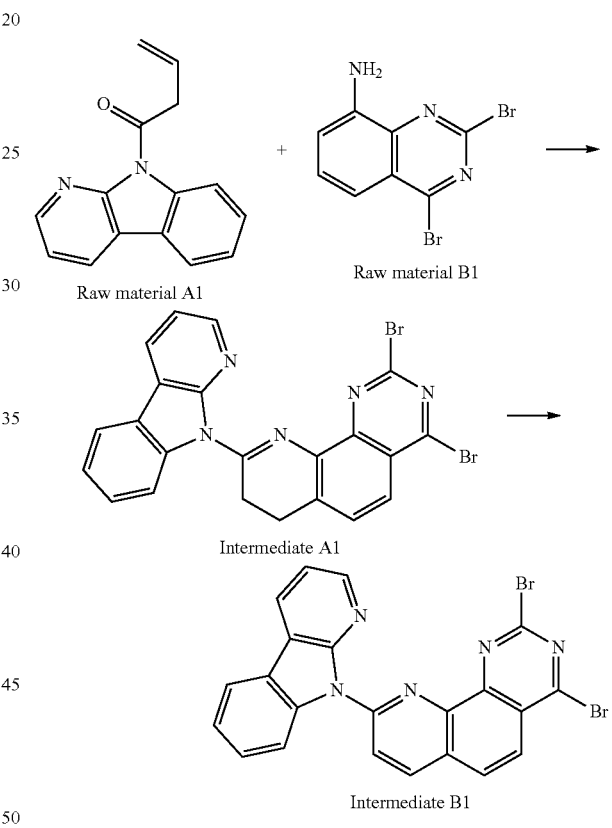

(1) 0.15 mol of Raw material A1, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A1 with a yield of 95% was obtained.

(2) 47.99 g of Intermediate A1 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B1 with a yield of 84.21%.

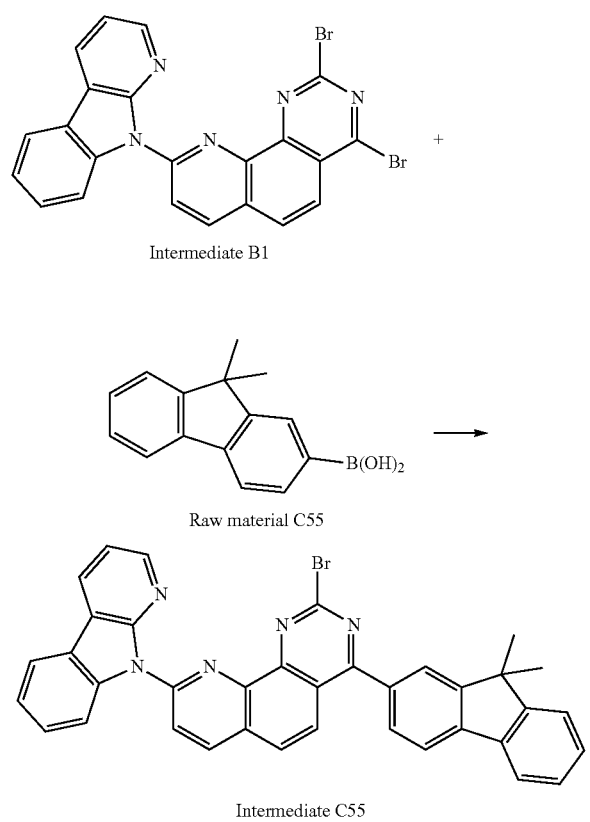

(3) 0.08 mol of Intermediate B1 obtained above was added into the reaction flask, 0.08 mol of Raw material C55, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C55 was obtained; the crude Intermediate C55 was recrystallized with toluene to obtain 37.11 g of pure Intermediate C55 with a yield of 75%.

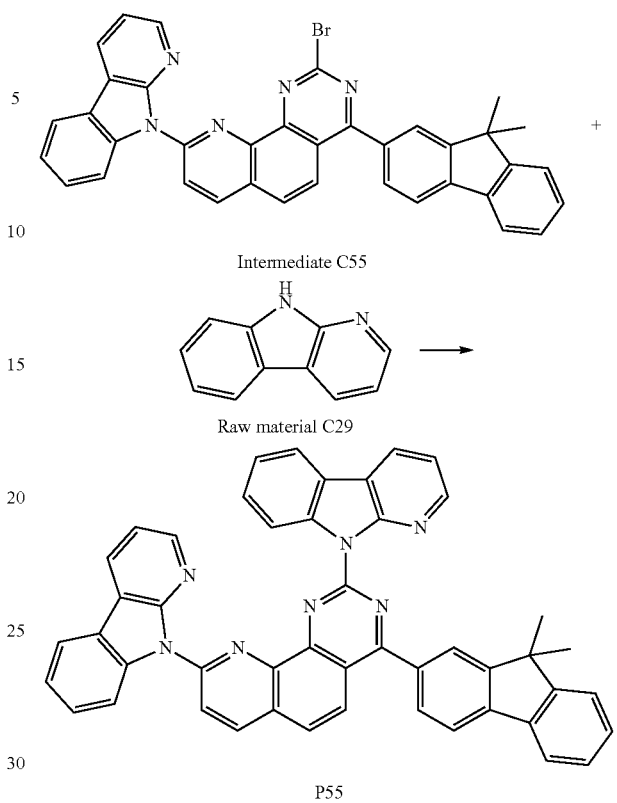

(4) 0.06 mol of Intermediate C55 obtained above was added into the reaction flask, 0.06 mol of Raw material C29 (CAS No.: 244-76-8), 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P55 was obtained; the crude Compound P55 was passed through a silica gel column through ethyl acetate and petroleum ether to obtain 305.44 g of pure Compound P55 with a yield of 75%. m/z=706.26[M+H]$^+$.

Synthesis Example 15, Synthesis of Compound P57

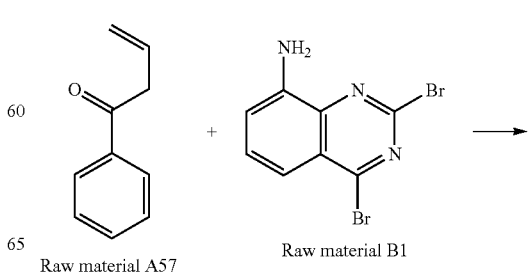

-continued

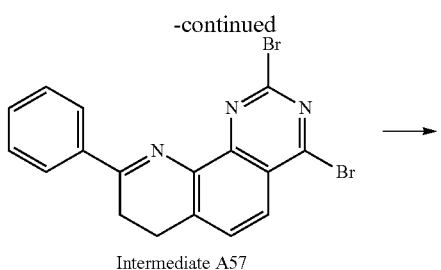

Intermediate A57

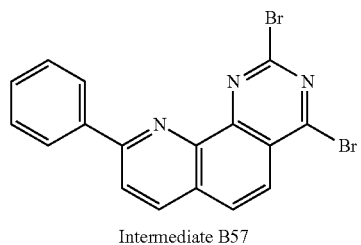

Intermediate B57

(1) 0.15 mol of Raw material A57, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 39.43 g of crude Intermediate A57 with a yield of 95% was obtained.

(2) 39.43 g of Intermediate A57 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 33.03 g of pure Intermediate B57 with a yield of 84.21%.

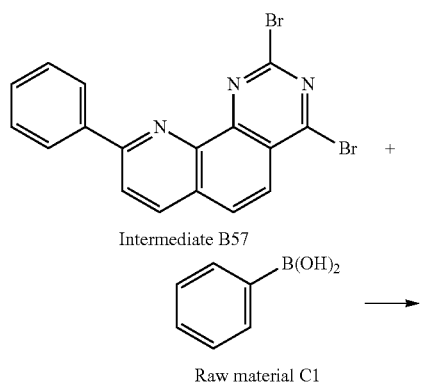

Intermediate B57

Raw material C1

-continued

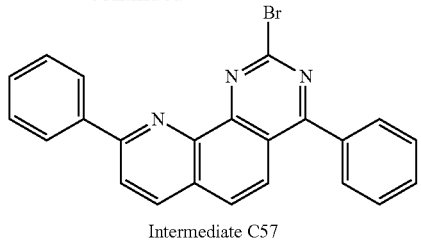

Intermediate C57

(3) 0.08 mol of Intermediate B57 obtained above was added into the reaction flask, 0.08 mol of Raw material C1, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C57 was obtained; the crude Intermediate C57 was recrystallized with toluene to obtain 24.73 g of pure Intermediate C57 with a yield of 75%.

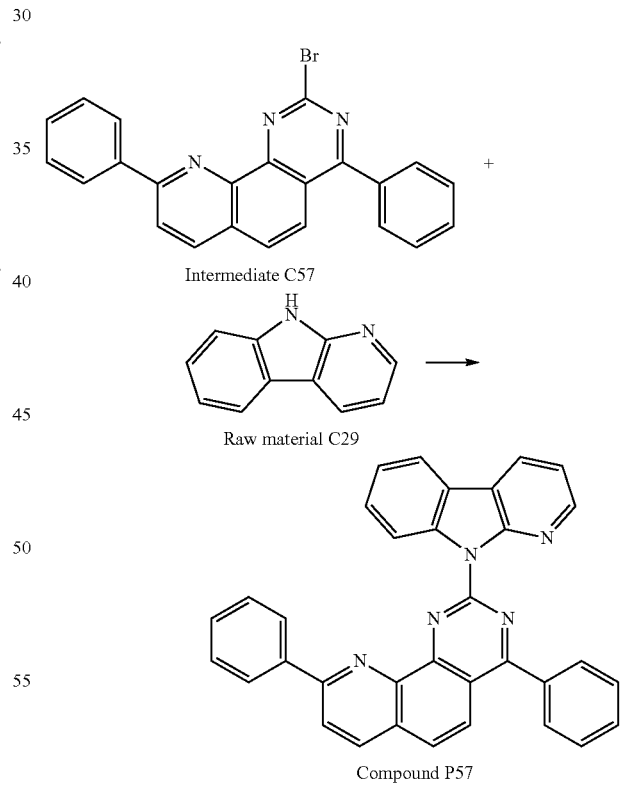

Intermediate C57

Raw material C29

Compound P57

(4) 0.06 mol of Intermediate C57 obtained above was added into the reaction flask, 0.06 mol of Raw material C29, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P57 was obtained; the crude Compound P57 was passed through a silica gel column through ethyl acetate and petroleum ether to obtain 33.97 g of pure Compound P57 with a yield of 68.01%.

m/z=500.12 [M+H]$^+$.

Synthesis Example 16, Synthesis of Compound P64

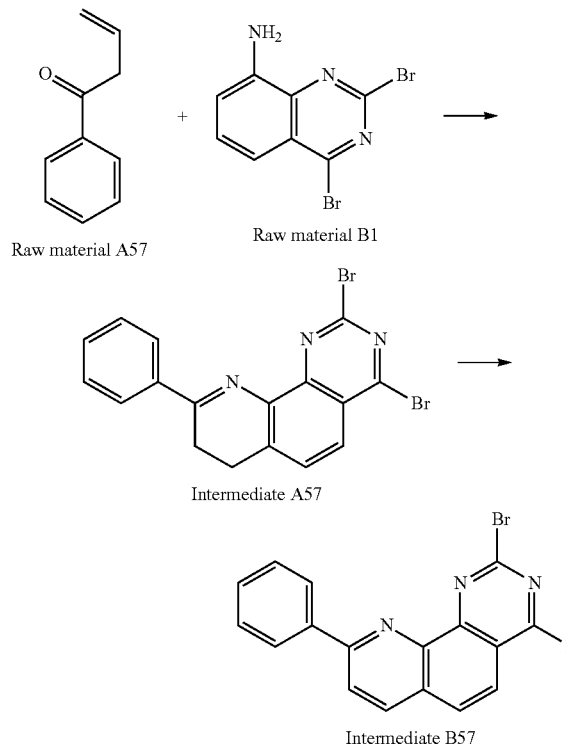

Raw material A57

Raw material B1

Intermediate A57

Intermediate B57

(1) 0.15 mol of Raw material A57, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 39.43 g of crude Intermediate A57 with a yield of 95% was obtained.

(2) 39.43 g of Intermediate A57 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 33.03 g of pure Intermediate B57 with a yield of 84.21%.

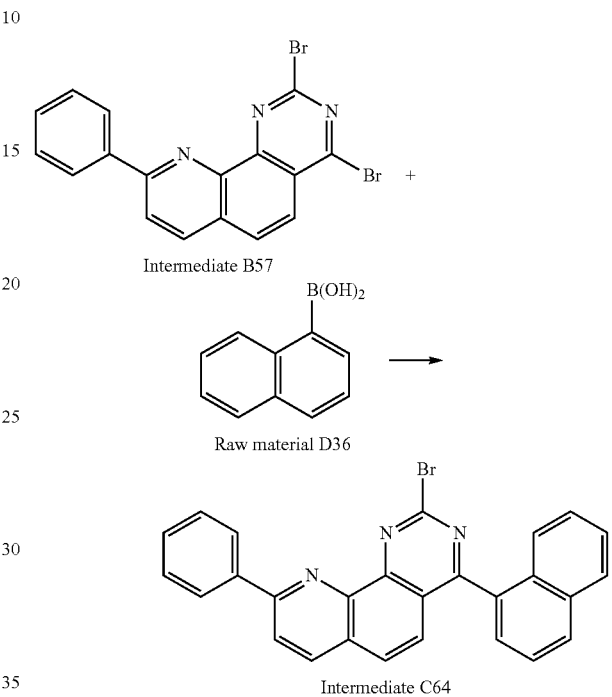

Intermediate B57

Raw material D36

Intermediate C64

(3) 0.08 mol of Intermediate B57 obtained above was added into the reaction flask, 0.08 mol of Raw material D36, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C64 was obtained; the crude Intermediate C64 was recrystallized with toluene to obtain 27.74 g of pure Intermediate C64 with a yield of 75%.

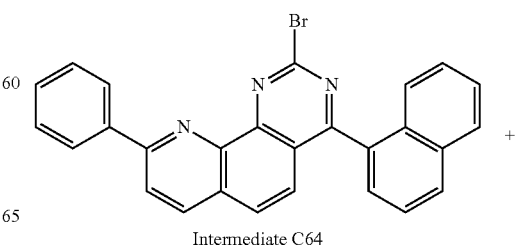

Intermediate C64

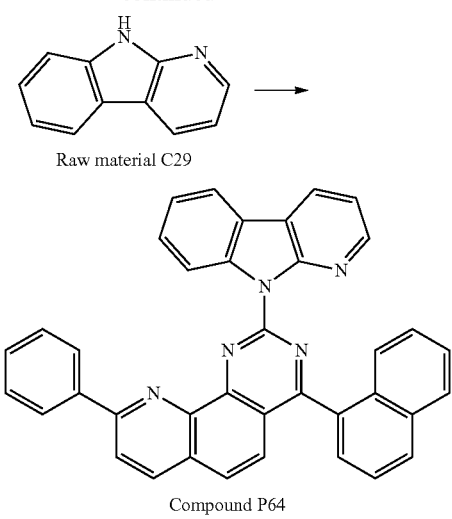

Raw material C29

Compound P64

(4) 0.06 mol of Intermediate C64 obtained above was added into the reaction flask, 0.06 mol of Raw material C29, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P64 was obtained;

the crude Compound P64 was passed through a silica gel column through ethyl acetate and petroleum ether to obtain 23.48 g of pure Compound P64 with a yield of 71.21%. m/z=550.18[M+H]$^+$.

Synthesis Example 17, Synthesis of Compound P82

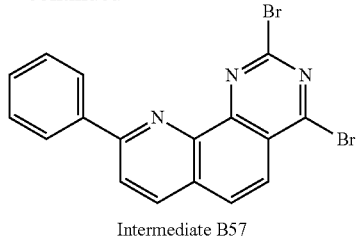

Intermediate B57

(1) 0.15 mol of Raw material A57, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 39.43 g of crude Intermediate A57 with a yield of 95% was obtained.

(2) 39.43 g of Intermediate A57 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether, to obtain 33.03 g of pure Intermediate B57 with a yield of 84.21%.

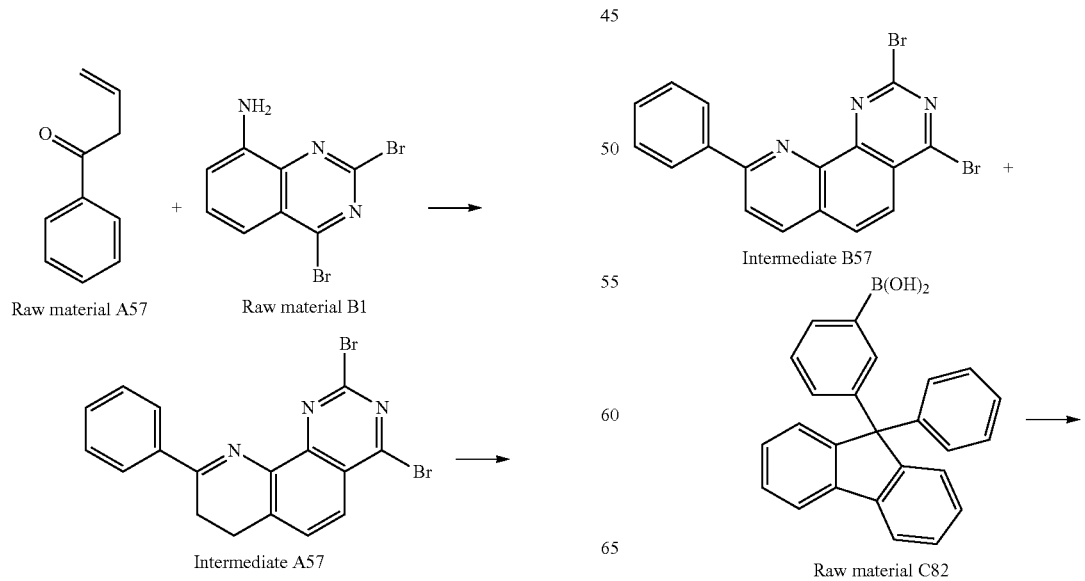

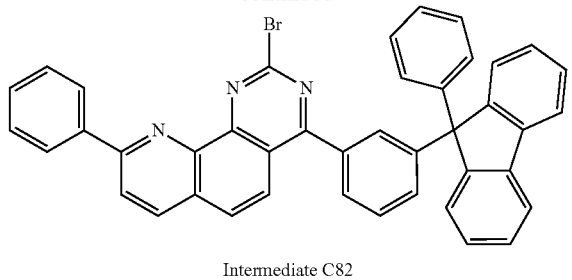

Intermediate C82

(3) 0.08 mol of Intermediate B57 obtained above was added into the reaction flask, 0.08 mol of Raw material C82, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C82 was obtained; the crude Intermediate C82 was recrystallized with toluene to obtain 39.16 g of pure Intermediate C82 with a yield of 75%.

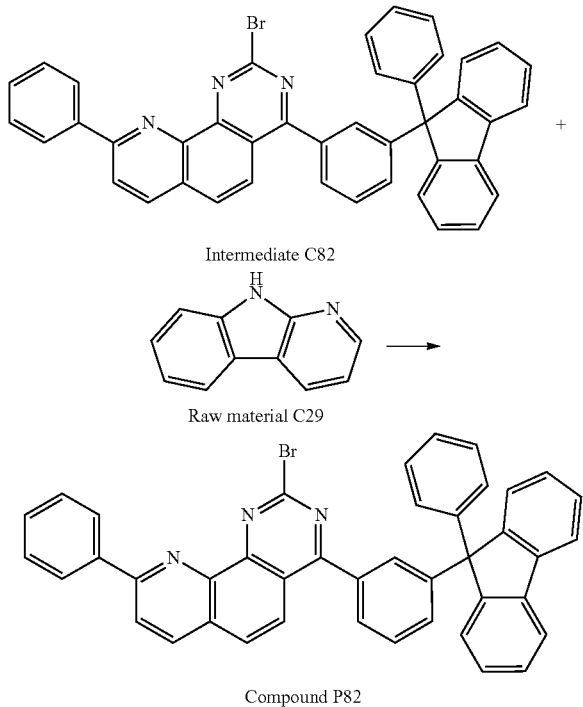

Intermediate C82

Raw material C29

Compound P82

(4) 0.06 mol of Intermediate C82 obtained above was added into the reaction flask, 0.06 mol of Raw material C29 (CAS No.: 244-76-8), 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P82 was obtained; the crude Compound P82 was passed through a silica gel column through ethyl acetate and petroleum ether to obtain 33.25 g of pure Compound P82 with a yield of 75%. m/z=739.26[M+H]$^+$.

Synthesis Example 18, Synthesis of Compound P92

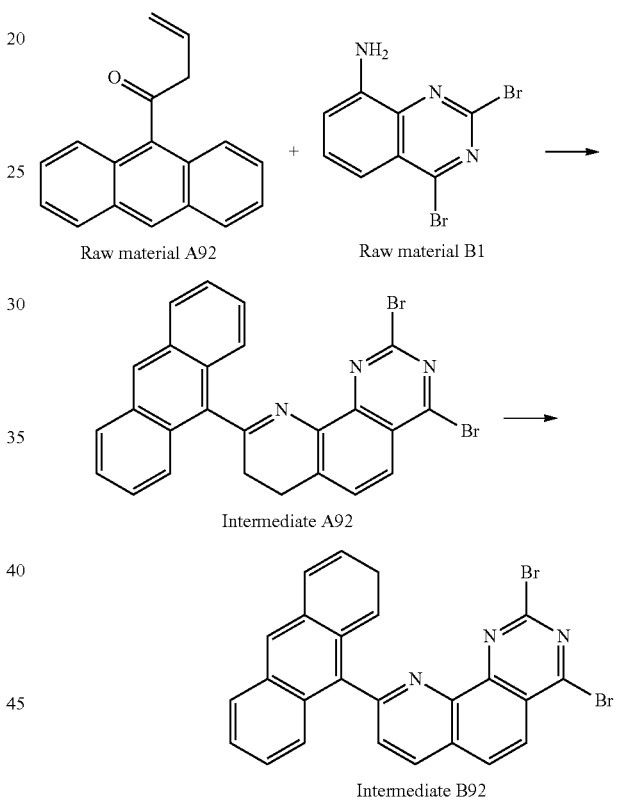

Raw material A92     Raw material B1

Intermediate A92

Intermediate B92

(1) 0.15 mol of Raw material A92, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 42.22 g of crude Intermediate A92 with a yield of 95% was obtained.

(2) 42.22 g of Intermediate A92 obtained above was added to a reaction flask, then 400 mL of toluene and 0.2 mol of arsenic pentoxide were added, and heated to 50~60° C. for a reaction for 5 h; when the reactiater stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 41.22 g of pure Intermediate B92 with a yield of 84.21%.

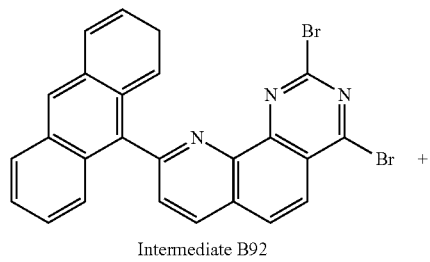

Intermediate B92

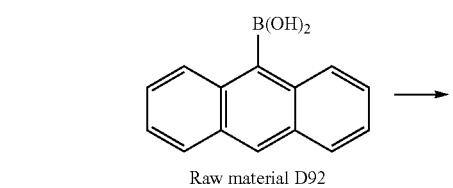

Raw material D92

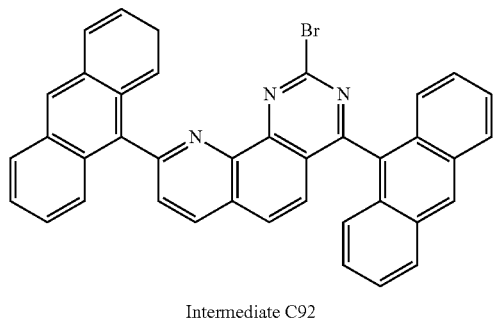

Intermediate C92

(3) 0.08 mol of Intermediate B92 obtained above was added into the reaction flask, 0.08 mol of Raw material D92, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C92 was obtained; the crude Intermediate C92 was recrystallized with toluene to obtain 36.75 g of pure Intermediate C92 with a yield of 75%.

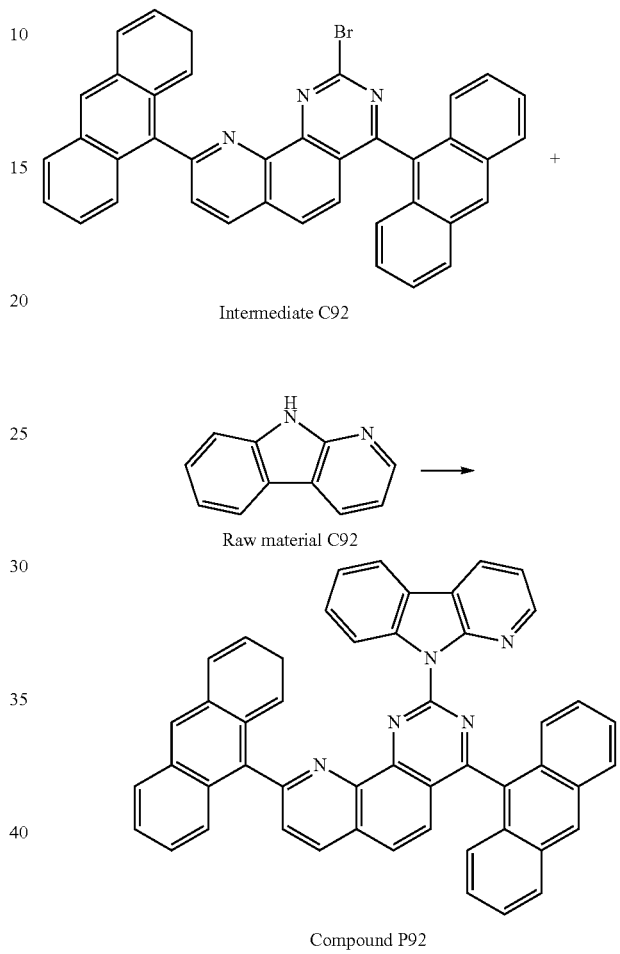

(4) 0.06 mol of Intermediate C92 obtained above was added into the reaction flask, 0.06 mol of Raw material C29, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P92 was obtained; the crude Compound P92 was passed through a silica gel column through ethyl acetate and petroleum ether to obtain 27.62 g of pure Compound P92 with a yield of 65.78%. m/z=700.18[M+H]$^+$.

$^1$H-NMR (CDCl$_3$, 300 MHz): δ(ppm)=9.01-8.98 (d, 1H), 8.76-8.73 (s, 1H), 8.70-8.68 (s, 1H), 8.61-8.57 (m, 2H), 8.50-8.47 (d, 1H), 8.32-8.26 (m, 4H), 8.22-8.15 (m, 4H), 8.11-8.08 (d, 1H), 8.01-7.99 (d, 1H), 7.63-7.52 (m, 9H), 7.44-7.39 (m, 2H), 7.26-7.22 (m, 2H).

Synthesis Example 19, Synthesis of Compound P102

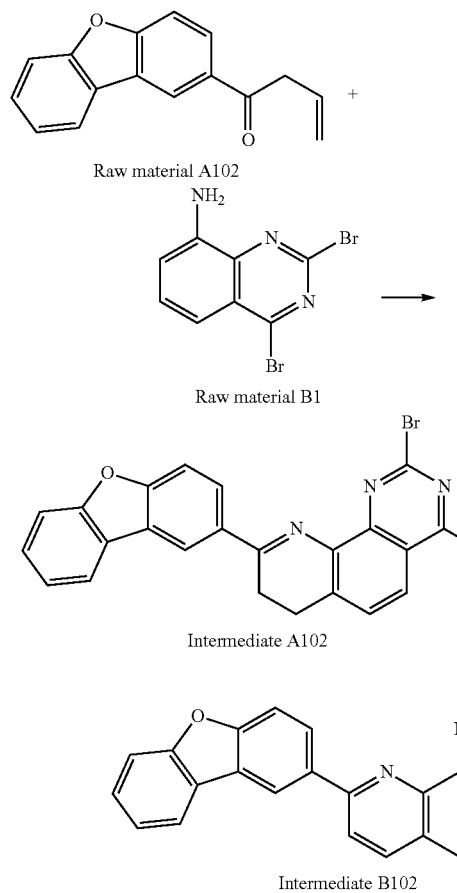

Raw material A102

Raw material B1

Intermediate A102

Intermediate B102

(1) 0.15 mol of Raw material A102, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 47.99 g of crude Intermediate A102 with a yield of 95% was obtained.

(2) 47.99 g of Intermediate A102 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 40.41 g of pure Intermediate B102 with a yield of 84.21%.

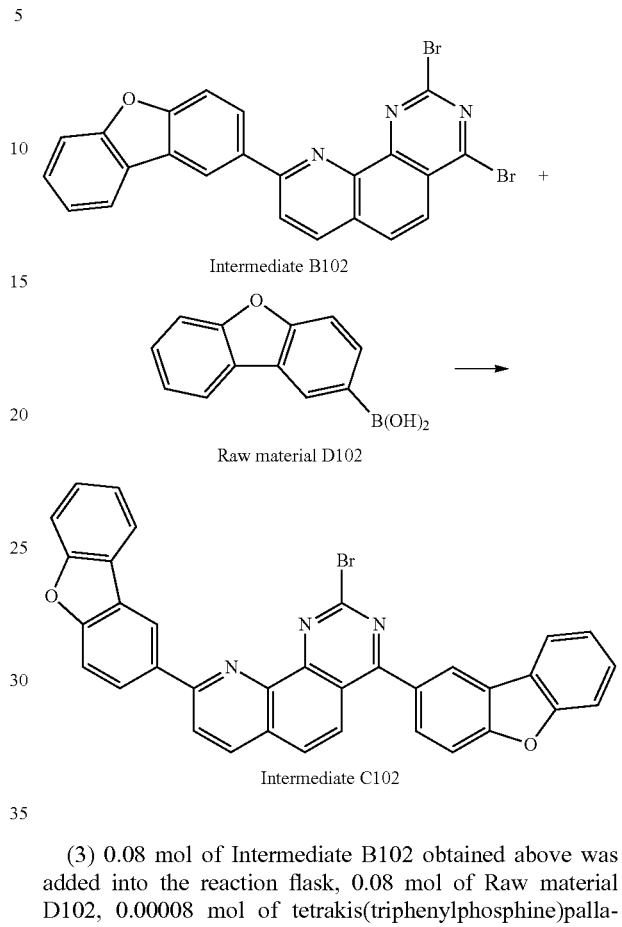

Intermediate B102

Raw material D102

Intermediate C102

(3) 0.08 mol of Intermediate B102 obtained above was added into the reaction flask, 0.08 mol of Raw material D102, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75~80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C102 was obtained; the crude Intermediate C102 was recrystallized with toluene to obtain 35.55 g of pure Intermediate C102 with a yield of 75%.

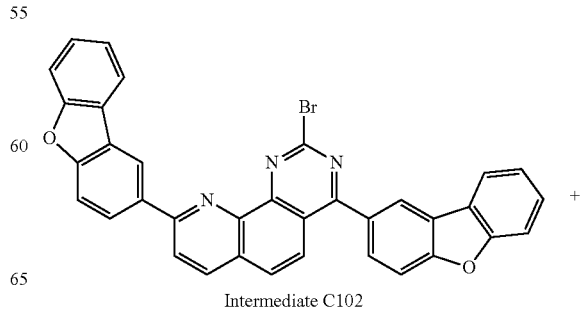

Intermediate C102

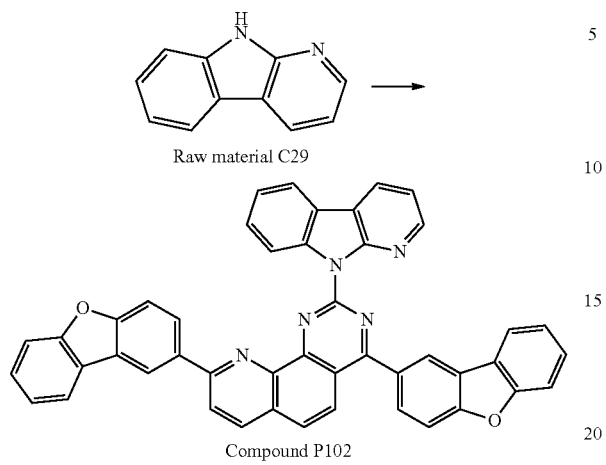

Raw material C29

Compound P102

(4) 0.06 mol of Intermediate C102 obtained above was added into the reaction flask, 0.06 mol of Raw material C29, 0.006 mol of cuprous bromide, 0.0006 mol of 1,10-phenanthroline, 0.12 mol of potassium carbonate and 500 mL of dimethylbenzene were added under the protection of nitrogen, heated to 130-135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P102 was obtained; the crude Compound P102 was passed through a silica gel column through ethyl acetate and petroleum ether to obtain 45.69 g of pure Compound P102 with a yield of 67.22%. m/z=680.17[M+H]$^+$.

$^1$H NMR (CDCl$_3$, 300 MHz): δ(ppm)=8.93-8.90 (d, 1H), 8.78-8.74 (d, 2H), 8.68-8.65 (d, 1H), 8.47-8.44 (d, 1H), 8.39-8.37 (s, 1H), 8.21-8.17 (m, 3H), 8.13-8.06 (m, 5H), 7.83-7.78 (m, 3H), 7.69-7.63 (m, 6H), 7.31-7.28 (m, 2H).

Synthesis Example 20, Synthesis of Compound P105

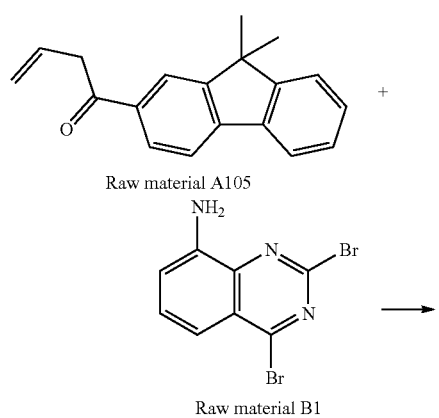

Raw material A105

Raw material B1

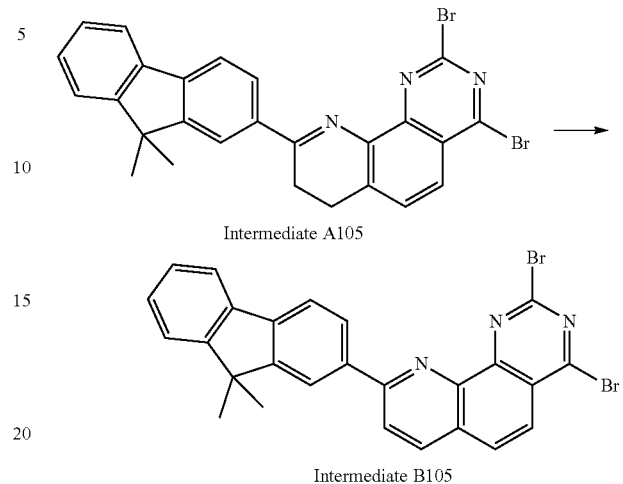

Intermediate A105

Intermediate B105

(1) 0.15 mol of Raw material A105, 0.1 mol of Raw material B1, 300 mL of toluene and 1 mol of concentrated sulfuric acid were added to a reaction flask, and stirred for a reaction at 25~30° C. for 48 h; when the reaction was completed, the reactant was slowly poured into ice water which was continuously stirred in this process, after the reactant was poured into the ice water, it was continuously stirred for about 2 min, then stirring was stopped, dispensing was started after the reactant was kept still for 5 min, an organic phase in the upper layer was temporarily placed, after an aqueous phase was extracted with 200 mL/time of toluene for 3 times, all organic phases were combined, washed to neutral with 300 mL/time of water, dried with anhydrous magnesium sulfate and concentrated under reduced pressure, so that 75.99 g of crude Intermediate A105 with a yield of 95% was obtained.

(2) 47.99 g of Intermediate A102 obtained above was added to a reaction flask, then 400 mL of toluene and 0.2 mol of arsenic pentoxide were added, and heated to 50~60° C. for a reaction for 5 h; when the reaction stopped, 400 mL of water was added to the reaction solution, stirred for 10 min, kept still for 5 min and dispensed, the aqueous phase was extracted with 200 mL/time of toluene for 3 times, all organic phases were combined and washed to neutral with 300 mL/time water, the obtained organic phase was dried with anhydrous magnesium sulfate and concentrated under reduced pressure, the obtained yellow solid was passed through a silica gel column with a mixed solvent of dichloromethane and petroleum ether to obtain 63.59 g of pure Intermediate B105 with a yield of 84.00%.

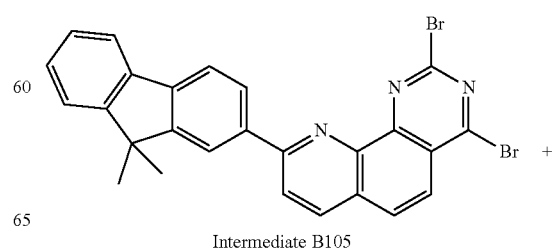

Intermediate B105

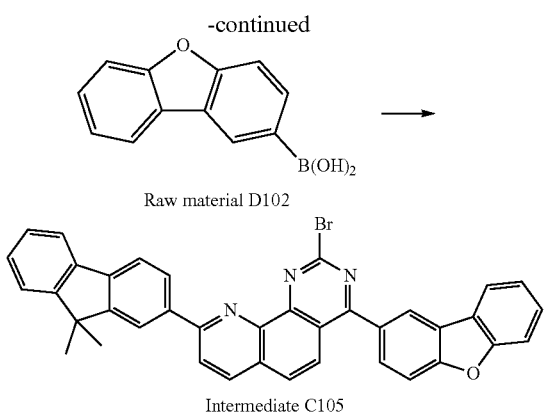

Raw material D102

Intermediate C105

(3) 0.08 mol of Intermediate B102 obtained above was added into the reaction flask, 0.08 mol of Raw material D102, 0.00008 mol of tetrakis(triphenylphosphine)palladium, 0.008 mol of tetrabutylammonium bromide, 0.16 mol of potassium carbonate, 300 mL of toluene, 100 mL of ethanol and 100 mL of water were continuously added under the protection of nitrogen, heated to 75-80° C. while stirring, the reaction stopped after 24 h, the reaction solution was dispensed after being kept still, the aqueous phase was extracted with 200 mL/time of toluene for 3 times, then all organic phases were combined, washed to neutral with 400 mL/time of water, the organic phase was dried with anhydrous magnesium sulfate and concentrated to dry under reduced pressure, so that a solid crude Intermediate C105 was obtained; the crude Intermediate C105 was recrystallized with toluene to obtain 37.11 g of pure Intermediate C105 with a yield of 75%.

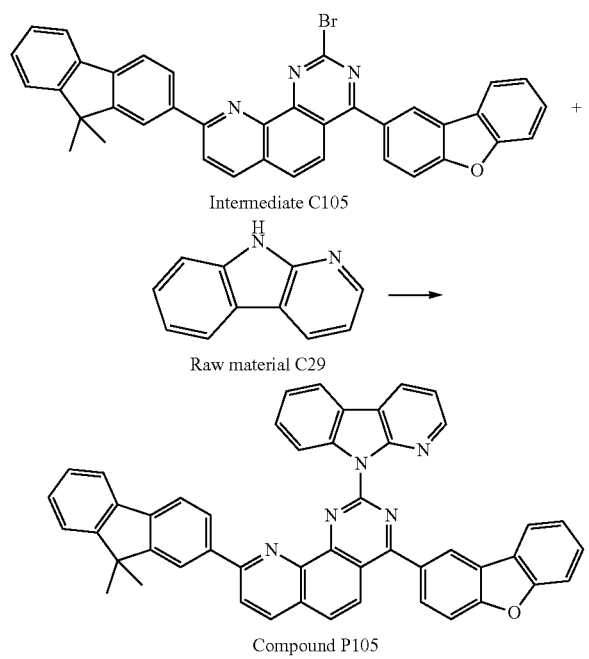

Intermediate C105

Raw material C29

Compound P105

(4) 0.06 mol of Intermediate C105 obtained above was added into the reaction flask, 0.06 mol of Raw material C29, 0.006 mol of cuprous bromide, 0.0006 mol of 1,10-phenanthroline, 0.12 mol of potassium carbonate and 500 mL of dimethylbenzene were added under the protection of nitrogen, heated to 130~135° C. while stirring, the reaction stopped after 72 h, 500 mL of water was added, the solution was dispensed after stirring for 5 min, the aqueous phase was extracted with 300 mL/time of toluene for 3 times, the combined organic phases were washed to neutral with 300 mL/time of water, dried with anhydrous magnesium sulfate and concentrated under reduced pressure, so that a crude Compound P105 was obtained; the crude Compound P105 was passed through a silica gel column through ethyl acetate and petroleum ether to obtain 29.64 g of pure Compound P105 with a yield of 70.00%. m/z=706.24 [M+H]$^+$.

$^1$H-NMR (CDCl$_3$, 300 MHz): δ(ppm)=8.91-8.89 (d, 1H), 8.76-8.73 (d, 2H), 8.63-8.60 (d, 1H), 8.36-8.34 (s, 1H), 8.25-8.22 (d, 1H), 8.16-8.13 (d, 1H), 8.04-7.98 (m, 3H), 7.96-7.91 (m, 4H), 7.79-7.75 (m, 3H), 7.63-7.56 (m, 6H), 7.28-7.25 (m, 2H), 2.06-2.03 (s, 6H).

Examples 1 to 20 are used to illustrate the use of the organic compound of the present disclosure in an electron transport layer of an organic electroluminescent device.

Example 1

The preparation steps of an organic electroluminescent device are as follows:

The anode 10 was prepared through the following process: an ITO substrate with a thickness of 1500 Å was cut into the dimension of 40 mm (length)×40 mm (width)×0.7 mm (height), the ITO substrate was prepared into a top-emitting experimental substrate having a cathode overlapping zone, a positive plate and insulation layer patterns by a photoetching procedure, and surface treatment was performed by ultraviolet ozone and O$_2$:N$_2$ plasma to increase the work function of the anode (experimental substrate) and clean the experimental substrate.

HAT-CN was vacuum deposited on the experimental substrate (anode 100) to form a hole injection layer (HIL) 310 with a thickness of 100 Å.

NPB was vacuum deposited on the hole injection layer 310 to form a hole transport layer (HTL) 320 with a thickness of 800 Å.

TCTA was vacuum deposited on the hole transport layer 320 to form an electron blocking layer (EBL) 370 with a thickness of 300 Å.

α,β-ADN was taken as a host, doped with BD-1 at a doping ratio of 3%, and α,β-ADN and BD-1 were vacuum deposited on the electron blocking layer (EBL) 370 to form an organic electroluminescent layer (EML) 330 with a thickness of 220 Å.

Compound P1 of the present disclosure was vacuum deposited on the organic electroluminescent layer 330 to form an electron transport layer (ETL) 350 with a thickness of 300 Å.

Yb was vacuum deposited on the electron transport layer 350 to form an electron injection layer (EIL) 360 with a thickness of 15 Å.

Magnesium (Mg) and silver (Ag) were mixed at a deposition rate of 1:9, and vacuum deposited on the electron injection layer to form a cathode 200 with a thickness of 120 Å.

In addition, CP-1 was vacuum deposited on the cathode 200 to form a capping layer (CPL) with a thickness of 650 Å, so that the manufacturing of the organic light-emitting device A1 was completed.

Wherein the structural formulas of HAT-CN, NPB, TCTA, α,β-ADN, BD-1 and CP-1 are as follows:

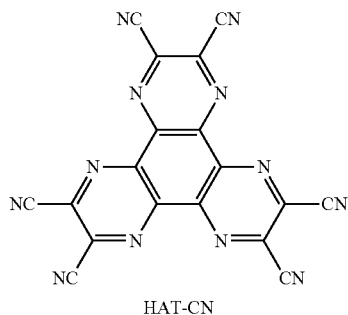

HAT-CN

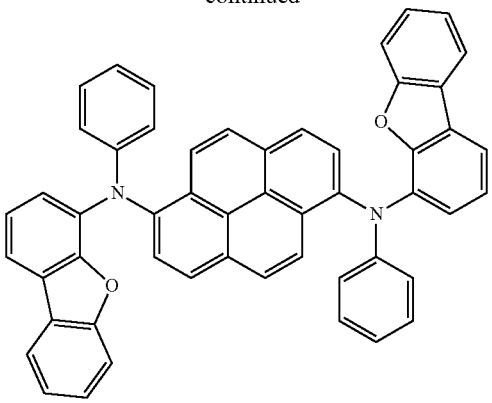

BD-1

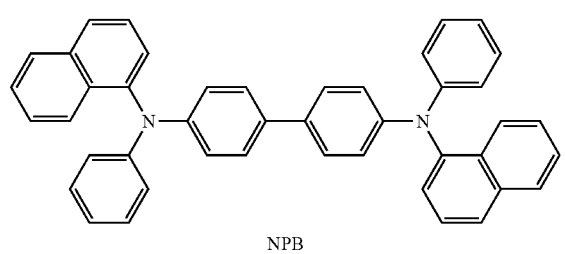

NPB

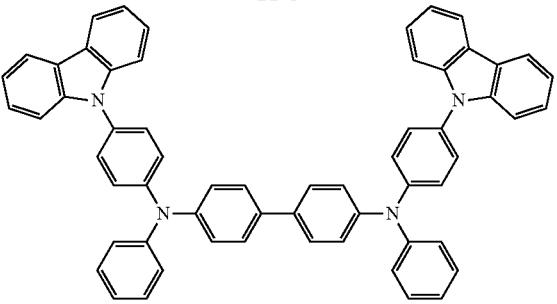

CP-1

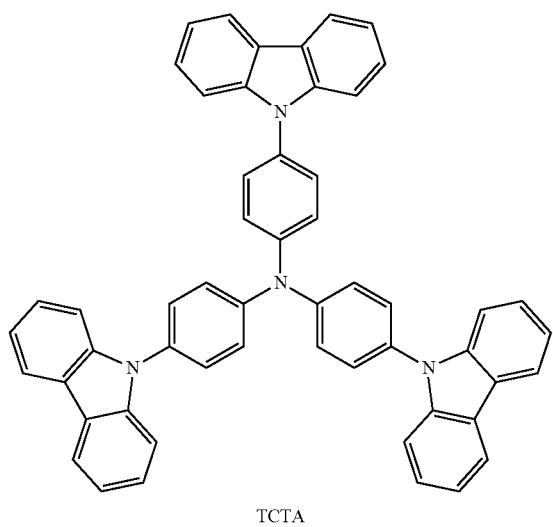

TCTA

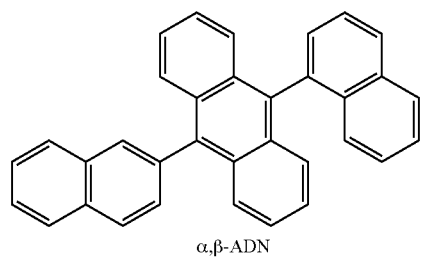

α,β-ADN

Examples 2 to 20

The organic electroluminescent devices A2 to A20 were prepared by the same method as in Example 1, and the only difference was that the organic electroluminescent devices A2 to A20 were prepared by replacing the Compound P1 with the compound prepared in synthesis examples 2 to 20 respectively.

Comparative Example 1

The organic electroluminescent device was manufactured by the same method as in Example 1, and the only difference was that: Compound P1 as the electron transport layer was replaced by Compound A, thus obtaining the organic electroluminescent device D1. The structural formula of Compound A is shown below:

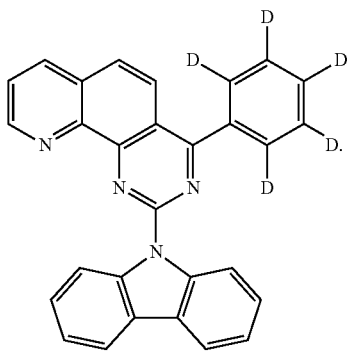

Comparative Example 2

The organic electroluminescent device was manufactured by the same method as in Example 1, and the only difference was that: Compound P1 as the electron transport layer was replaced by Compound B, thus obtaining the organic electroluminescent device D2. The structural formula of Compound B is shown below:

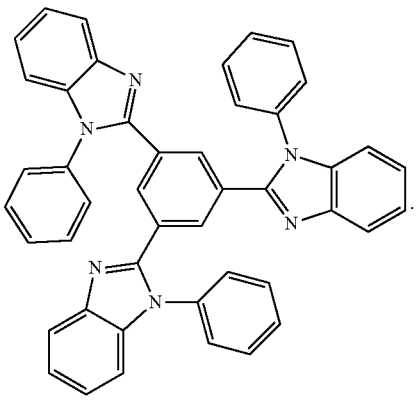 [SMILES: c1ccc(-n2c(-c3cc(-c4nc5ccccc5n4-c4ccccc4)cc(-c4nc5ccccc5n4-c4ccccc4)c3)nc3ccccc32)cc1]

Comparative Example 3

The organic electroluminescent device was manufactured by the same method as in Example 1, and the only difference was that: Compound P1 as the electron transport layer was replaced by Compound C, thus obtaining the organic electroluminescent device D3. The structural formula of Compound C is shown below:

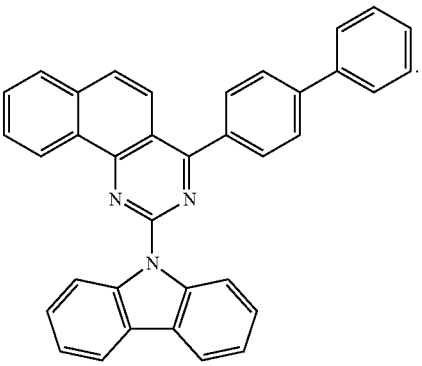 [SMILES: c1ccc(-c2ccc(-c3nc(-n4c5ccccc5c5ccccc54)nc4c3ccc3ccccc34)cc2)cc1]

Performance Test of Organic Electroluminescent Devices

The organic electroluminescent devices A1 to A20 and D1 to D3 obtained in the above examples and comparative examples were tested, the data of voltage, efficiency and chromaticity coordinates was tested at the constant current density of 10 mA/cm$^2$, the T95 device lifespan was tested at the constant current density of 15 mA/cm$^2$, and the results are shown in Table 1.

TABLE 1

| No. | Device No. | Electron transport layer material | Voltage Volt (V) | Luminous efficiency (Cd/A) | External quantum efficiency EQE (%) | T95 lifespan (h)@15 mA/cm$^2$ | Chromaticity coordinates CIEy |
|---|---|---|---|---|---|---|---|
| Example 1 | A1 | Compound P1 | 3.75 | 6.75 | 13.20 | 254 | 0.053 |
| Example 2 | A2 | Compound P2 | 3.73 | 6.70 | 13.19 | 234 | 0.052 |
| Example 3 | A3 | Compound P9 | 3.74 | 6.73 | 13.24 | 213 | 0.052 |
| Example 4 | A4 | Compound P11 | 3.79 | 6.66 | 13.21 | 209 | 0.054 |
| Example 5 | A5 | Compound P12 | 3.75 | 6.68 | 13.22 | 221 | 0.052 |
| Example 6 | A6 | Compound P21 | 3.74 | 6.75 | 13.19 | 235 | 0.051 |
| Example 7 | A7 | Compound P24 | 3.77 | 6.73 | 13.66 | 241 | 0.050 |
| Example 8 | A8 | Compound P29 | 3.76 | 6.78 | 13.18 | 245 | 0.051 |
| Example 9 | A9 | Compound P34 | 3.73 | 6.79 | 13.55 | 233 | 0.052 |
| Example 10 | A10 | Compound P35 | 3.75 | 6.68 | 13.58 | 236 | 0.051 |
| Example 11 | A11 | Compound P36 | 3.88 | 6.79 | 13.89 | 261 | 0.053 |
| Example 12 | A12 | Compound P43 | 3.79 | 6.80 | 13.88 | 265 | 0.050 |
| Example 13 | A13 | Compound P49 | 3.78 | 6.69 | 13.60 | 259 | 0.053 |
| Example 14 | A14 | Compound P55 | 3.78 | 6.72 | 23.25 | 261 | 0.053 |
| Example 15 | A15 | Compound P57 | 3.76 | 6.75 | 13.20 | 249 | 0.052 |
| Example 16 | A16 | Compound P64 | 3.79 | 6.80 | 13.81 | 183 | 0.051 |
| Example 17 | A17 | Compound P82 | 3.77 | 6.73 | 23.22 | 241 | 0.052 |
| Example 18 | A18 | Compound P92 | 3.81 | 6.80 | 13.25 | 255 | 0.052 |
| Example 19 | A19 | Compound P102 | 3.76 | 6.65 | 12.23 | 201 | 0.055 |
| Example 20 | A20 | Compound P105 | 3.75 | 6.75 | 13.52 | 235 | 0.054 |
| Comparative Example 1 | D1 | Compound A | 4.2 | 6.5 | 11.24 | 175 | 0.052 |

TABLE 1-continued

| No. | Device No. | Electron transport layer material | Voltage Volt (V) | Luminous efficiency (Cd/A) | External quantum efficiency EQE (%) | T95 lifespan (h)@15 mA/cm² | Chromaticity coordinates CIEy |
|---|---|---|---|---|---|---|---|
| Comparative Example 2 | D2 | Compound B | 4.1 | 6.0 | 10.2 | 162 | 0.052 |
| Comparative Example 3 | D3 | Compound C | 4.3 | 6.4 | 11.27 | 180 | 0.053 |

It can be seen from the above results that when the compound of the present disclosure as an electron transport layer (ETL) is compared with Comparative Example 1, Comparative Example 2 and Comparative Example 3 using Compound A, Compound B and Compound C:

the driving voltage of the organic electroluminescent devices A1 to A20 prepared in Examples 1 to 20 was 3.73-3.88V, reduced by at least 7.6% compared to the driving voltage (4.2V) of the organic electroluminescent device D1 of Comparative Example 1, reduced by at least 5.37% compared to the driving voltage (4.1V) of the organic electroluminescent device D2 of Comparative Example 2, and reduced by at least 9.8% compared to the driving voltage (4.3V) of the organic electroluminescent device D3 of Comparative Example 3. The luminous efficiency of the organic electroluminescent devices prepared in Examples 1 to 20 was 6.65-6.80 Cd/A, increased by at least 2.3% compared to the luminous efficiency (6.5 Cd/A) of the organic electroluminescent device D1 of Comparative Example 1, increased by at least 10.83% compared to the luminous efficiency (6.0 Cd/A) of the organic electroluminescent device D2 of Comparative Example 2, and increased by at least 4% compared to the luminous efficiency (6.4 Cd/A) of the organic electroluminescent device D3 of Comparative Example 3. The external quantum efficiency of the organic electroluminescent devices prepared in Examples 1 to 20 was 12.23~23.25%, increased by at least 8.8% compared to the external quantum efficiency (11.24%) of the organic electroluminescent device D1 of Comparative Example 1, increased by at least 20% compared to the external quantum efficiency (10.2%) of the organic electroluminescent device D2 of Comparative Example 2, and increased by at least 8.5% compared to the external quantum efficiency (11.27%) of the organic electroluminescent device D3 of Comparative Example 3. The T95 lifespan of the organic electroluminescent devices prepared in Examples 1 to 20 was 201-265 h, increased by at least 14.9% compared to the T95 lifespan (175 h) of the organic electroluminescent device D1 in Comparative Example 1, increased by at least 24.07% compared to the T95 lifespan (162 h) of the organic electroluminescent device D2 in Comparative Example 2, and increased by at least 11.67% compared to the T95 lifespan (180 h) of the organic electroluminescent device D3 in Comparative Example 3.

Therefore, the organic electroluminescent devices prepared in Examples 1 to 20 have lower driving voltage, higher luminous efficiency, higher external quantum efficiency and longer lifespan compared to the Comparative Examples. That is, the compound provided by the present disclosure has a better electron transport performance than that of Compound A and Compound B, and can significantly improve the performance of an organic electroluminescent device when used in an electron transport layer of the organic electroluminescent device.

The preferred examples of the present disclosure are described in detail above in combination with the figures. However, the present disclosure is not limited to the specific details in the above embodiments, various simple variants may be created for the technical solution of the present disclosure within the scope of technical conception of the present disclosure, and all these simple variants belong to the protection scope of the present disclosure.

In addition, it should be noted that the specific technical features described in the above specific embodiments can be combined in any suitable way without contradiction, and various possible combination modes will not be otherwise specified in the present disclosure in order to avoid unnecessary repetition.

Moreover, various examples of the present disclosure can also be combined arbitrarily, and should be considered as the contents disclosed by the present disclosure as long as they do not violate the idea of the present disclosure.

The invention claimed is:
1. An organic compound having a structure represented by Formula (1):

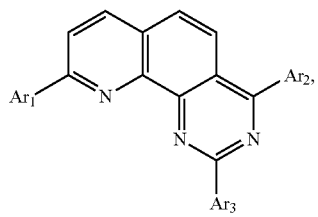

Formula (1)

wherein $Ar_1$, $Ar_2$ and $Ar_3$ are the same or different, and are each independently selected from a substituted or unsubstituted aryl having 6 to 30 carbon atoms, a substituted or unsubstituted heteroaryl having 3 to 30 carbon atoms, or a structure represented by Formula (2); wherein the aryl is phenyl, naphthyl, biphenyl, or anthracyl, and the heteroaryl is pyridyl, quinolyl, isoquinolinyl, dibenzofuranyl, or dibenzothiophenyl; and at least one of $Ar_1$, $Ar_2$ and $Ar_3$ has the structure represented by Formula (2):

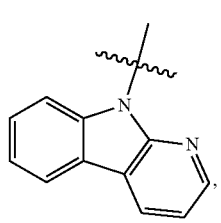

Formula (2)

⊥ represents a chemical bond;
the substituents of $Ar_1$, $Ar_2$ and $Ar_3$ are the same or different, and are each independently selected from deuterium, a fluorine, a cyano, an alkyl having 1 to 5 carbon atoms, or an unsubstituted aryl having 6 carbon atoms.

2. The organic compound according to claim 1, wherein at least two of $Ar_1$, $Ar_2$ and $Ar_3$ have the structure represented by Formula (2).

3. The organic compound according to claim 1, wherein $Ar_1$, $Ar_2$ and $Ar_3$ are selected from

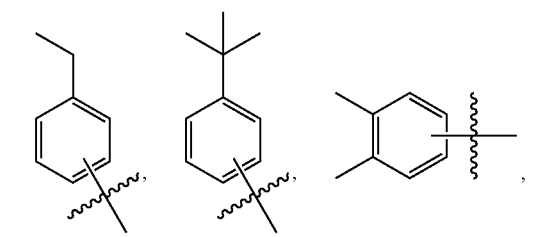

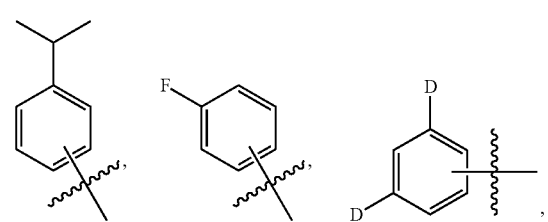

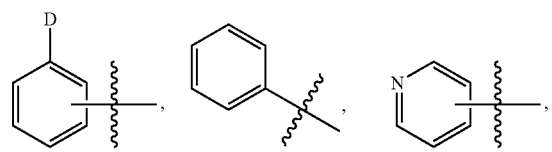

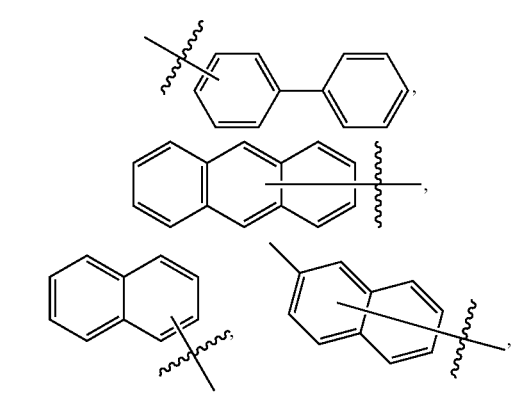

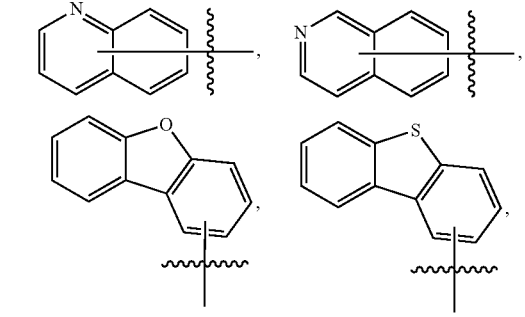

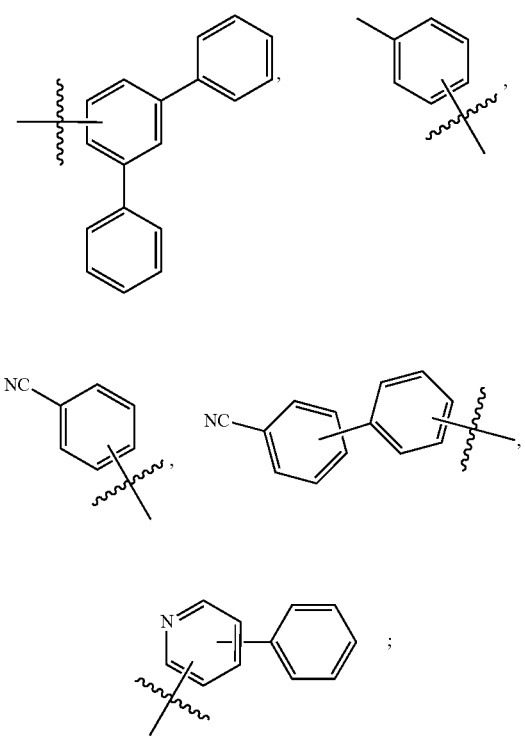

and wherein at least one of $Ar_1$, $Ar_2$ and $Ar_3$ has the structure represented by Formula (2).

4. The organic compound according to claim 1, wherein the compound is selected from one or more of the following compounds:

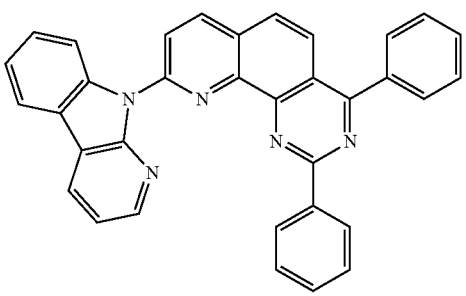
P1

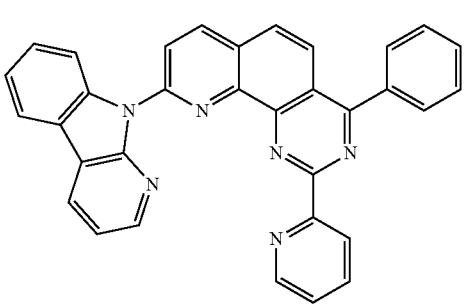
P2

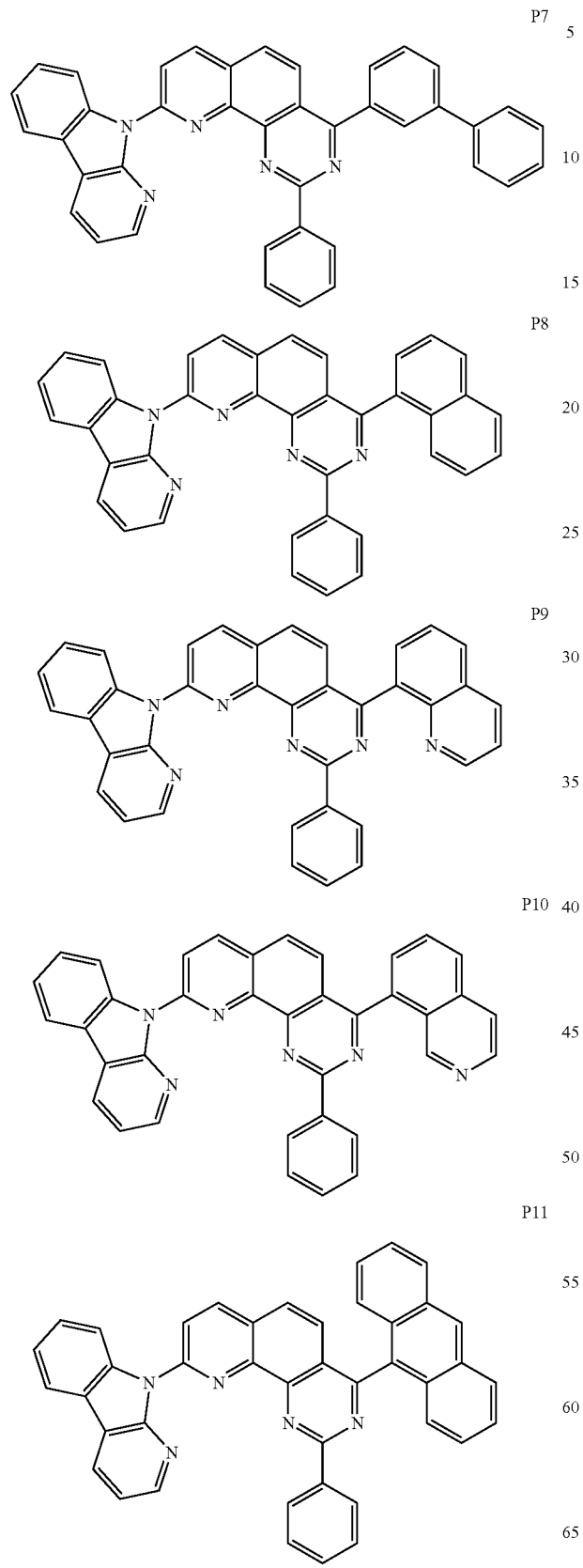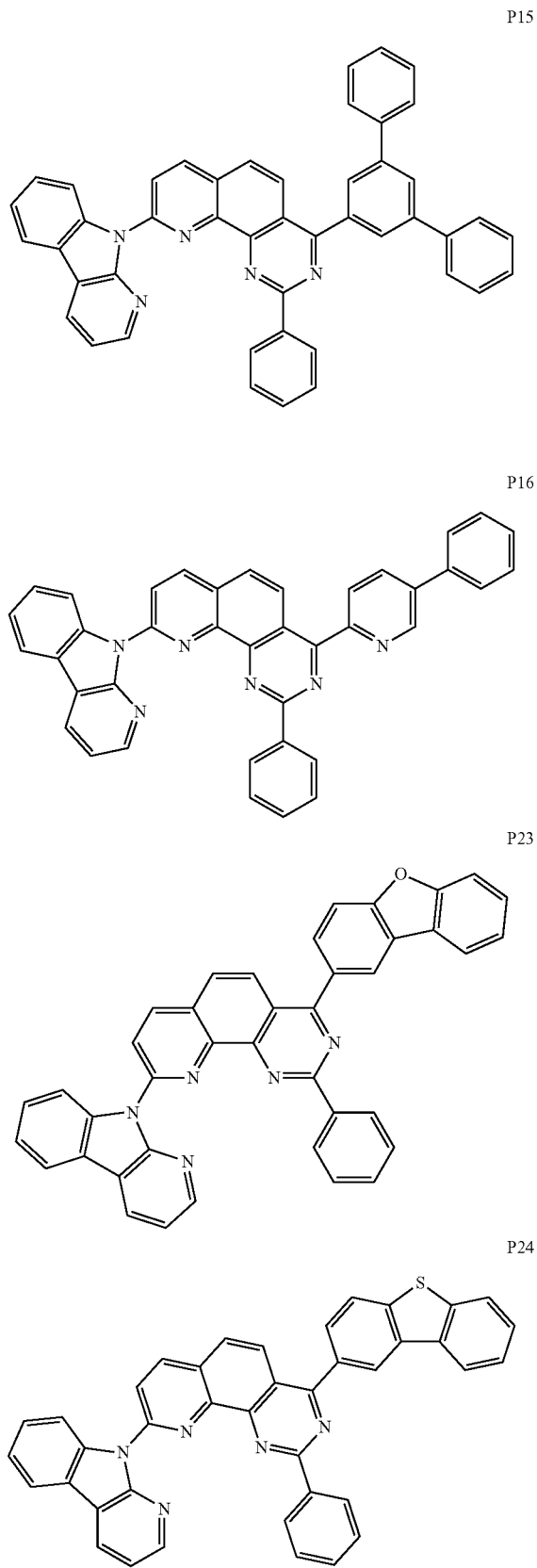

P29
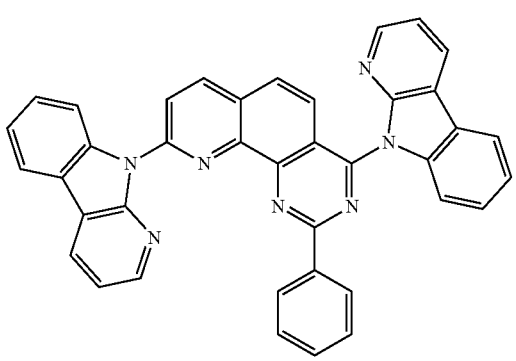
P30
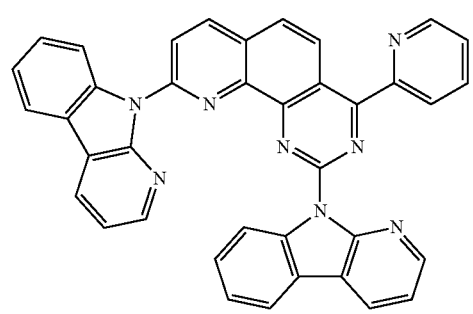
P34
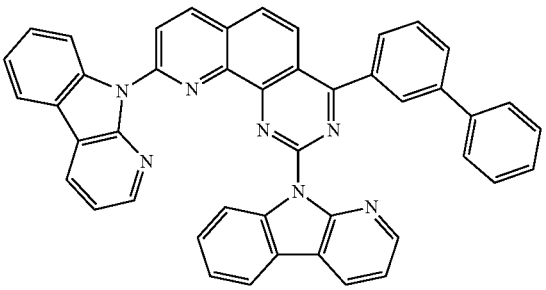
P35
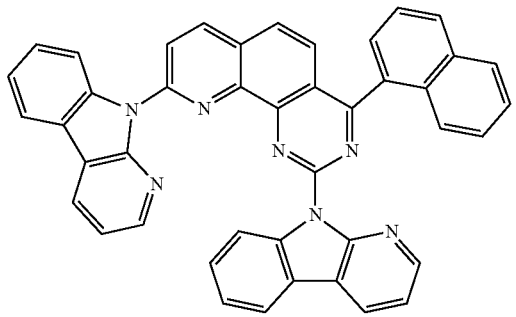
P36
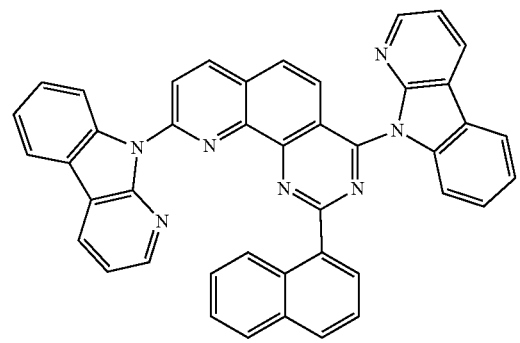
P37
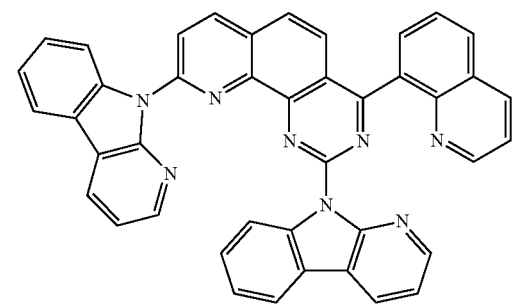
P38
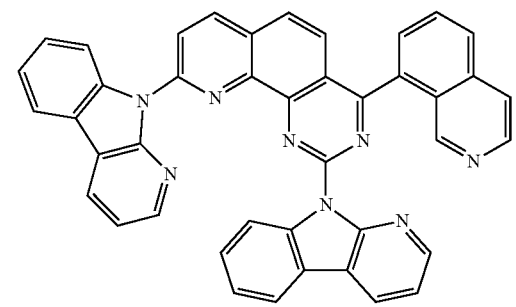
P39
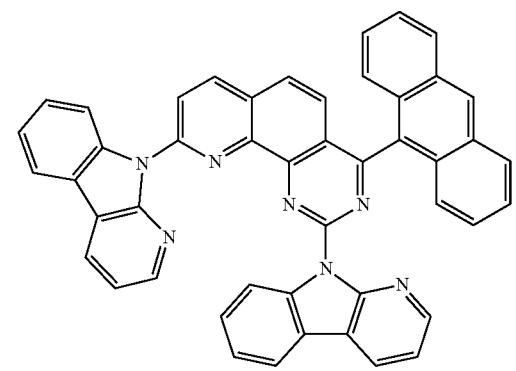

-continued
P43
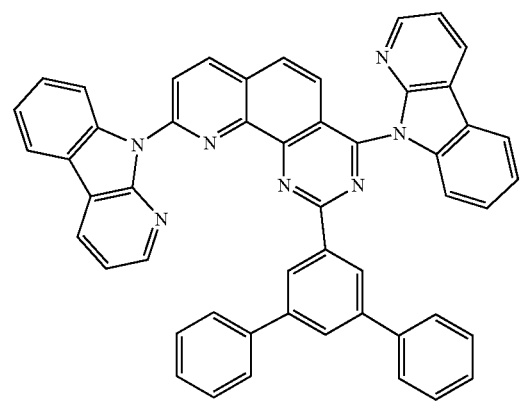
P44
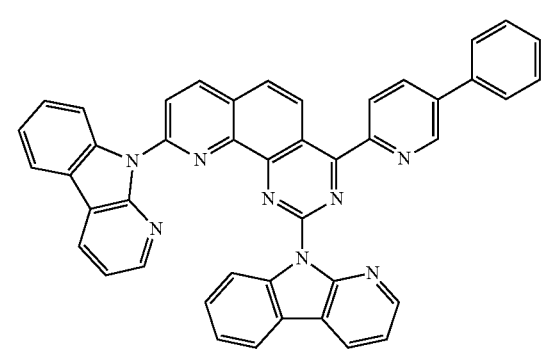
P51
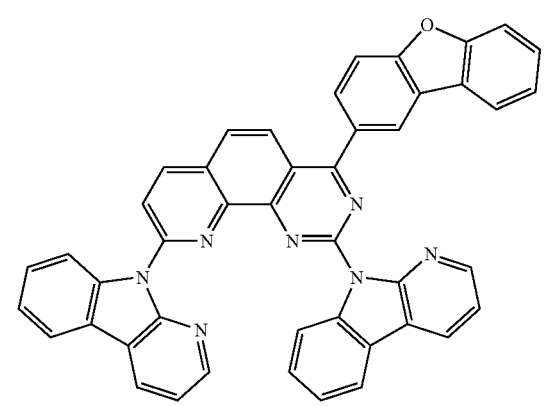
P52
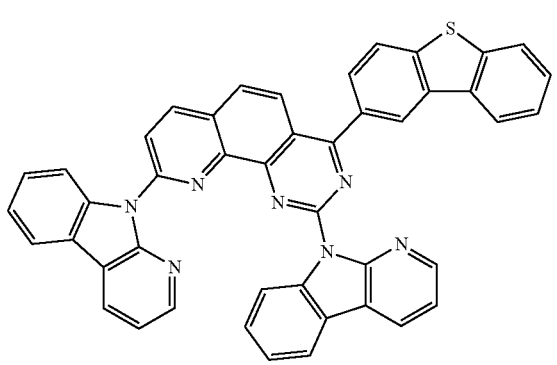
-continued
P57
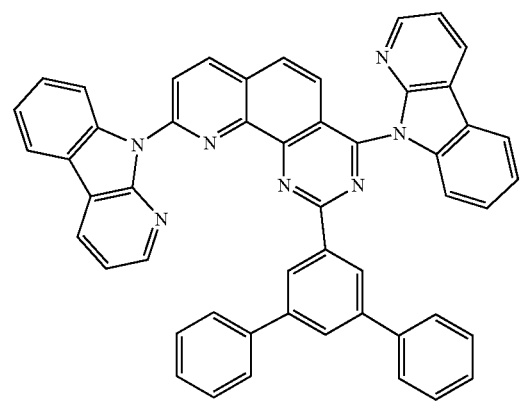
P58
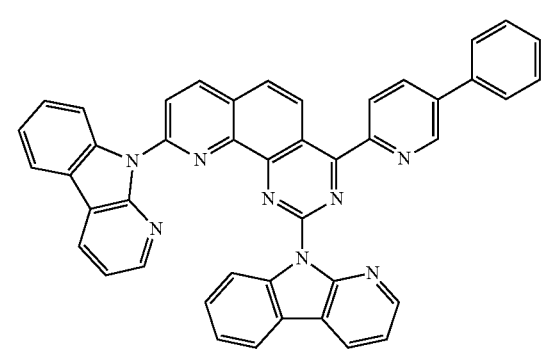
P63
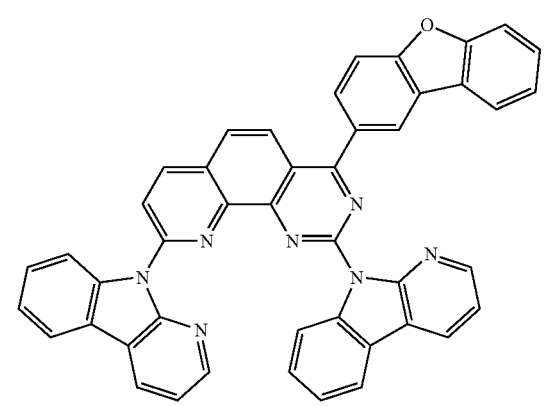
P64
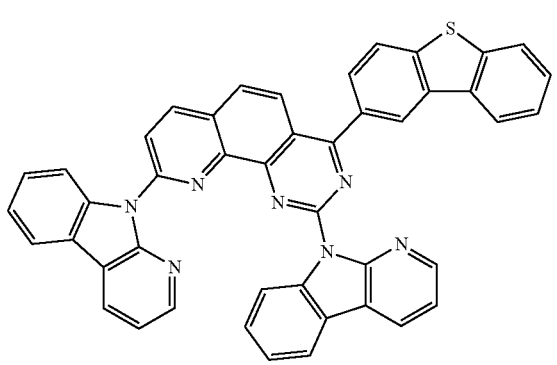

123
-continued
P65
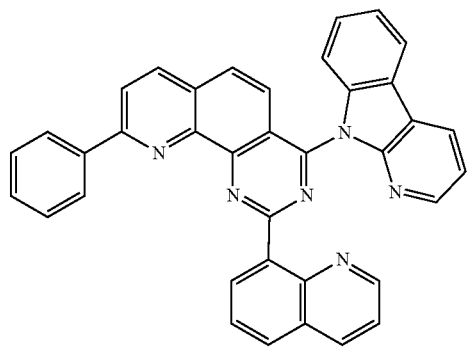
P66
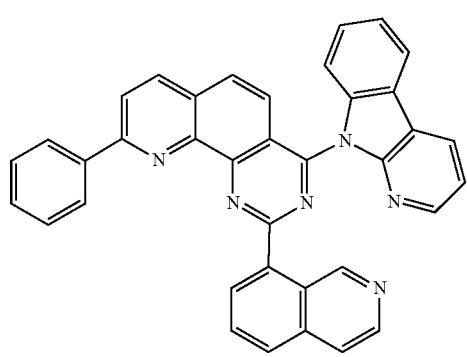
P67
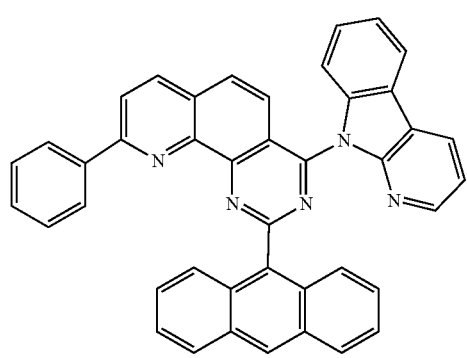
P71
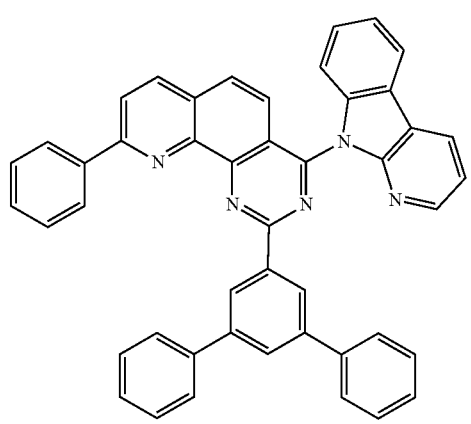
124
-continued
P72
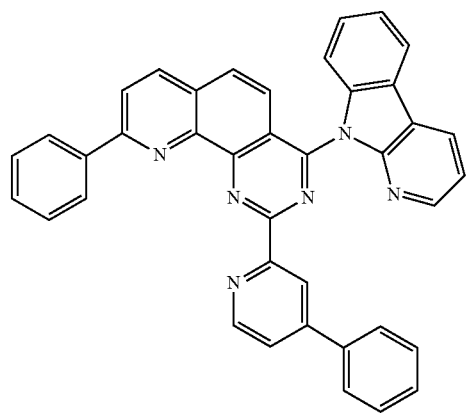
P77
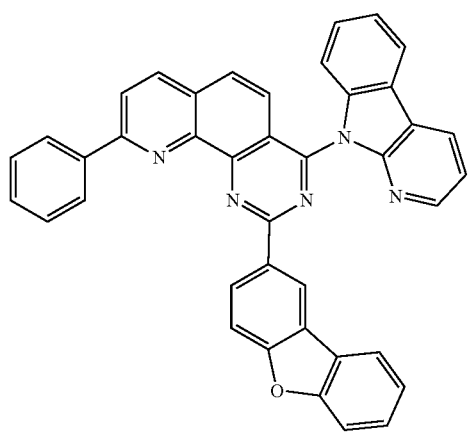
P83
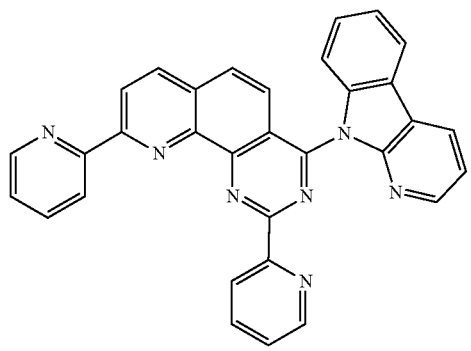
P88
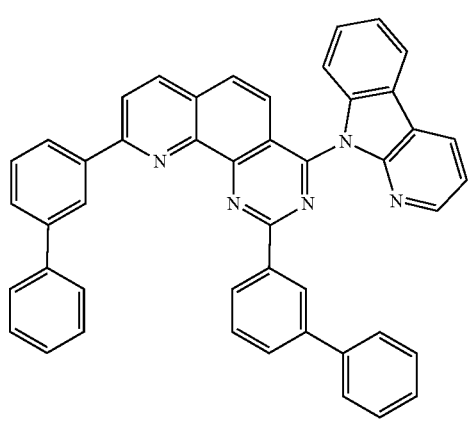

P89 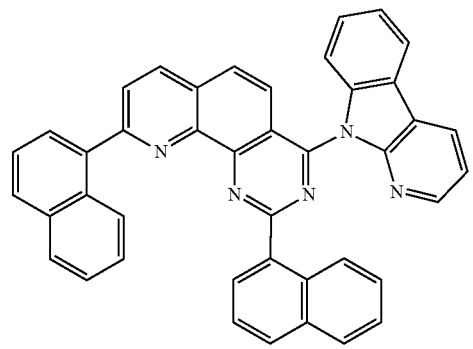
P90 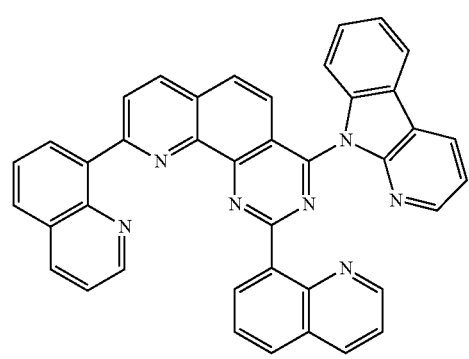
P91 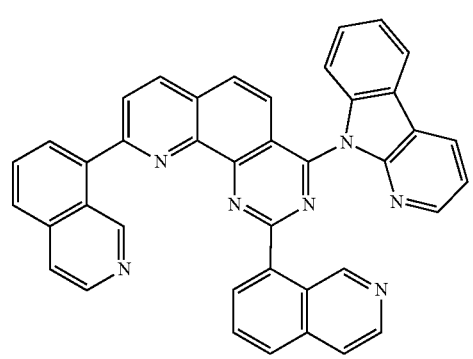
P92 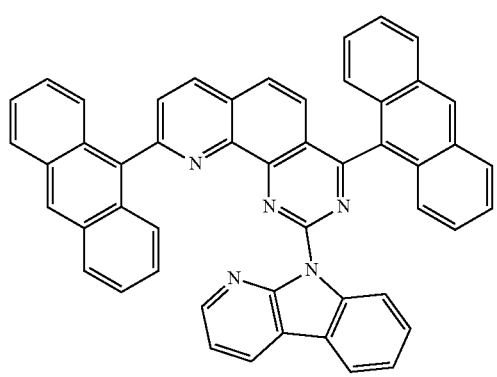
P96 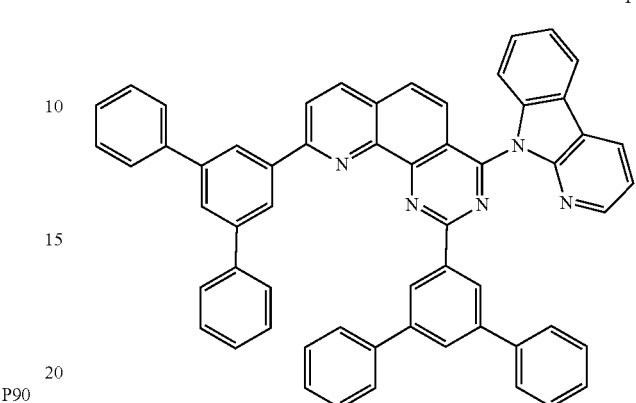
P97 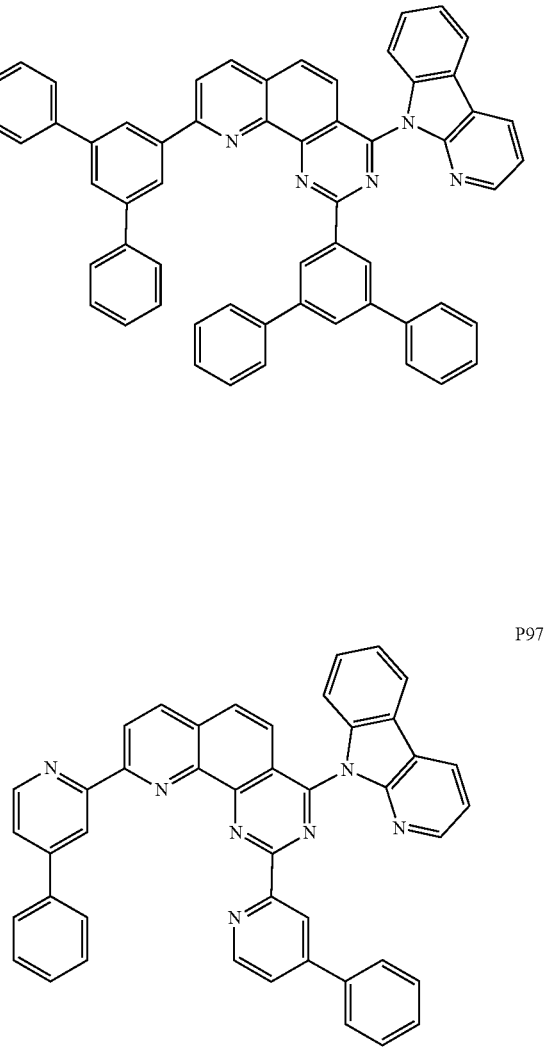
P102 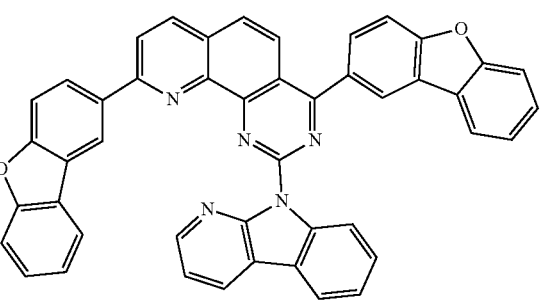

-continued

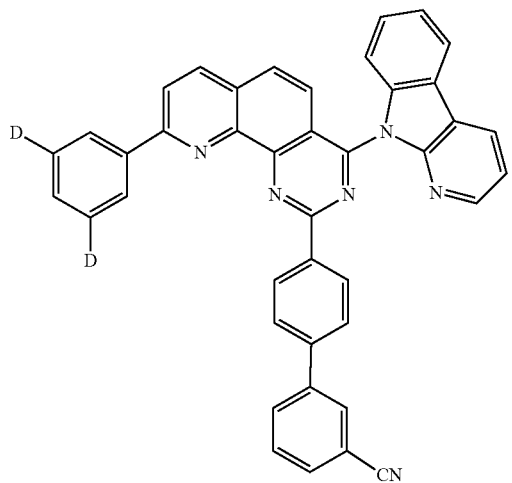

P108

5. An organic electroluminescence device comprising the organic compound according to claim 1.

6. The organic electroluminescence device according to claim 5, wherein the organic compound is used as an electron transporting layer material.

7. An organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, and wherein the electron transport layer contains the organic compound according to claim 1.

8. An organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, and wherein the electron transport layer contains the organic compound according to claim 2.

9. An organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, and wherein the electron transport layer contains the organic compound according to claim 3.

10. An organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, and wherein the electron transport layer contains the organic compound according to claim 4.

* * * * *